(12) United States Patent
Kalish et al.

(10) Patent No.: US 7,750,008 B2
(45) Date of Patent: Jul. 6, 2010

(54) COMPOUNDS, METHODS AND PHARMACEUTICAL COMPOSITIONS FOR INHIBITING PARP

(75) Inventors: Vincent Kalish, Annapolis, MD (US); Jie Zhang, Ellicott City, MD (US); Weizheng Xu, Ellicott City, MD (US); Jia-He Li, Cockeysville, MD (US); Amy D. Xing, San Diego, CA (US); Qun Liu, Columbia, MD (US)

(73) Assignee: Eisai Inc., Woodcliff Lake, NJ (US)

( * ) Notice: Subject to any disclaimer, the term of this patent is extended or adjusted under 35 U.S.C. 154(b) by 0 days.

(21) Appl. No.: 12/540,776

(22) Filed: Aug. 13, 2009

(65) Prior Publication Data

US 2009/0298837 A1    Dec. 3, 2009

Related U.S. Application Data

(62) Division of application No. 12/254,356, filed on Oct. 20, 2008, now Pat. No. 7,601,719, which is a division of application No. 11/834,334, filed on Aug. 6, 2007, now Pat. No. 7,456,178, which is a division of application No. 10/853,714, filed on May 26, 2004, now Pat. No. 7,268,138.

(60) Provisional application No. 60/473,475, filed on May 28, 2003.

(51) Int. Cl.
*C07D 487/06* (2006.01)
*A61K 31/5025* (2006.01)

(52) U.S. Cl. ...................................... 514/248; 544/234

(58) Field of Classification Search ................ 544/234; 514/248
See application file for complete search history.

(56) References Cited

U.S. PATENT DOCUMENTS 6,291,425 B1  9/2001  Li et al.

OTHER PUBLICATIONS

Chalmers (TiPS vol. 17, pp. 166-172 Apr. 1996).
Gagne et al. Current Opinion in Cell Biology 2006, 18:145-151.
Combs et al. Journal of Heterocyclic Chemistry, 1989, vol. 26, 1885-1886.
E.S. Newlands, et al., "Temozolomide: A Review of its Discovery, Chemical Properties, Pre-clinical Development and Clinical Trials," *Cancer Treatment Reviews* (1997) 23, pp. 35-61.
Gagne et al. Current Opinion in Cell Biology 1006, 18; 145-151.

*Primary Examiner*—Kahsay T Habte
(74) *Attorney, Agent, or Firm*—Connolly Bove Lodge & Hutz LLP

(57) ABSTRACT

The present invention provides compounds which inhibit poly(ADP-ribose) polymerase ("PARP"), compositions containing these compounds and methods for using these PARP inhibitors to treat, prevent and/or ameliorate the effects of the conditions described herein.

10 Claims, 1 Drawing Sheet

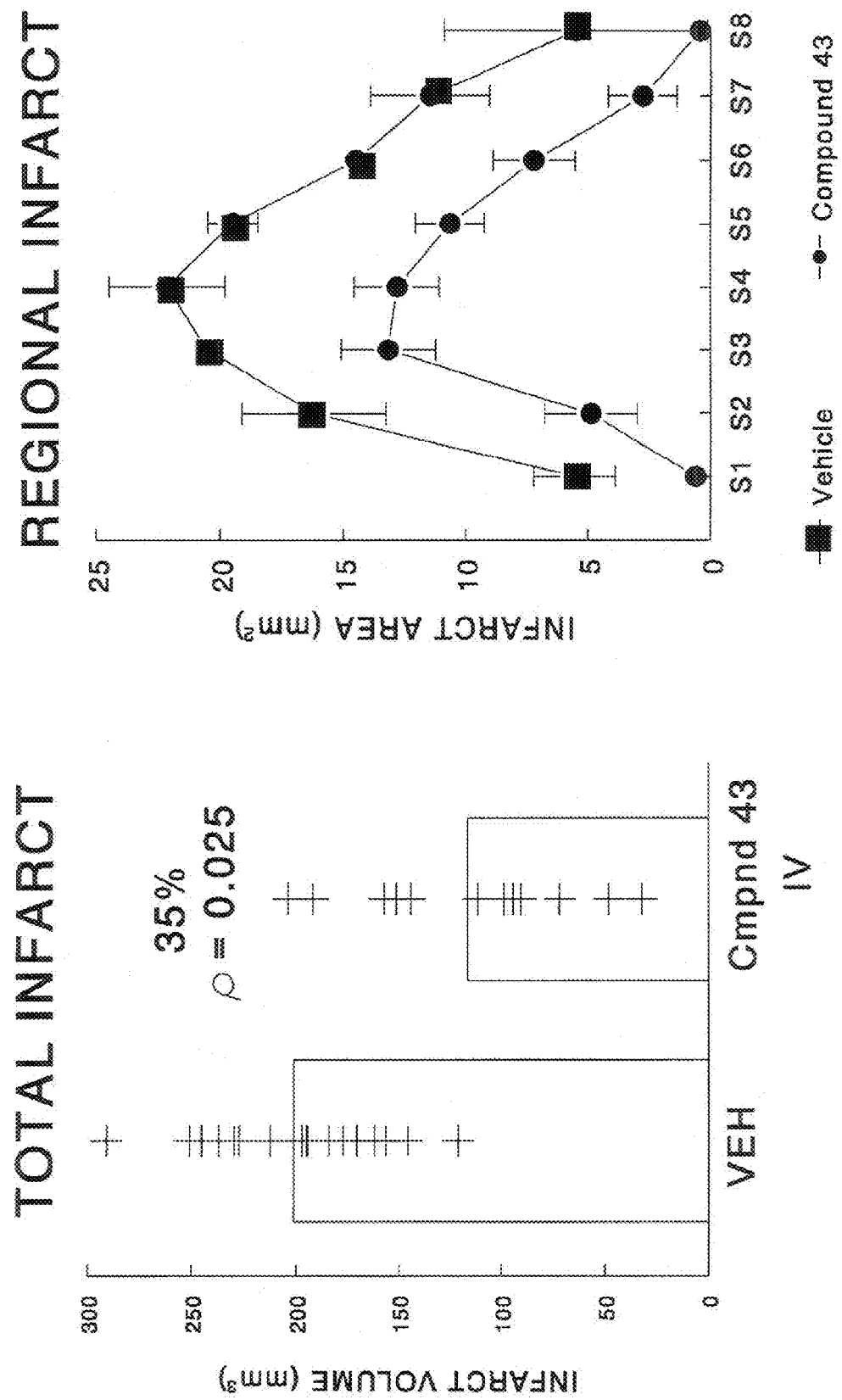
Figure 1 Effect of Compound 43 at 40 mg/kg IV Pre and Post Transient 3VO MCAO (Total Infarct and Regional Infarct).

COMPOUNDS, METHODS AND PHARMACEUTICAL COMPOSITIONS FOR INHIBITING PARP

CROSS REFERENCE TO RELATED APPLICATIONS

This application is a divisional of, and claims domestic priority benefits to U.S. application Ser. No. 12/254,356 filed on Oct. 20, 2008. U.S. application Ser. No. 12/254,356 is a divisional of, and claims benefit to U.S. application Ser. No. 11/834,334 filed on Aug. 6, 2007, which issued as U.S. Pat. No. 7,456,178 on Nov. 25, 2008. U.S. application Ser. No. 11/834,334 is a divisional of, and claims benefit to U.S. application Ser. No. 10/853,714 filed on May 26, 2004, which issued as U.S. Pat. No. 7,268,138 on Sep. 11, 2007; which claimed benefits under 35 U.S.C. §119(e) from, Provisional Application No. 60/473,475, filed May 28, 2003, and claims benefit of PCT/US04/016524, filed May, 26, 2004, the entire content of each of which is hereby incorporated by reference.

The present invention provides compounds, methods and pharmaceutical compositions for inhibiting the nuclear enzyme poly(adenosine 5'-diphospho-ribose) polymerase ["poly(ADP-ribose) polymerase" or "PARP", which is also referred to as ADPRT (NAD:protein (ADP-ribosyl transferase (polymersing)), pADPRT (poly(ADP-ribose) transferase) and PARS (poly(ADP-ribose) synthetase). Moreover, the present invention provides methods of using PARP inhibitors of the invention to prevent and/or treat tissue damage resulting from cell damage or death due to necrosis or apoptosis; neural tissue damage resulting from, for example, ischemia and reperfusion injury, such as cerebral ischemic stroke, head trauma or spinal cord injury; neurological disorders and neurodegenerative diseases, such as, for example, Parkinson's or Alzheimer's diseases and multiple sclerosis; to prevent or treat vascular stroke; to treat or prevent cardiovascular disorders, such as, for example, myocardial infarction; to treat other conditions and/or disorders such as, for example, age-related muscular degeneration, AIDS and other immune senescence diseases, arthritis, atherosclerosis, ataxia telangiectasia, cachexia, cancer, degenerative diseases of skeletal muscle involving replicative senescence, diabetes (such as diabetes mellitus), inflammatory bowel disorders (such as colitis and Crohn's disease), acute pancreatitis, mucositis, hemorrhagic shock, splanchnic artery occlusion shock, multiple organ failure (such as involving any of the kidney, liver, renal, pulmonary, retinal, pancreatic and/or skeletal muscle systems), acute autoimmune thyroiditis, muscular dystrophy, osteoarthritis, osteoporosis, chronic and acute pain (such as neuropathic pain), renal failure, retinal ischemia, septic shock (such as endotoxic shock), local and/or remote endothelial cell dysfunction (such are recognized by endo-dependent relaxant responses and up-regulation of adhesion molecules), inflammation and skin aging; to extend the lifespan and proliferative capacity of cells, such as, for example, as general mediators in the generation of oxidants, proinflammatory mediators and/or cytokines, and general mediators of leukocyte infiltration, calcium ion overload, phospholipid peroxidaion, impaired nitric oxide metabolism and/or reduced ATP production; to alter gene expression of senescent cells; or to radiosensitize hypoxic tumor cells.

Some of the PARP inhibitors used in the inventive methods and pharmaceutical compositions can be readily prepared by standard techniques of organic chemistry, utilizing the general synthetic pathways and examples depicted in publications Wu et al, The Protective Effect of GPI 18078, a Novel Water Soluble Poly (ADP-Ribose) Polymerase Inhibitor in Myocardial Ischemia-Reprefusion Injury, Experimental Biology 2003 (FASEB), Apr. 11-15, 2003; Wu et al, Myocardial Protection and Anti-Inflammatory Effect of GPI 15427, a Novel Water Soluble Poly (ADP-Ribose) Polymerase Inhibitor: Comparison with GPI 6150, Experimental Biology 2003 (FASEB), Apr. 11-15, 2003; Kalish et al, Design, Synthesis and SAR of PARP-1 Inhibitors, ISMC Meeting, Barcelona, Sep. 4, 2002; Xu et al, Design and Synthesis of Novel Potent Poly (ADP-Ribose) Polymerase (PARP) Inhibitors, 224th ACS National Meeting, Boston, Aug. 18-23, 2002; Williams et al, Intravenous Delivery of GPI 15427/C and GPI 16539/C, Potent Water-Soluble PARP Inhibitors, Reduces Infarct Volume Following Permanent and Transient Focal Cerebral Ischemia, Society for Neuroscience, Orlando Fla., October 2002; Tentori L, et al Systemic administration of the PARP-1 inhibitor GPI 15427 increases the anti-tumor activity of temozolomide against metastatic melanoma. Medical Science Monitor, volume 9, supplement 1, p 34, 2003; and Tentori et al, Poly(ADP-Ribose) Polymerase Inhibitor to Increase Temozolomide Efficacy Against Melanoma, Glioma and Lymphoma at the CNS Site AACR poster, April 2003, U.S. Pat. Nos. 6,348,475, 6,545,011, RE36,397, 6,380,211, 6,235, 748, 6,121,278, 6,197,785, 6,380,193, 6,346,536, 6,514,983, 6,306,889, 6,387,902, 6,201,020, and 6,291,425, the entire contents of which patents, patent application and publications are herein incorporated by reference, as though set forth herein in full.

Other PARP inhibitors may be available from commercial suppliers or can be readily prepared by an ordinarily skilled artisan using standard techniques such as those disclosed in U.S. Pat. No. 6,291,425, the entire contents of which reference are herein incorporated by reference as though set forth herein in full.

PARP (EC 2.4.2.30), also known as PARS (for poly(ADP-ribose) synthetase), or ADPRT (for NAD:protein (ADP-ribosyl)transferase (polymerising)), or pADPRT (for poly(ADP-ribose) transferase), is a major nuclear protein of 116 kDa. It is present in almost all eukaryotes. The enzyme synthesizes poly(ADP-ribose), a branched polymer that can consist of over 200 ADP-ribose units from NAD. The protein acceptors of poly(ADP-ribose) are directly or indirectly involved in maintaining DNA integrity. They include histones, topoisomerases, DNA and RNA polymerases, DNA ligases, and $Ca^{2+}$- and $Mg^{2+}$-dependent endonucleases. PARP protein is expressed at a high level in many tissues, most notably in the immune system, heart, brain and germ-line cells. Under normal physiological conditions, there is minimal PARP activity. However, DNA damage causes an immediate activation of PARP by up to 500-fold. Among the many functions attributed to PARP is its major role in facilitating DNA repair by ADP-ribosylation and therefore co-ordinating a number of DNA repair proteins. As a result of PARP activation, NAD levels significantly decline. While many endogenous and exogenous agents have been shown to damage DNA and activate PARP, peroxynitrite, formed from a combination of nitric oxide (NO) and superoxide, appears to be a main perpetrator responsible for various reported disease conditions in vivo, e.g., during shock and inflammation.

Extensive PARP activation leads to severe depletion of NAD in cells suffering from massive DNA damage. The short life of poly(ADP-ribose) (half-life <1 min) results in a rapid turnover rate. Once poly(ADP-ribose) is formed, it is quickly degraded by the constitutively active poly(ADP-ribose) glycohydrolase (PARG), together with phosphodiesterase and (ADP-ribose) protein lyase. PARP and PARG form a cycle that converts a large amount of NAD to ADP-ribose. In less than an hour, over-stimulation of PARP can cause a drop of NAD and ATP to less than 20% of the normal level. Such a scenario is especially detrimental during ischaemia when deprivation of oxygen has already drastically compromised cellular energy output. Subsequent free radical production during reperfusion is assumed to be a major cause of tissue damage. Part of the ATP drop, which is typical in many organs during ischaemia and reperfusion, could be linked to NAD depletion due to poly(ADP-ribose) turnover. Thus, PARP or PARG inhibition is expected to preserve the cellular energy level to potentiate the survival of ischaemic tissues after insult.

Poly(ADP-ribose) synthesis is also involved in the induced expression of a number of genes essential for inflammatory response. PARP inhibitors suppress production of inducible nitric oxide synthase (iNOS) in macrophages, P-type selectin and intercellular adhesion molecule-1 (ICAM-1) in endothelial cells. Such activity underlies the strong anti-inflammation effects exhibited by PARP inhibitors. PARP inhibition is able to reduce necrosis by preventing translocation and infiltration of neutrophils to the injured tissues. (Zhang, J. "PARP inhibition: a novel approach to treat ischaemia/reperfusion and inflammation-related injuries", Chapter 10 in *Emerging Drugs* (1999) 4: 209-221 Ashley Publications Ltd., and references cited therein.)

PARP production is activated by damaged DNA fragments which, once activated, catalyzes the attachment of up to 100 ADP-ribose units to a variety of nuclear proteins, including histones and PARP itself. During major cellular stresses the extensive activation of PARP can rapidly lead to cell damage or death through depletion of energy stores. As four molecules of ATP are consumed for every molecule of NAD (the source of ADP-ribose and PARP substrate) regenerated, NAD is depleted by massive PARP activation and, in the efforts to re-synthesize NAD, ATP may also be depleted.

It has been reported that PARP activation plays a key role in both NMDA- and NO-induced neurotoxicity. This has been demonstrated in cortical cultures and in hippocampal slices wherein prevention of toxicity is directly correlated to PARP inhibition potency (Zhang et al., "Nitric Oxide Activation of Poly(ADP-Ribose) Synthetase in Neurotoxicity", Science, 263:687-89 (1994) and Wallis et al., "Neuroprotection Against Nitric Oxide Injury with Inhibitors of ADP-Ribosylation", NeuroReport, 5:3, 245-48 (1993)). The potential role of PARP inhibitors in treating neurodegenerative diseases and head trauma has thus been recognized even if the exact mechanism of action has not yet been elucidated (Endres et al., "Ischemic Brain Injury is Mediated by the Activation of Poly(ADP-Ribose)Polymerase", J. Cereb. Blood Flow Metabol., 17:1143-51 (1997) and Wallis et al., "Traumatic Neuroprotection with Inhibitors of Nitric Oxide and ADP-Ribosylation, Brain Res., 710:169-77 (1996)).

Similarly, it has been demonstrated that single injections of PARP inhibitors have reduced the infarct size caused by ischemia and reperfusion of the heart or skeletal muscle in rabbits. In these studies, a single injection 3-amino-benzamide (10 mg/kg), either one minute before occlusion or one minute before reperfusion, caused similar reductions in infarct size in the heart (32-42%) while 1,5-dihydroxyisoquinoline (1 mg/kg), another PARP inhibitor, reduced infarct size by a comparable degree (38-48%). Thiemermann et al., "Inhibition of the Activity of Poly(ADP Ribose) Synthetase Reduces Ischemia-Reperfusion Injury in the Heart and Skeletal Muscle", Proc. Natl. Acad. Sci. USA, 94:679-83 (1997). These results make it reasonable to suspect that PARP inhibitors could salvage previously ischemic heart or skeletal muscle tissue.

PARP activation can also be used as a measure of damage following neurotoxic insults following over-exposure to any of glutamate (via NMDA receptor stimulation), reactive oxygen intermediates, amyloid β-protein, N-methyl-4-phenyl-1,2,3,6-tetrahydropyridine (MPTP) or its active metabolite N-methyl-4-phenylpyridine (MPP$^+$), which participate in pathological conditions such as stroke, Alzheimer's disease and Parkinson's disease. Zhang et al., "Poly(ADP-Ribose) Synthetase Activation: An Early Indicator of Neurotoxic DNA Damage", J. Neurochem., 65:3, 1411-14 (1995). Other studies have continued to explore the role of PARP activation in cerebellar granule cells in vitro and in MPTP neurotoxicity. Cosi et al., "Poly(ADP-Ribose) Polymerase (PARP) Revisited. A New Role for an Old Enzyme: PARP Involvement in Neurodegeneration and PARP Inhibitors as Possible Neuroprotective Agents", Ann. N.Y. Acad. Sci., 825:366-79 (1997); and Cosi et al., "Poly(ADP-Ribose) Polymerase Inhibitors Protect Against MPTP-induced Depletions of Striatal Dopamine and Cortical Noradrenaline in C57B1/6 Mice", Brain Res., 729:264-69 (1996). Excessive neural exposure to glutamate, which serves as the predominate central nervous system neurotransmitter and acts upon the N-methyl-D-aspartate (NMDA) receptors and other subtype receptors, most often occurs as a result of stroke or other neurodegenerative processes. Oxygen deprived neurons release glutamate in great quantities during ischemic brain insult such as during a stroke or heart attack. This excess release of glutamate in turn causes over-stimulation (excitotoxicity) of N-methyl-D-aspartate (NMDA), AMPA, Kainate and MGR receptors, which open ion channels and permit uncontrolled ion flow (e.g., $Ca^{2+}$ and $Na^+$ into the cells and $K^+$ out of the cells) leading to overstimulation of the neurons. The over-stimulated neurons secrete more glutamate, creating a feedback loop or domino effect which ultimately results in cell damage or death via the production of proteases, lipases and free radicals. Excessive activation of glutamate receptors has been implicated in various neurological diseases and conditions including epilepsy, stroke, Alzheimer's disease, Parkinson's disease, Amyotrophic Lateral Sclerosis (ALS), Huntington's disease, schizophrenia, chronic pain, ischemia and neuronal loss following hypoxia, hypoglycemia, ischemia, trauma, and nervous insult. Glutamate exposure and stimulation has also been implicated as a basis for compulsive disorders, particularly drug dependence. Evidence includes findings in many animal species, as well as in cerebral cortical cultures treated with glutamate or NMDA, that glutamate receptor antagonists (i.e., compounds which block glutamate from binding to or activating its receptor) block neural damage following vascular stroke. Dawson et al., "Protection of the Brain from Ischemia", Cerebrovascular Disease, 319-25 (H. Hunt Batjer ed., 1997). Attempts to prevent excitotoxicity by blocking NMDA, AMPA, Kainate and MGR receptors have proven difficult because each receptor has multiple sites to which glutamate may bind and hence finding an effective mix of antagonists or universal antagonist to prevent binding of glutamate to all of the receptor and allow testing of this theory, has been difficult. Moreover, many of the compositions that are effective in blocking the receptors are also toxic to animals. As such, there is presently no known effective treatment for glutamate abnormalities.

The stimulation of NMDA receptors by glutamate, for example, activates the enzyme neuronal nitric oxide synthase (nNOS), leading to the formation of nitric oxide (NO), which also mediates neurotoxicity. NMDA neurotoxicity may be prevented by treatment with nitric oxide synthase (NOS) inhibitors or through targeted genetic disruption of nNOS in vitro. Dawson et al., "Nitric Oxide Mediates Glutamate Neurotoxicity in Primary Cortical Cultures", Proc. Natl. Acad. Sci. USA, 88:6368-71 (1991); and Dawson et al., "Mechanisms of Nitric Oxide-mediated Neurotoxicity in Primary Brain Cultures", J. Neurosci., 13:6, 2651-61 (1993), Dawson et al., "Resistance to Neurotoxicity in Cortical Cultures from Neuronal Nitric Oxide Synthase-Deficient Mice", J. Neurosci., 16:8, 2479-87 (1996), Iadecola, "Bright and Dark Sides of Nitric Oxide in Ischemic Brain Injury", Trends Neurosci., 20:3, 132-39 (1997), Huang et al., "Effects of Cerebral Ischemia in Mice Deficient in Neuronal Nitric Oxide Synthase", Science, 265:1883-85 (1994), Beckman et al., "Pathological Implications of Nitric Oxide, Superoxide and Peroxynitrite Formation", Biochem. Soc. Trans., 21:330-34 (1993), and Szabó et al., "DNA Strand Breakage, Activation of Poly (ADP-Ribose) Synthetase, and Cellular Energy Depletion are Involved in the Cytotoxicity in Macrophages and Smooth Muscle Cells Exposed to Peroxynitrite", Proc. Natl. Acad. Sci. USA, 93:1753-58 (1996).

It is also known that PARP inhibitors, such as 3-amino benzamide, affect DNA repair generally in response, for example, to hydrogen peroxide or gamma-radiation. Cristovao et al., "Effect of a Poly(ADP-Ribose) Polymerase Inhibitor on DNA Breakage and Cytotoxicity Induced by Hydrogen Peroxide and γ-Radiation," Terato., Carcino., and Muta., 16:219-27 (1996). Specifically, Cristovao et al. observed a PARP-dependent recovery of DNA strand breaks in leukocytes treated with hydrogen peroxide.

PARP inhibitors have been reported to be effective in radiosensitizing hypoxic tumor cells and effective in preventing tumor cells from recovering from potentially lethal damage of DNA after radiation therapy, presumably by their ability to prevent DNA repair. U.S. Pat. Nos. 5,032,617; 5,215,738; and 5,041,653.

Evidence also exists that PARP inhibitors are useful for treating inflammatory bowel disorders, such as colitis. Salzman et al., "Role of Peroxynitrite and Poly(ADP-Ribose) Synthase Activation Experimental Colitis," Japanese J. Pharm., 75, Supp. I:15 (1997). Specifically, Colitis was induced in rats by intraluminal administration of the hapten trinitrobenzene sulfonic acid in 50% ethanol. Treated rats received 3-aminobenzamide, a specific inhibitor of PARP activity. Inhibition of PARP activity reduced the inflammatory response and restored the morphology and the energetic status of the distal colon. See also, Southan et al., "Spontaneous Rearrangement of Aminoalkylithioureas into Mercaptoalkylguanidines, a Novel Class of Nitric Oxide Synthase Inhibitors with Selectivity Towards the Inducible Isoform", Br. J. Pharm., 117:619-32 (1996); and Szabó et al., "Mercaptoethylguanidine and Guanidine Inhibitors of Nitric Oxide Synthase React with Peroxynitrite and Protect Against Peroxynitrite-induced Oxidative Damage", J. Biol. Chem., 272: 9030-36 (1997).

Evidence also exists that PARP inhibitors are useful for treating arthritis. Szabó et al., "Protective Effects of an Inhibitor of Poly(ADP-Ribose)Synthetase in Collagen-Induced Arthritis," Japanese J. Pharm., 75, Supp. I:102 (1997); Szabó et al., "DNA Strand Breakage, Activation of Poly(ADP-Ribose)Synthetase, and Cellular Energy Depletion are Involved in the Cytotoxicity in Macrophages and Smooth Muscle Cells Exposed to Peroxynitrite," Proc. Natl. Acad. Sci. USA, 93:1753-58 (March 1996); and Bauer et al., "Modification of Growth Related Enzymatic Pathways and Apparent Loss of Tumorigenicity of a ras-transformed Bovine Endothelial Cell Line by Treatment with 5-Iodo-6-amino-1,2-benzopyrone ($INH_2BP$)", Intl. J. Oncol., 8:239-52 (1996); and Hughes et al., "Induction of T Helper Cell Hyporesponsiveness in an Experimental Model of Autoimmunity by Using Nonmitogenic Anti-CD3 Monoclonal Antibody", J. Immuno., 153:3319-25 (1994).

Further, PARP inhibitors appear to be useful for treating diabetes. Heller et al., "Inactivation of the Poly(ADP-Ribose) Polymerase Gene Affects Oxygen Radical and Nitric Oxide Toxicity in Islet Cells," J. Biol. Chem., 270:19, 11176-80 (May 1995). Heller et al. used cells from mice with inactivated PARP genes and found that these mutant cells did not show $NAD^+$ depletion after exposure to DNA-damaging radicals. The mutant cells were also found to be more resistant to the toxicity of NO.

PARP inhibitors have been shown to be useful for treating endotoxic shock or septic shock. Zingarelli et al., "Protective Effects of Nicotinamide Against Nitric Oxide-Mediated Delayed Vascular Failure in Endotoxic Shock: Potential Involvement of PolyADP Ribosyl Synthetase," Shock, 5:258-64 (1996), suggests that inhibition of the DNA repair cycle triggered by poly(ADP ribose) synthetase has protective effects against vascular failure in endotoxic shock. Zingarelli et al. found that nicotinamide protects against delayed, NO-mediated vascular failure in endotoxic shock. Zingarelli et al. also found that the actions of nicotinamide may be related to inhibition of the NO-mediated activation of the energy-consuming DNA repair cycle, triggered by poly(ADP ribose) synthetase. Cuzzocrea, "Role of Peroxynitrite and Activation of Poly(ADP-Ribose) Synthetase in the Vascular Failure Induced by Zymosan-activated Plasma," Brit. J. Pharm., 122: 493-503 (1997).

PARP inhibitors have been used to treat cancer. Suto et al., "Dihydroisoquinolinones: The Design and Synthesis of a New Series of Potent Inhibitors of Poly(ADP-Ribose) Polymerase", Anticancer Drug Des., 7:107-17 (1991). In addition, Suto et al., U.S. Pat. No. 5,177,075, discusses several isoquinolines used for enhancing the lethal effects of ionizing radiation or chemotherapeutic agents on tumor cells. Weltin et al., "Effect of 6(5H)-Phenanthridinone, an Inhibitor of Poly(ADP-ribose) Polymerase, on Cultured Tumor Cells", Oncol. Res., 6:9, 399-403 (1994), discusses the inhibition of PARP activity, reduced proliferation of tumor cells, and a marked synergistic effect when tumor cells are co-treated with an alkylating drug.

Still another use for PARP inhibitors is the treatment of peripheral nerve injuries, and the resultant pathological pain syndrome known as neuropathic pain, such as that induced by chronic constriction injury (CCI) of the common sciatic nerve and in which transsynaptic alteration of spinal cord dorsal horn characterized by hyperchromatosis of cytoplasm and nucleoplasm (so-called "dark" neurons) occurs. Mao et al., Pain, 72:355-366 (1997).

PARP inhibitors have also been used to extend the lifespan and proliferative capacity of cells including treatment of diseases such as skin aging, Alzheimer's disease, atherosclerosis, osteoarthritis, osteoporosis, muscular dystrophy, degenerative diseases of skeletal muscle involving replicative senescence, age-related muscular degeneration, immune senescence, AIDS, and other immune senescence diseases; and to alter gene expression of senescent cells. WO 98/27975.

Large numbers of known PARP inhibitors have been described in Banasik et al., "Specific Inhibitors of Poly(ADP-Ribose) Synthetase and Mono(ADP-Ribosyl)-Transferase", J. Biol. Chem., 267:3, 1569-75 (1992), and in Banasik et al., "Inhibitors and Activators of ADP-Ribosylation Reactions", Molec. Cell. Biochem., 138:185-97 (1994). However, effective use of these PARP inhibitors, in the ways discussed above, has been limited by the concurrent production of unwanted side-effects (Milam et al., "Inhibitors of Poly(Adenosine Diphosphate-Ribose) Synthesis: Effect on Other Metabolic Processes", Science, 223:589-91 (1984)).

There continues to be a need for effective and potent PARP inhibitors which produce minimal side-effects. The present invention provides compounds, compositions for, and methods of, inhibiting PARP activity for treating and/or preventing cellular, tissue and/or organ damage resulting from cell damage or death due to, for example, necrosis or apoptosis. The compounds and compositions of the present invention are specifically useful in ameliorating, treating and/or preventing neural tissue or cell damage, including that following focal ischemia and reperfusion injury. Generally, inhibition of PARP activity spares the cell from energy loss, preventing irreversible depolarization of the neurons and, thus, provides neuroprotection. While not wishing to be bound by any mechanistic theory, the inhibition of PARP activity by use of the compounds, compositions and methods of the present invention is believed to protect cells, tissue and organs by protection against the ill-effects of reactive free radicals and nitric oxide. The present invention therefore also provides methods of treating and/or preventing cells, tissue and/or organs from reactive free radical and/or nitric oxide induced damage or injury.

The present invention provides compounds which inhibit poly(ADP-ribose) polymerase ("PARP"), compositions containing these compounds and methods for using these PARP inhibitors to treat, prevent and/or ameliorate the effects of the conditions described herein.

In one embodiment, the present invention provides compounds of Formula I:

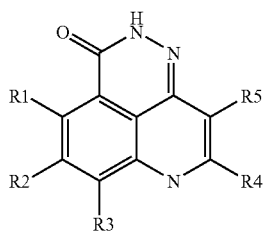

I or a pharmaceutically acceptable salt, prodrug, metabolite, or hydrate;

where:
R1 is H, halogen, alkoxy, or lower alkyl;
R2 is H, halogen, alkoxy, or lower alkyl;
R3 is independently H, amino, hydroxy, —N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl;
R4 is independently H, amino, hydroxy, —N—N, —CO—N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl; and R5 is independently H, amino, hydroxy, —N—N, —CO—N—N, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl.

The present invention also provides compounds where
R1 is H, F, Cl, methoxy, or methyl;
R2 is H, F, Cl, methoxy, or methyl;
R3 is independently H, amino, hydroxy, —N—N, halogen-substituted amino, —O-alkyl, —O-aryl, or an optionally substituted alkyl, alkeny, —COR8, where R8 is H, —OH an optionally substituted alkyl, or alkenyl, or —OR6 or —NR6R7 where R6 and R7 are each independently hydrogen or an optionally substituted alkyl, or alkenyl;
R4 is independently H, amino, hydroxy, —N—N, —CO—N—N, halogen-substituted amino, —O-alkyl, —O-aryl, or an optionally substituted alkyl, alkenyl, —COR8, where R8 is H, —OH an optionally substituted alkyl, or alkenyl, or —OR6 or —NR6R7 where R6 and R7 are each independently hydrogen or an optionally substituted alkyl, or alkenyl; and
R5 is independently H, amino, hydroxy, —N—N, —CO—N—N, halogen-substituted amino, —O-alkyl, —O-aryl, or an optionally substituted alkyl, alkenyl —COR8, where R8 is H, —OH an optionally substituted alkyl, or alkenyl, or —OR6 or —NR6R7 where R6 and R7 are each independently hydrogen or an optionally substituted alkyl, or alkenyl.

The present invention also provides the following compounds

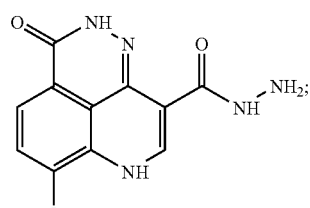

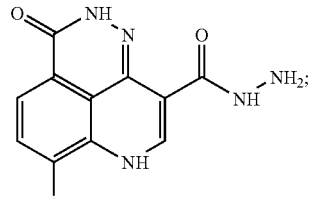

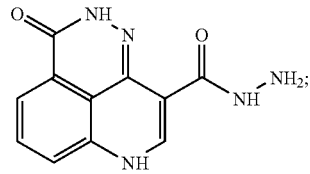

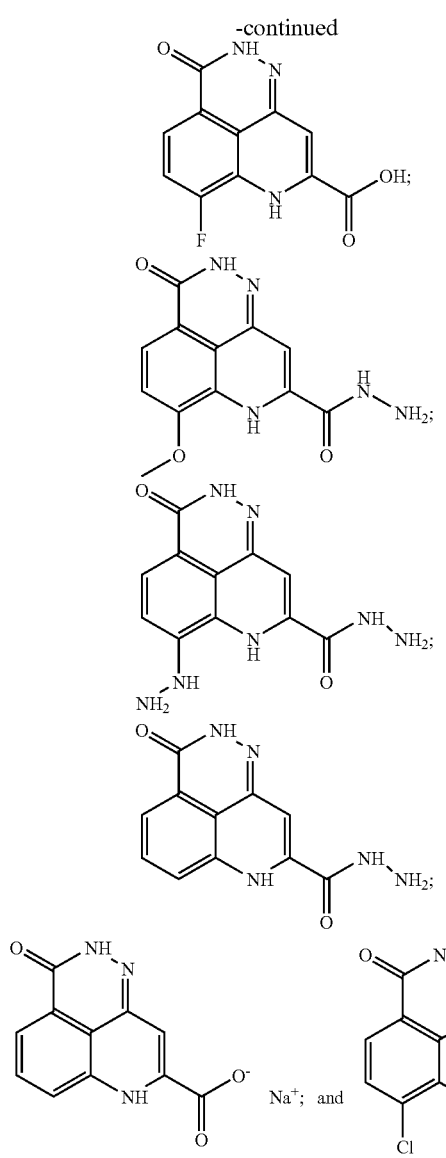

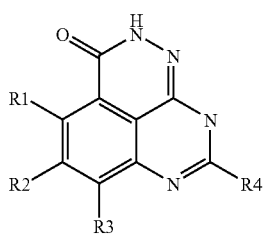

In another embodiment, the present invention provides compounds of Formula II:

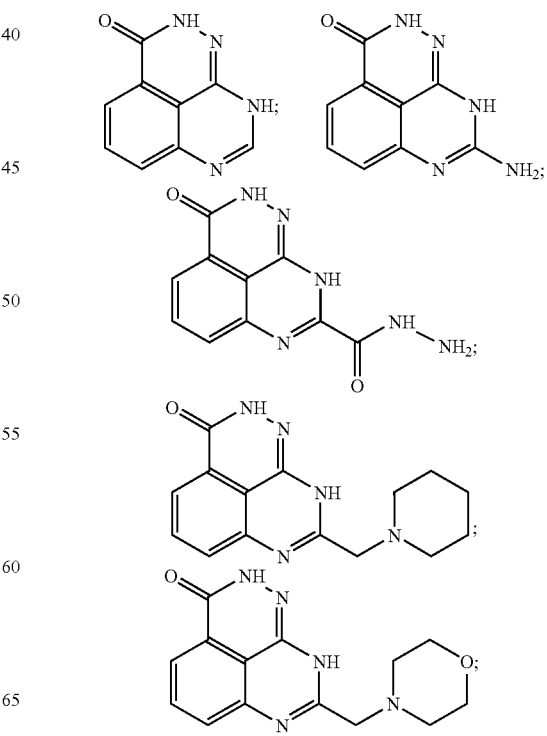

where

R1 is H, halogen, alkoxy, or lower alkyl;

R2 is H, halogen, alkoxy, or lower alkyl;

R3 is independently H, amino, hydroxy, —NH—NH$_2$, halogen-substituted amino, —O-alkyl, —O-aryl, or an optionally substituted alkyl, alkenyl, alkynyl, cycloalkyl, het-erocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl; and R4 is independently H, amino, hydroxy, —NH—NH2, —CO—NH—NH2, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, alkenyl, alkynyl, cycloalkyl, heterocycloalkyl, aryl or heteroaryl, or —OR6 or —NR6R7 where R6 and R7 are each independently hydrogen or an optionally substituted alkyl, alkenyl, alkynyl, cycloalkyl, heterocycloalkyl, aryl or heteroaryl.

In another embodiment, the present invention provides compounds where

R1 is H, F, Cl, methoxy, or methyl;

R2 is H, F, Cl, methoxy, or methyl;

R3 is independently H, amino, hydroxy, —NH—NH2, halogen-substituted amino, —O-alkyl, —O-aryl, or an optionally substituted alkyl, alkenyl, —COR8, where R8 is H, —OH an optionally substituted alkyl, or alkenyl, or —OR6 or —NR6R7 where R6 and R7 are each independently hydrogen or an optionally substituted alkyl, or alkenyl; and R4 is independently H, amino, hydroxy, —NH—NH2, —CO—NH—NH2, halogen-substituted amino, —O-alkyl, —O-aryl, or an optionally substituted alkyl, alkenyl, alkynyl, cycloalkyl, heterocycloalkyl, aryl, heteroaryl, —COR8, where R8 is H, —OH an optionally substituted alkyl, or alkenyl, or —OR6 or —NR6R7 where R6 and R7 are each independently hydrogen or an optionally substituted alkyl, or alkenyl.

In another embodiment, the present invention provides the following compounds

The present invention also provides the following compounds of group:

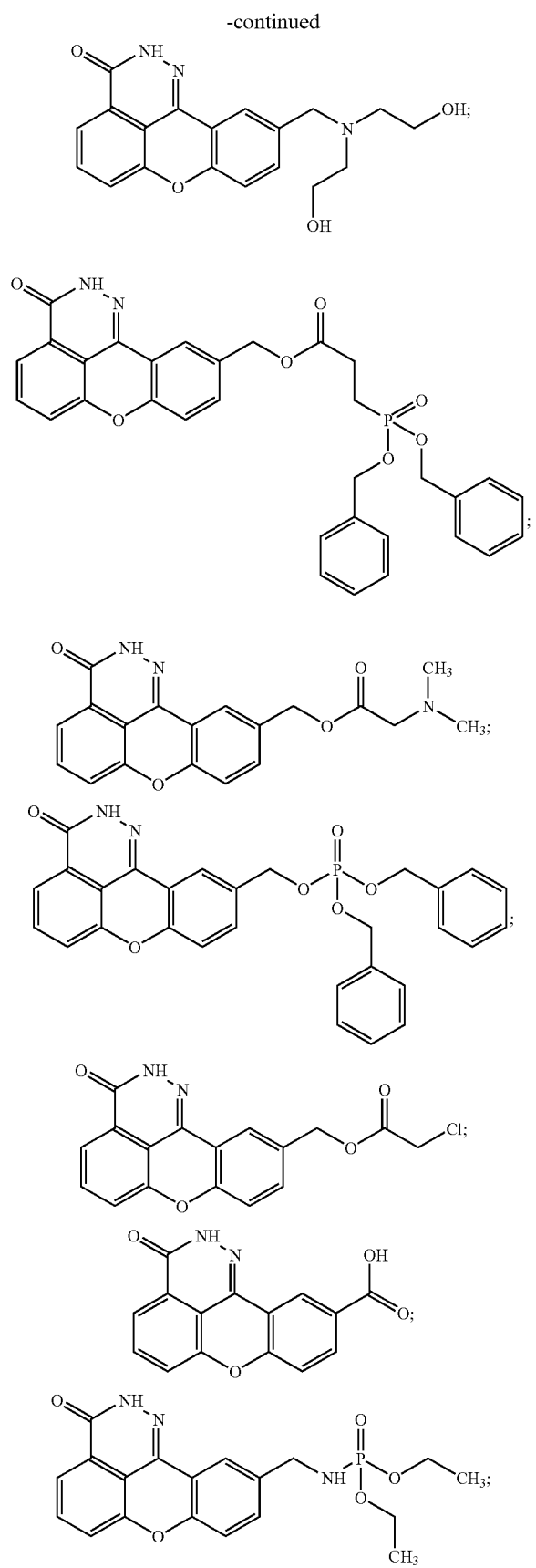
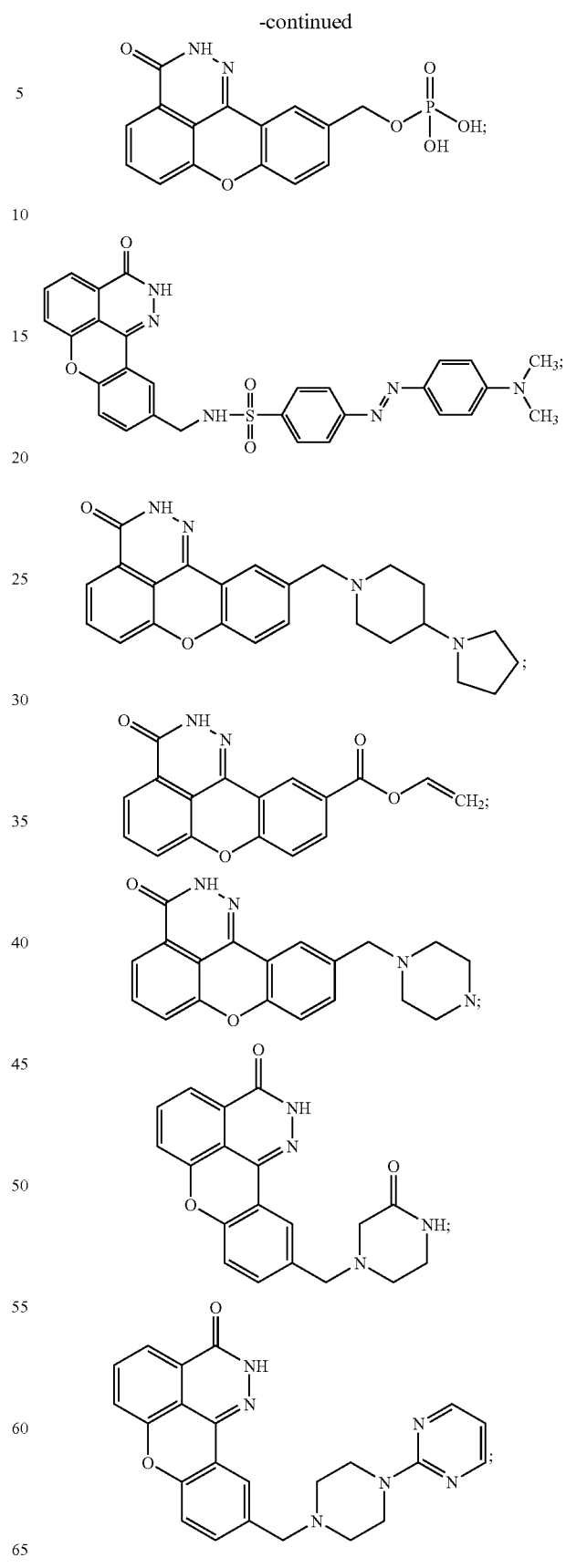

-continued

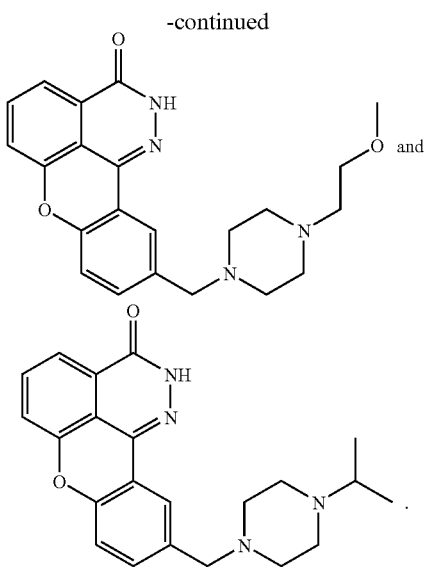

and

Broadly, the compounds and compositions of the present invention can be used to treat or prevent cell damage or death due to necrosis or apoptosis, cerebral ischemia and reperfusion injury or neurodegenerative diseases in an animal, such as a human. The compounds and compositions of the present invention can be used to extend the lifespan and proliferative capacity of cells and thus can be used to treat or prevent diseases associated therewith; they alter gene expression of senescent cells; and they radiosensitize hypoxic tumor cells. Preferably, the compounds and compositions of the invention can be used to treat or prevent tissue damage resulting from cell damage or death due to necrosis or apoptosis, and/or effect neuronal activity, either mediated or not mediated by NMDA toxicity. The compounds of the present invention are not limited to being useful in treating glutamate mediated neurotoxicity and/or NO-mediated biological pathways. Further, the compounds of the invention can be used to treat or prevent other tissue damage related to PARP activation, as described herein.

The present invention provides compounds which inhibit the in vitro and/or in vivo polymerase activity of poly(ADP-ribose) polymerase (PARP), and compositions containing the disclosed compounds.

The present invention provides methods to inhibit, limit and/or control the in vitro and/or in vivo polymerase activity of poly(ADP-ribose) polymerase (PARP) in solutions, cells, tissues, organs or organ systems. In one embodiment, the present invention provides methods of limiting or inhibiting PARP activity in a mammal, such as a human, either locally or systemically.

The present invention provides methods to treat and/or prevent diseases, syndromes and/or conditions exacerbated by or involving the increased generation of PARP. These methods involve application or administration of the compounds of the present invention to cells, tissues, organs or organ systems of a person in need of such treatment or prevention.

In one embodiment, the present invention provides methods to treat and/or prevent cardiovascular tissue damage resulting from cardiac ischemia or reperfusion injury. Reperfusion injury, for instance, occurs at the termination of cardiac bypass procedures or during cardiac arrest when the heart, once prevented from receiving blood, begins to reperfuse and these methods involve administration of the compounds and compositions of the present invention preferably prior to, or immediately subsequent to reperfusion, such that reperfusion injury is prevented, treated or reduced. The present invention also provides methods of preventing and/or treating vascular stroke, cardiovascular disorders In another embodiment, the present invention provides in vitro or in vivo methods to extend or increase the lifespan and/or proliferation capacity of cells and thus also methods to treat and/or prevent diseases associated therewith and induced or exacerbated by cellular senescence including skin aging, atherosclerosis, osteoarthritis, osteoporosis, muscular dystrophy, degenerative diseases of skeletal muscle involving replicative senescence, age-related muscular degeneration, immune senescence, AIDS and other immune senescence diseases, and other diseases associated with cellular senescence and aging, as well as to alter the gene expression of senescent cells.

In another embodiment, the present invention provides methods of treating or preventing or ameliorating the effect of cancer and/or to radiosensitize hypoxic tumor cells to render the tumor cells more susceptible to radiation therapy and thereby to prevent the tumor cells from recovering from potentially lethal damage of DNA after radiation therapy. A method of this embodiment is directed to specifically and preferentially radiosensitizing tumor cells rendering the tumor cells more susceptible to radiation therapy than non-tumor cells.

In another embodiment the present invention provides methods of preventing and/or treating vascular stroke, cardiovascular disorders; to treat other conditions and/or disorders such as age-related muscular degeneration, AIDS and other immune senescence diseases, arthritis, atherosclerosis, cachexia, cancer, degenerative diseases of skeletal muscle involving replicative senescence, diabetes, head trauma, spinal chord injury, immune senescence, inflammatory bowel disorders (such as colitis and Crohn's disease), acute pancreatitis, mucositis, hemorrhagic shock, splanchnic artery occlusion shock, multiple organ failure (such as involving any of the kidney, liver, renal, pulmonary, retianl, pancreatic and/or skeletal muscles systems), acute autoimmune thyroiditis, muscular dystrophy, osteoarthritis, osteoporosis, chronic and/or acute pain (such as neuropathic pain), renal failure, retinal ischemia, septic shock (such as endotoxic shock), local and/or remote entothelial cell dysfunction (such are recognized by endo-dependent relaxant responses and up-regulation of adhesion molecules), inflammation and skin aging.

In another embodiment of the present invention, a person diagnosed with acute retinal ischemia or acute vascular stroke is immediately administered parenterally, either by intermittent or continuous intravenous administration, a compound of the present invention either as a single dose or a series of divided doses of the compound. After this initial treatment, and depending on the person's presenting neurological symptoms, the person optionally may receive the same or a different compound of the invention in the form of another parenteral dose. The compound of the invention can be administered by intermittent or continuous administration via implantation of a biocompatible, biodegradable polymeric matrix delivery system containing the compound, or via a subdural pump inserted to administer the compound directly to the infarct area of the brain.

In another embodiment, the present invention provides methods to extend the lifespan and proliferative capacity of cells, such as, for example, in using the compounds of the invention as general mediators in the generation of oxidants, proinflammatory mediators and/or cytokines, and/or general mediators of leukocyte infiltration, calcium ion overload, phospholipid peroxidaion, impaired nitric oxide metabolism and/or reduced ATP production.

BRIEF DESCRIPTION OF THE DRAWINGS

FIG. 1 Effect of Compound 43 at 40 mg/kg IV Pre and Post Transient 3VO MCAO (Total Infarct and Regional Infarct).

The compounds of the present invention can treat or prevent tissue damage resulting from cell damage or death due to necrosis or apoptosis; can ameliorate neural or cardiovascular tissue damage, including that following focal ischemia, myocardial infarction, and reperfusion injury; can treat various diseases and conditions caused or exacerbated by PARP activity; can extend or increase the lifespan or proliferative capacity of cells; can alter the gene expression of senescent cells; and can radiosensitize cells. Generally, inhibition of PARP activity spares the cells from energy loss, preventing, in the case of neural cells, irreversible depolarization of the neurons, and thus, provides neuroprotection. While not being bound to any one particular theory, it is thought that PARP activation may play a common role in still other excitotoxic mechanisms, perhaps as yet undiscovered, in addition to the production of free radicals and NO.

For the foregoing reasons, the present invention further relates to a method of administering a therapeutically effective amount of the above-identified compounds in an amount sufficient to inhibit PARP activity, to treat or prevent tissue damage resulting from cell damage or death due to necrosis or apoptosis, to effect a neuronal activity not mediated by NMDA toxicity, to effect a neuronal activity mediated by NMDA toxicity, to treat neural tissue damage resulting from ischemia and reperfusion injury, neurological disorders and neurodegenerative diseases; to prevent or treat vascular stroke; to treat or prevent cardiovascular disorders; to treat other conditions and/or disorders such as age-related muscular degeneration, AIDS and other immune senescence diseases, arthritis, atherosclerosis, ataxia telangiectasia, cachexia, cancer, degenerative diseases of skeletal muscle involving replicative senescence, diabetes, head trauma, immune senescence, inflammatory bowel disorders (such as colitis and Crohn's disease), muscular dystrophy, osteoarthritis, osteoporosis, chronic and/or acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells. The present invention also relates to treating diseases and conditions in an animal which comprises administering to said animal a therapeutically effective amount of the above-identified compounds.

The present invention relates to a method of treating, preventing or inhibiting a neurological disorder in an animal, which comprises administering to said animal a therapeutically effective amount of the above-identified compounds. In a another embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another embodiment is when the reperfusion injury is a vascular stroke. Yet another embodiment is when the peripheral neuropathy is caused by Guillain-Barre syndrome. Still another embodiment is when the demyelinating disease and neurological disorder relates to neurodegeneration. Another embodiment is when the reperfusion injury is a vascular stroke. Still another preferred embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

Another embodiment is a method of treating, preventing or inhibiting a cardiovascular disease in an animal, such as angina pectoris, myocardial infarction, cardiovascular ischemia, and cardiovascular tissue damage related to PARP activation, by administering to said animal an effective amount of the compounds of the present invention.

The present invention also contemplates the use of a compound the present invention for inhibiting PARP activity, for treating, preventing or inhibiting tissue damage resulting from cell damage or death due to necrosis or apoptosis, for treating, preventing or inhibiting a neurological disorder in an animal.

In another embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration.

Another embodiment is when the reperfusion injury is a vascular stroke. Yet another embodiment is when the peripheral neuropathy is caused by Guillain-Barre syndrome. Still another embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

The present invention also contemplates the use of a compound of the present invention in the preparation of a medicament for the treatment of any of the diseases and disorders in an animal described herein.

In another embodiment, the disease or disorder is a neurological disorder.

In another embodiment, the neurological disorder is selected from the group consisting of peripheral neuropathy caused by physical injury or disease state, traumatic brain injury, physical damage to the spinal cord, stroke associated with brain damage, focal ischemia, global ischemia, reperfusion injury, demyelinating disease and neurological disorder relating to neurodegeneration. Another embodiment is when the reperfusion injury is a vascular stroke. Yet another embodiment is when the peripheral neuropathy is caused by Guillain-Barre syndrome.

Still another embodiment is when the demyelinating disease is multiple sclerosis. Another embodiment is when the neurological disorder relating to neurodegeneration is selected from the group consisting of Alzheimer's Disease, Parkinson's Disease, and amyotrophic lateral sclerosis.

Further still, the methods of the invention can be used to treat cancer and to radiosensitize tumor cells. The term "cancer" is interpreted broadly. The compounds of the present invention can be "anti-cancer agents", which term also encompasses "anti-tumor cell growth agents" and "anti-neoplastic agents". For example, the methods of the invention are useful for treating cancers and radiosensitizing tumor cells in cancers such as ACTH-producing tumors, acute lymphocytic leukemia, acute nonlymphocytic leukemia, cancer of the adrenal cortex, bladder cancer, brain cancer, breast cancer, cervical cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer (small and/or non-small cell), malignant peritoneal effusion, malignant pleural effusion, melanoma, mesothelioma, multiple myeloma, neuroblastoma, non-Hodgkin's lymphoma, osteosarcoma, ovarian cancer, ovary (germ cell) cancer, prostate cancer, pancreatic cancer, penile cancer, retinoblastoma, skin cancer, soft-tissue sarcoma, squamous cell carcinomas, stomach cancer, testicular cancer, thyroid cancer, trophoblastic neoplasms, uterine cancer, vaginal cancer, cancer of the vulva and Wilm's tumor.

The methods of the present invention can also treat cancer in a mammal with an effective amount of temozolimide and a compound of the present invention. The cancer can be melanoma, lymphoma, and glioblastoma multiforme.

Radiosensitizers are known to increase the sensitivity of cancerous cells to the toxic effects of electromagnetic radiation. Several mechanisms for the mode of action of radiosensitizers have been suggested in the literature including: hypoxic cell radiosensitizers (e.g., 2-nitroimidazole compounds, and benzotriazine dioxide compounds) promote the reoxygenation of hypoxic tissue and/or catalyze the generation of damaging oxygen radicals; non-hypoxic cell radiosensitizers (e.g., halogenated pyrimidines) can be analogs of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers activated by the electromagnetic radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, NPe6, tin etioporphyrin SnET2, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumor with or without additional radiation; or other therapeutically effective compounds for treating cancer or other disease. Examples of additional therapeutic agents that may be used in conjunction with radiosensitizers include, but are not limited to: 5-fluorouracil, leucovorin, 5'-amino-5'deoxythymidine, oxygen, carbogen, red cell transfusions, perfluorocarbons (e.g., Fluosol-DA), 2,3-DPG, BW12C, calcium channel blockers, pentoxyfylline, antiangiogenesis compounds, hydralazine, and L-BSO. Examples of chemotherapeutic agents that may be used in conjunction with radiosensitizers include, but are not limited to: adriamycin, camptothecin, carboplatin, cisplatin, daunorubicin, docetaxel, doxorubicin, interferon (alpha, beta, gamma), interleukin 2, irinotecan, paclitaxel, topotecan, and therapeutically effective analogs and derivatives of the same.

The present invention also relates to a pharmaceutical composition comprising (i) a therapeutically effective amount of a compound of the present invention and (ii) a pharmaceutically acceptable carrier.

The above discussion relating to the preferred embodiments' utility and administration of the compounds of the present invention also applies to the pharmaceutical composition of the present invention.

The term "pharmaceutically acceptable carrier" as used herein refers to any carrier, diluent, excipient, suspending agent, lubricating agent, adjuvant, vehicle, delivery system, emulsifier, disintegrant, absorbent, preservative, surfactant, colorant, flavorant, or sweetener.

For these purposes, the composition of the invention may be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term parenteral as used herein includes subcutaneous, intravenous, intramuscular, intraperitoneal, intrathecal, intraventricular, intrasternal, and intracranial injection or infusion techniques.

When administered parenterally, the composition will normally be in a unit dosage, sterile injectable form (solution, suspension or emulsion) which is preferably isotonic with the blood of the recipient with a pharmaceutically acceptable carrier. Examples of such sterile injectable forms are sterile injectable aqueous or oleaginous suspensions. These suspensions may be formulated according to techniques known in the art using suitable dispersing or wetting agents and suspending agents. The sterile injectable forms may also be sterile injectable solutions or suspensions in non-toxic parenterally-acceptable diluents or solvents, for example, as solutions in 1,3-butanediol. Among the acceptable vehicles and solvents that may be employed are water, saline, Ringer's solution, dextrose solution, isotonic sodium chloride solution, and Hanks' solution. In addition, sterile, fixed oils are conventionally employed as solvents or suspending mediums. For this purpose, any bland fixed oil may be employed including synthetic mono- or di-glycerides, corn, cottonseed, peanut, and sesame oil. Fatty acids such as ethyl oleate, isopropyl myristate, and oleic acid and its glyceride derivatives, including olive oil and castor oil, especially in their polyoxyethylated versions, are useful in the preparation of injectables. These oil solutions or suspensions may also contain long-chain alcohol diluents or dispersants.

Sterile saline is a preferred carrier, and the compounds are often sufficiently water soluble to be made up as a solution for all foreseeable needs. The carrier may contain minor amounts of additives, such as substances that enhance solubility, isotonicity, and chemical stability, e.g., anti-oxidants, buffers and preservatives.

Formulations suitable for nasal or buccal administration (such as self-propelling powder dispensing formulations) may comprise about 0.1% to about 5% w/w, for example 1% w/w of active ingredient. The formulations for human medical use of the present invention comprise an active ingredient in association with a pharmaceutically acceptable carrier therefore and optionally other therapeutic ingredient(s).

When administered orally, the composition will usually be formulated into unit dosage forms such as tablets, cachets, powder, granules, beads, chewable lozenges, capsules, liquids, aqueous suspensions or solutions, or similar dosage forms, using conventional equipment and techniques known in the art. Such formulations typically include a solid, semi-solid, or liquid carrier. Exemplary carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propyl hydroxybenzoate, talc, magnesium stearate, and the like.

The composition of the invention can be administered as a capsule or tablet containing a single or divided dose of the inhibitor. The composition can also be administered as a sterile solution, suspension, or emulsion, in a single or divided dose. Tablets may contain carriers such as lactose and corn starch, and/or lubricating agents such as magnesium stearate. Capsules may contain diluents including lactose and dried corn starch.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active, or dispersing agent. Molded tablets may be made by molding in a suitable machine, a mixture of the powdered active ingredient and a suitable carrier moistened with an inert liquid diluent.

The compounds of this invention may also be administered rectally in the form of suppositories. These compositions can be prepared by mixing the drug with a suitable non-irritating excipient which is solid at room temperature, but liquid at rectal temperature, and, therefore, will melt in the rectum to release the drug. Such materials include cocoa butter, beeswax, and polyethylene glycols.

Compositions and methods of the invention also may utilize controlled release technology. Thus, for example, the inventive compounds may be incorporated into a hydrophobic polymer matrix for controlled release over a period of days. The composition of the invention may then be molded into a solid implant, or externally applied patch, suitable for providing efficacious concentrations of the PARP inhibitors over a prolonged period of time without the need for frequent re-dosing. Such controlled release films are well known to the art. Other embodiments are transdermal delivery systems. Other examples of polymers commonly employed for this purpose that may be used in the present invention include nondegradable ethylene-vinyl acetate copolymer an degradable lactic acid-glycolic acid copolymers which may be used externally or internally. Certain hydrogels such as poly(hydroxyethylmethacrylate) or poly(vinylalcohol) also may be useful, but for shorter release cycles than the other polymer release systems, such as those mentioned above.

In another embodiment, the carrier is a solid biodegradable polymer or mixture of biodegradable polymers with appropriate time release characteristics and release kinetics. The composition of the invention may then be molded into a solid implant suitable for providing efficacious concentrations of the compounds of the invention over a prolonged period of time without the need for frequent re-dosing. The composition of the present invention can be incorporated into the biodegradable polymer or polymer mixture in any suitable manner known to one of ordinary skill in the art and may form a homogeneous matrix with the biodegradable polymer, or may be encapsulated in some way within the polymer, or may be molded into a solid implant.

In one embodiment, the biodegradable polymer or polymer mixture is used to form a soft "depot" containing the pharmaceutical composition of the present invention that can be administered as a flowable liquid, for example, by injection, but which remains sufficiently viscous to maintain the pharmaceutical composition within the localized area around the injection site. The degradation time of the depot so formed can be varied from several days to a few years, depending upon the polymer selected and its molecular weight. By using a polymer composition in injectable form, even the need to make an incision may be eliminated. In any event, a flexible or flowable delivery "depot" will adjust to the shape of the space it occupies with the body with a minimum of trauma to surrounding tissues. The pharmaceutical composition of the present invention is used in amounts that are therapeutically effective, and may depend upon the desired release profile, the concentration of the pharmaceutical composition required for the sensitizing effect, and the length of time that the pharmaceutical composition has to be released for treatment.

The PARP inhibitors are used in the composition in amounts that are therapeutically effective. The compositions may be sterilized and/or contain adjuvants, such as preserving, stabilizing, welling, or emulsifying agents, solution promoters, salts for regulating the osmotic pressure, and/or buffers. In addition, they may also contain other therapeutically valuable substances. The compositions are prepared according to conventional mixing, granulating, or coating methods, and contain about 0.1 to 75% by weight, preferably about 1 to 50% by weight, of the active ingredient.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for administration to the brain.

Doses of the compounds include pharmaceutical dosage units comprising an efficacious quantity of active compound. By an efficacious quantity is meant a quantity sufficient to inhibit PARP and derive its beneficial effects through administration of one or more of the pharmaceutical dosage units. Also, the dose is sufficient to prevent or reduce the effects of vascular stroke or other neurodegenerative diseases.

For medical use, the amount required of the active ingredient to achieve a therapeutic effect will vary with the particular compound, the route of administration, the mammal under treatment, and the particular disorder or disease being treated. A suitable systematic dose of a compound of the present invention or a pharmacologically acceptable salt thereof for a mammal suffering from, or likely to suffer from, any of condition as described hereinbefore is in the range of about 0.1 mg/kg to about 100 mg/kg of the active ingredient compound, the dosage being about 1 to about 10 mg/kg.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

It is understood that the ordinarily skilled physician or veterinarian will readily determine and prescribe the effective amount of the compound for prophylactic or therapeutic treatment of the condition for which treatment is administered. In so proceeding, the physician or veterinarian could employ an intravenous bolus followed by an intravenous infusion and repeated administrations, parenterally or orally, as considered appropriate. While it is possible for an active ingredient to be administered alone, it is preferable to present it as a formulation.

When preparing dosage forms incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F. D. & C. dyes and lakes; flavorants; and sweeteners.

The present invention relates to the use of compounds of the present invention in the preparation of a medicament for the treatment of any disease or disorder in an animal described herein.

As used herein, "alkyl" means a branched or unbranched saturated hydrocarbon chain comprising a designated number of carbon atoms. For example, $C_1$-$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like, unless otherwise indicated.

"Alkenyl" means a branched or unbranched unsaturated hydrocarbon chain comprising a designated number of carbon atoms. For example, $C_2$-$C_6$ straight or branched alkenyl hydrocarbon chain contains 2 to 6 carbon atoms having at least one double bond, and includes but is not limited to substituents such as ethenyl, propenyl, isopropenyl, butenyl, iso-butenyl, tert-butenyl, n-pentenyl, n-hexenyl, and the like, unless otherwise indicated.

"Alkoxy", means the group —OR wherein R is alkyl as herein defined. R can also be a branched or unbranched saturated hydrocarbon chain containing 1 to 6 carbon atoms.

"Cyclo", used herein as a prefix, refers to a structure characterized by a closed ring.

"Halo" means at least one fluoro, chloro, bromo, or iodo moiety, unless otherwise indicated.

"Amino" compounds include amine ($NH_2$) as well as substituted amino.

"Ar", "aryl" or "heteroaryl" means a moiety which is substituted or unsubstituted, especially a cyclic or fused cyclic ring and includes a mono-, bi-, or tricyclic, carbo- or heterocyclic ring, wherein the ring is either unsubstituted or substituted in one to five position(s) with halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, and sulfonyl; wherein the individual ring sizes are 5-8 members; wherein the heterocyclic ring contains 1-4 heteroatom(s) selected from the group consisting of O, N, or S; wherein aromatic or tertiary alkyl amines are optionally oxidized to a corresponding N-oxide. Heteroaryls may be attached to other rings or substituted through the heteroatom and/or carbon atom of the ring. Aryl or heteroaryl moieties include but are not limited to phenyl, benzyl, naphthyl, pyrrolyl, pyrrolidinyl, pyridinyl, pyrimidinyl, purinyl, quinolinyl, isoquinolinyl, furyl, thiophenyl, imidazolyl, oxazolyl, thiazolyl, pyrazolyl, and thienyl.

"Phenyl" includes all possible isomeric phenyl radicals, optionally monosubstituted or multi-substituted with substituents selected from the group consisting of amino, trifluoromethyl, $C_1$-$C_6$ straight or branched chain alkyl, $C_2$-$C_6$ straight or branched chain alkenyl, carbonyl, thiocarbonyl, ester, thioester, alkoxy, alkenoxy, cyano, nitro, imino, alkylamino, aminoalkyl, sulfhydryl, thioalkyl, sulfonyl, hydroxy, halo, haloalkyl, $NR_2$ wherein $R_2$ is selected from the group consisting of hydrogen, ($C_1$-$C_6$)-straight or branched chain alkyl, ($C_3$-$C_6$) straight or branched chain alkenyl or alkynyl, and ($C_1$-$C_4$) bridging alkyl wherein said bridging alkyl forms a heterocyclic ring starting with the nitrogen of $NR_1$ and ending with one of the carbon atoms of said alkyl or alkenyl chain, and wherein said heterocyclic ring is optionally fused to an Ar group.

Cycloalkyl optionally containing at least one heteroatom includes saturated $C_3$-$C_8$ rings, such as $C_5$ or $C_6$ rings, wherein at 1-4 heteroatoms selected from O, N or S may be optionally substituted for a carbon atom of the ring. Cycloalkyls optionally containing at least one heteroatom, as described above, may be substituted by or fused to at least one 5 or 6 membered aryl or heteroaryl. Other cycloalkyls containing a heteroatom include pyrrolidinyl, imidazolidinyl, pyrazolidinyl, piperidinyl, piperazinyl, morpholino and thiomorpholino.

The compounds of the present invention possess one or more asymmetric center(s) and thus can be produced as mixtures (racemic and non-racemic) of stereoisomers, or as individual enantiomers or diastereomers. The individual stereoisomers may be obtained by using an optically active starting material, by resolving a racemic or non-racemic mixture of an intermediate at some appropriate stage of the synthesis, or by resolution of the compound of the present invention. It is understood that the individual stereoisomers as well as mixtures (racemic and non-racemic) of stereoisomers are encompassed by the scope of the present invention.

"Isomers" are different compounds that have the same molecular formula and includes cyclic isomers such as (iso) indole and other isomeric forms of cyclic moieties. "Stereoisomers" are isomers that differ only in the way the atoms are arranged in space. "Enantiomers" are a pair of stereoisomers that are non-superimposable mirror images of each other. "Diastereoisomers" are stereoisomers which are not mirror images of each other. "Racemic mixture" means a mixture containing equal parts of individual enantiomers. "Non-racemic mixture" is a mixture containing unequal parts of individual enantiomers or stereoisomers.

The compounds of the invention are useful in a free base form, in the form of pharmaceutically acceptable salts, pharmaceutically acceptable hydrates, pharmaceutically acceptable esters, pharmaceutically acceptable solvates, pharmaceutically acceptable prodrugs, pharmaceutically acceptable metabolites, and in the form of pharmaceutically acceptable stereoisomers. These forms are all within the scope of the invention. In practice, the use of these forms amounts to use of the neutral compound.

"Pharmaceutically acceptable salt", "hydrate", "ester" or "solvate" refers to a salt, hydrate, ester, or solvate of the inventive compounds which possesses the desired pharmacological activity and which is neither biologically nor otherwise undesirable. Organic acids can be used to produce salts, hydrates, esters, or solvates such as acetate, adipate, alginate, aspartate, benzoate, benzenesulfonate, p-toluenesulfonate, bisulfate, sulfamate, sulfate, naphthylate, butyrate, citrate, camphorate, camphorsulfonate, cyclopentane-propionate, digluconate, dodecylsulfate, ethanesulfonate, fumarate, glucoheptanoate, glycerophosphate, hemisulfate heptanoate, hexanoate, 2-hydroxyethanesulfonate, lactate, maleate, methanesulfonate, 2-naphthalenesulfonate, nicotinate, oxalate, tosylate and undecanoate. Inorganic acids can be used to produce salts, hydrates, esters, or solvates such as hydrochloride, hydrobromide, hydroiodide, and thiocyanate.

Examples of suitable base salts, hydrates, esters, or solvates include hydroxides, carbonates, and bicarbonates of ammonia, alkali metal salts such as sodium, lithium and potassium salts, alkaline earth metal salts such as calcium and magnesium salts, aluminum salts, and zinc salts.

Salts, hydrates, esters, or solvates may also be formed with organic bases. Organic bases suitable for the formation of pharmaceutically acceptable base addition salts, hydrates, esters, or solvates of the compounds of the present invention include those that are non-toxic and strong enough to form such salts, hydrates, esters, or solvates. For purposes of illustration, the class of such organic bases may include mono-, di-, and trialkylamines, such as methylamine, dimethylamine, triethylamine and dicyclohexylamine; mono-, di- or trihydroxyalkylamines, such as mono-, di-, and triethanolamine; amino acids, such as arginine and lysine; guanidine; N-methyl-glucosamine; N-methyl-glucamine; L-glutamine; N-methyl-piperazine; morpholine; ethylenediamine; N-benzyl-phenethylamine; (trihydroxy-methyl)aminoethane; and the like. See, for example, "Pharmaceutical Salts," J. Pharm. Sci., 66:1, 1-19 (1977). Accordingly, basic nitrogen-containing groups can be quaternized with agents including: lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as benzyl and phenethyl bromides.

The acid addition salts, hydrates, esters, or solvates of the basic compounds may be prepared either by dissolving the free base of a PARP inhibitor of the present invention in an aqueous or an aqueous alcohol solution or other suitable solvent containing the appropriate acid or base, and isolating the salt by evaporating the solution. Alternatively, the free base of the PARP inhibitor of the present invention can be reacted with an acid, as well as reacting the PARP inhibitor having an acid group thereon with a base, such that the reactions are in an organic solvent, in which case the salt separates directly or can be obtained by concentrating the solution.

"Pharmaceutically acceptable prodrug" refers to a derivative of the inventive compounds which undergoes biotransformation prior to exhibiting its pharmacological effect(s). The prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the inventive compounds using methods known in the art, such as those described by Burger's Medicinal Chemistry and Drug Chemistry, Fifth Ed., Vol. 1, pp. 172-178, 949-982 (1995). For example, the inventive compounds can be transformed into prodrugs by converting one or more of the hydroxy or carboxy groups into esters.

"Pharmaceutically acceptable metabolite" refers to drugs that have undergone a metabolic transformation. After entry into the body, most drugs are substrates for chemical reactions that may change their physical properties and biologic effects. These metabolic conversions, which usually affect the polarity of the compound, alter the way in which drugs are distributed in and excreted from the body. However, in some cases, metabolism of a drug is required for therapeutic effect. For example, anticancer drugs of the antimetabolite class must be converted to their active forms after they have been transported into a cancer cell. Since most drugs undergo metabolic transformation of some kind, the biochemical reactions that play a role in drug metabolism may be numerous and diverse. The main site of drug metabolism is the liver, although other tissues may also participate.

The term "neurodegenerative diseases" includes, but is not limited to Alzheimer's disease, Parkinson's disease and Huntington's disease.

The term "nervous insult" refers to any damage to nervous tissue and any disability or death resulting therefrom. The cause of nervous insult may be metabolic, toxic, neurotoxic, iatrogenic, thermal or chemical, and includes without limitation, ischemia, hypoxia, cerebrovascular accident, trauma, surgery, pressure, mass effect, hemmorrhage, radiation, vasospasm, neurodegenerative disease, infection, Parkinson's disease, amyotrophic lateral sclerosis (ALS), myelination/demyelination process, epilepsy, cognitive disorder, glutamate abnormality and secondary effects thereof.

The term "neuroprotective" refers to the effect of reducing, arresting or ameliorating nervous insult, and protecting, resuscitating, or reviving nervous tissue that has suffered nervous insult.

The term "preventing neurodegeneration" includes the ability to prevent a neurodegenerative disease or preventing further neurodegeneration in patients who are already suffering from or have symptoms of a neurodegenerative disease.

The term "treating" refers to:

(i) preventing a disease, disorder or condition from occurring in an animal that may be predisposed to the disease, disorder and/or condition, but has not yet been diagnosed as having it;

(ii) inhibiting the disease, disorder or condition, i.e., arresting its development; and (iii) relieving the disease, disorder or condition, i.e., causing regression of the disease, disorder and/or condition.

The term "neural tissue damage resulting from ischemia and reperfusion injury and neurodegenerative diseases" includes damage due to neurotoxicity, such as seen in vascular stroke and global and focal ischemia.

The term "ischemia" relates to localized tissue anemia due to obstruction of the inflow of arterial blood. Global ischemia occurs under conditions in which blood flow to the entire brain ceases for a period of time, such as may result from cardiac arrest. Focal ischemia occurs under conditions in which a portion of the brain is deprived of its normal blood supply, such as may result from thromboembolytic occlusion of a cerebral vessel, traumatic head injury, edema, and brain tumors.

The term "cardiovascular disease" relates to myocardial infarction, angina pectoris, vascular or myocardial ischemia, and related conditions as would be known by those of skill in the art which involve dysfunction of or tissue damage to the heart or vasculature, and especially, but not limited to, tissue damage related to PARP activation.

The term "radiosensitizer", as used herein, is defined as a molecule, such as a low molecular weight molecule, administered to animals in therapeutically effective amounts to increase the sensitivity of the cells to be radiosensitized to electromagnetic radiation and/or to promote the treatment of diseases which are treatable with electromagnetic radiation. Diseases which are treatable with electromagnetic radiation include neoplastic diseases, benign and malignant tumors, and cancerous cells. Electromagnetic radiation treatment of other diseases not listed herein are also contemplated by the present invention. The terms "electromagnetic radiation" and "radiation" as used herein includes, but is not limited to, radiation having the wavelength of $10^{-20}$ to $10^0$ meters. Preferred embodiments of the present invention employ the electromagnetic radiation of: gamma-radiation ($10^{-20}$ to $10^{-13}$ m) x-ray radiation ($10^{-11}$ to $10^{-9}$ m), ultraviolet light (10 nm to 400 nm), visible light (400 nm to 700 nm), infrared radiation (700 nm to 1.0 mm), or microwave radiation (1 mm to 30 cm).

Many of the PARP inhibitors can be synthesized by known methods from starting materials that are known, may be available commercially, or may be prepared by methods used to prepare corresponding compounds in the literature. See, for example, Suto et al., "Dihydroiso-quinolinones: The Design and Synthesis of a New Series of Potent Inhibitors of Poly (ADP-ribose) Polymerase", Anticancer Drug Des., 6:107-17 (1991), which discloses processes for synthesizing a number of different PARP inhibitors.

The quinazoline-one and phthalazin-one derivatives of this invention are represented by previously defined formulas I and II. As an example, the derivatives of this invention can be prepared in a conventional manner as illustrated below by Schemes 1-8. The rings on the quinazoline-one and phthalazin-one derivatives may be generically substituted as set forth in formula I and II. Such starting derivatives are known in the chemistry literature and accessible by processes known to one skilled in the art.

The diazabenzo[de]anthracen-3-one derivatives of this invention can be prepared in a conventional manner as illustrated below by Schemes 9-11.

Scheme 2

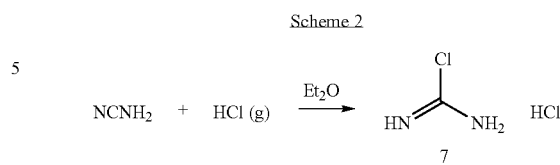

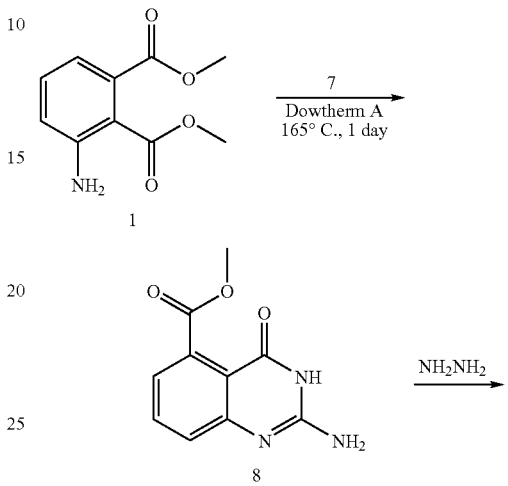

Scheme 1

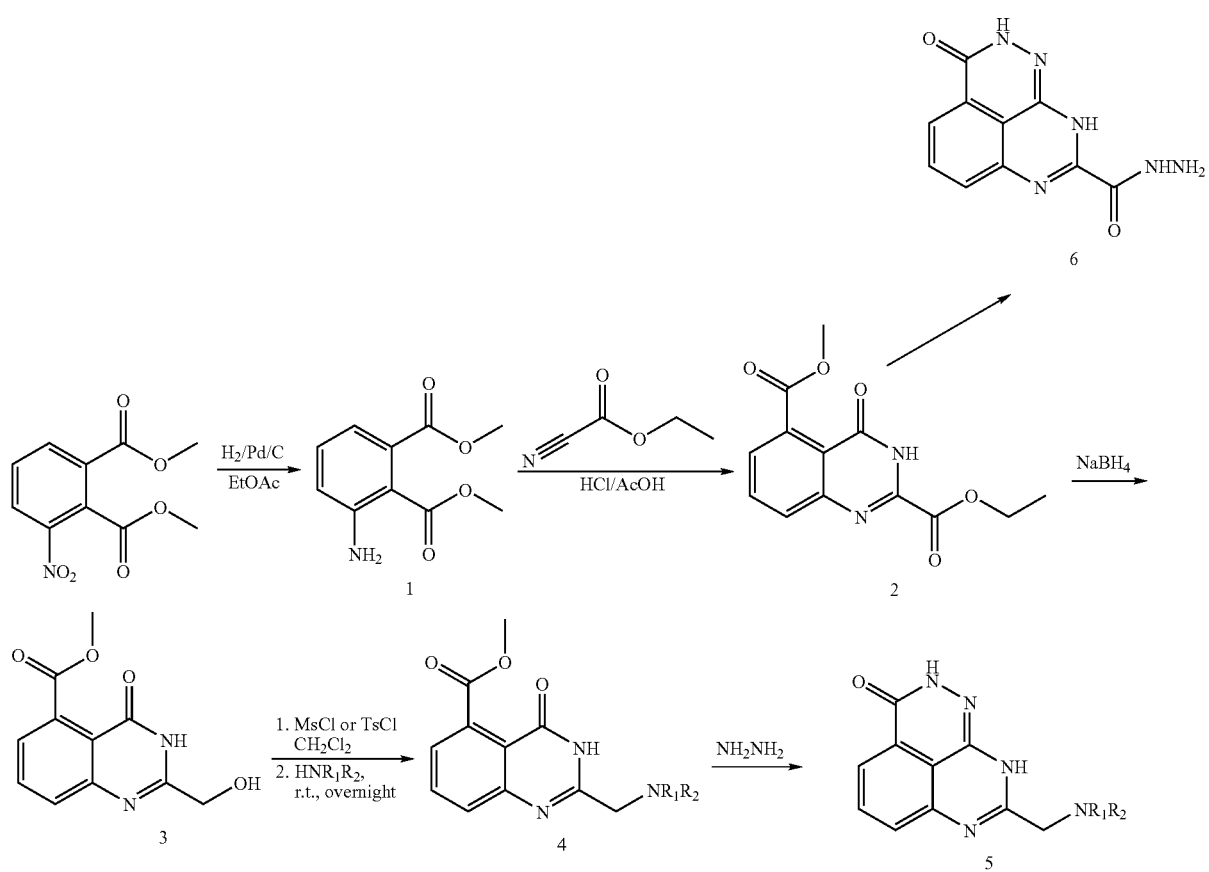

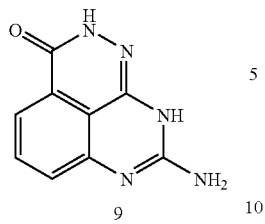
9
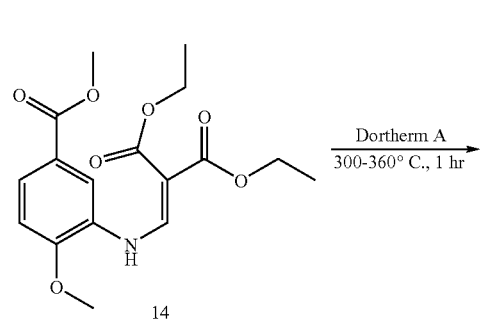
Scheme 3
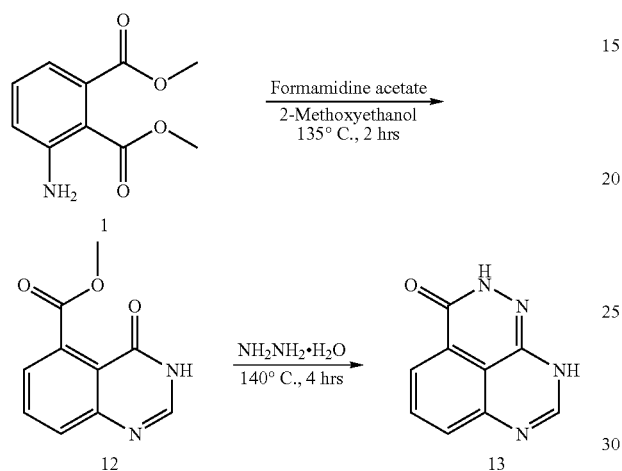
Scheme 4
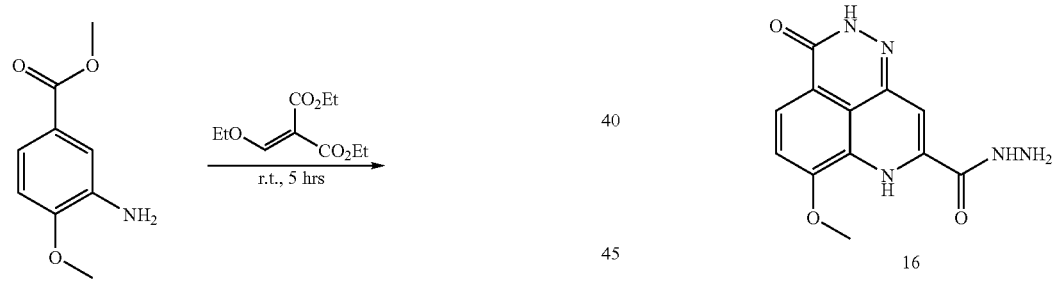
Scheme 5
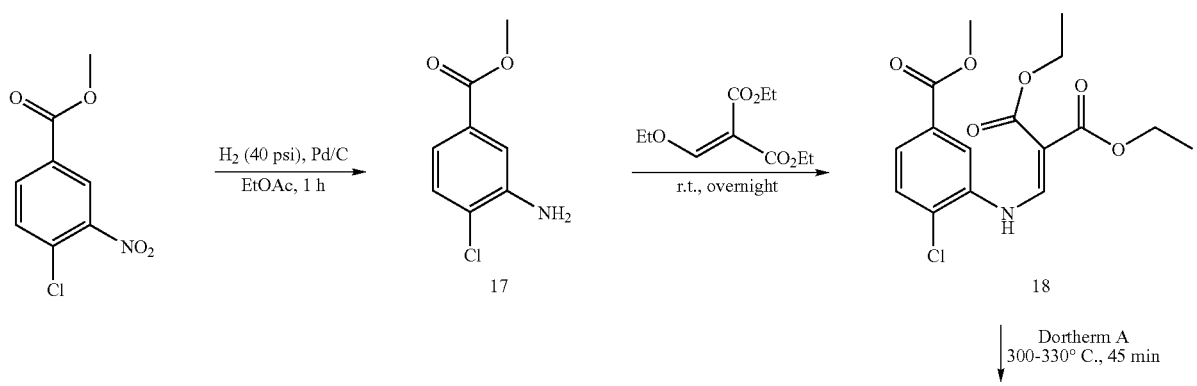

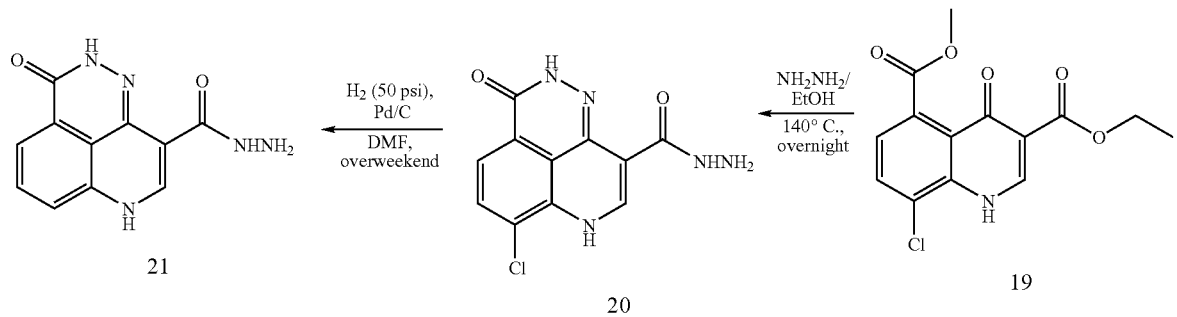
Scheme 6
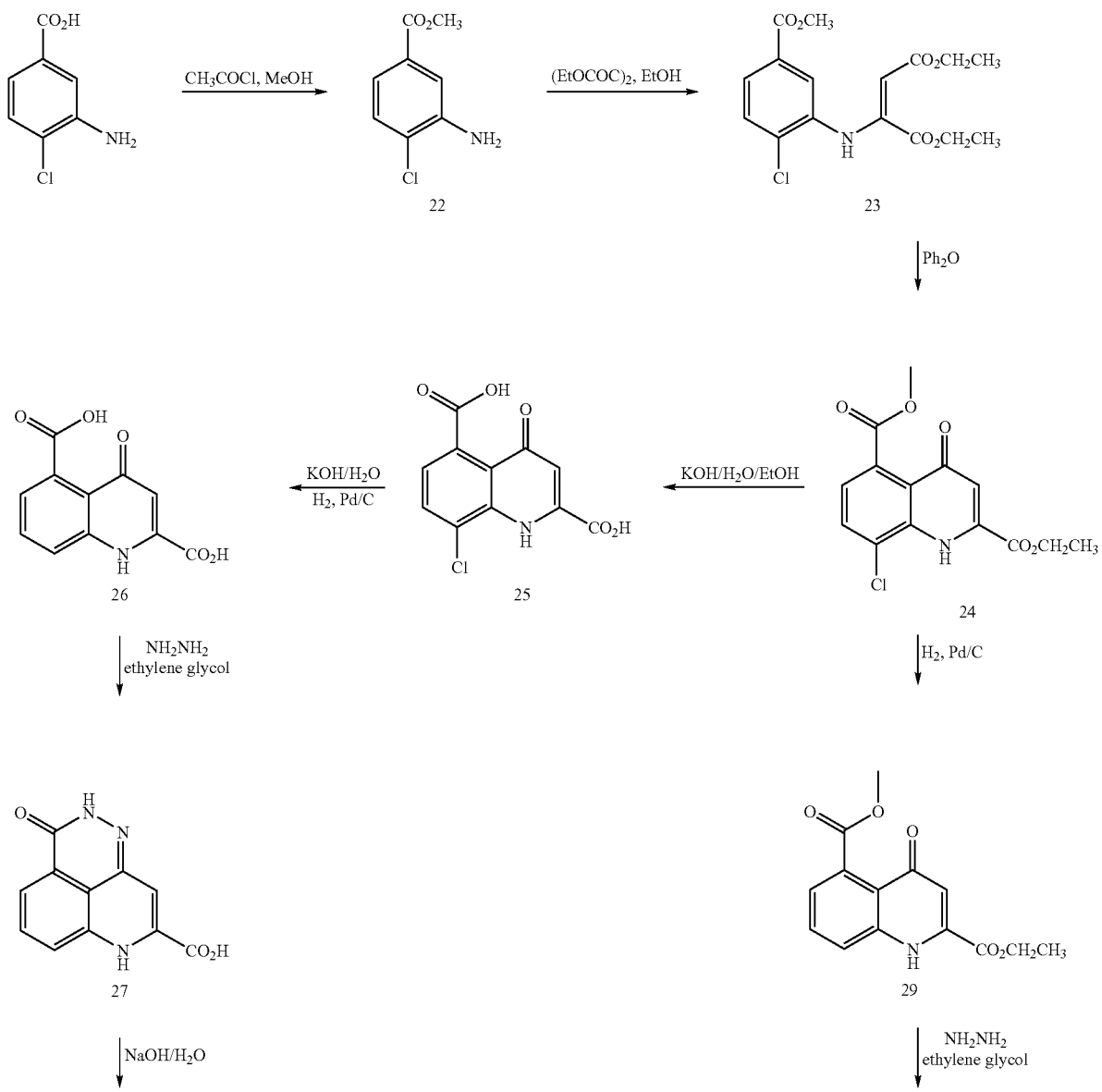

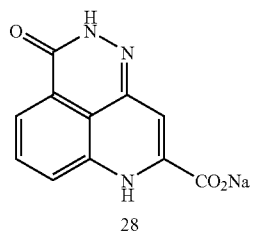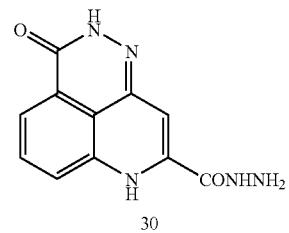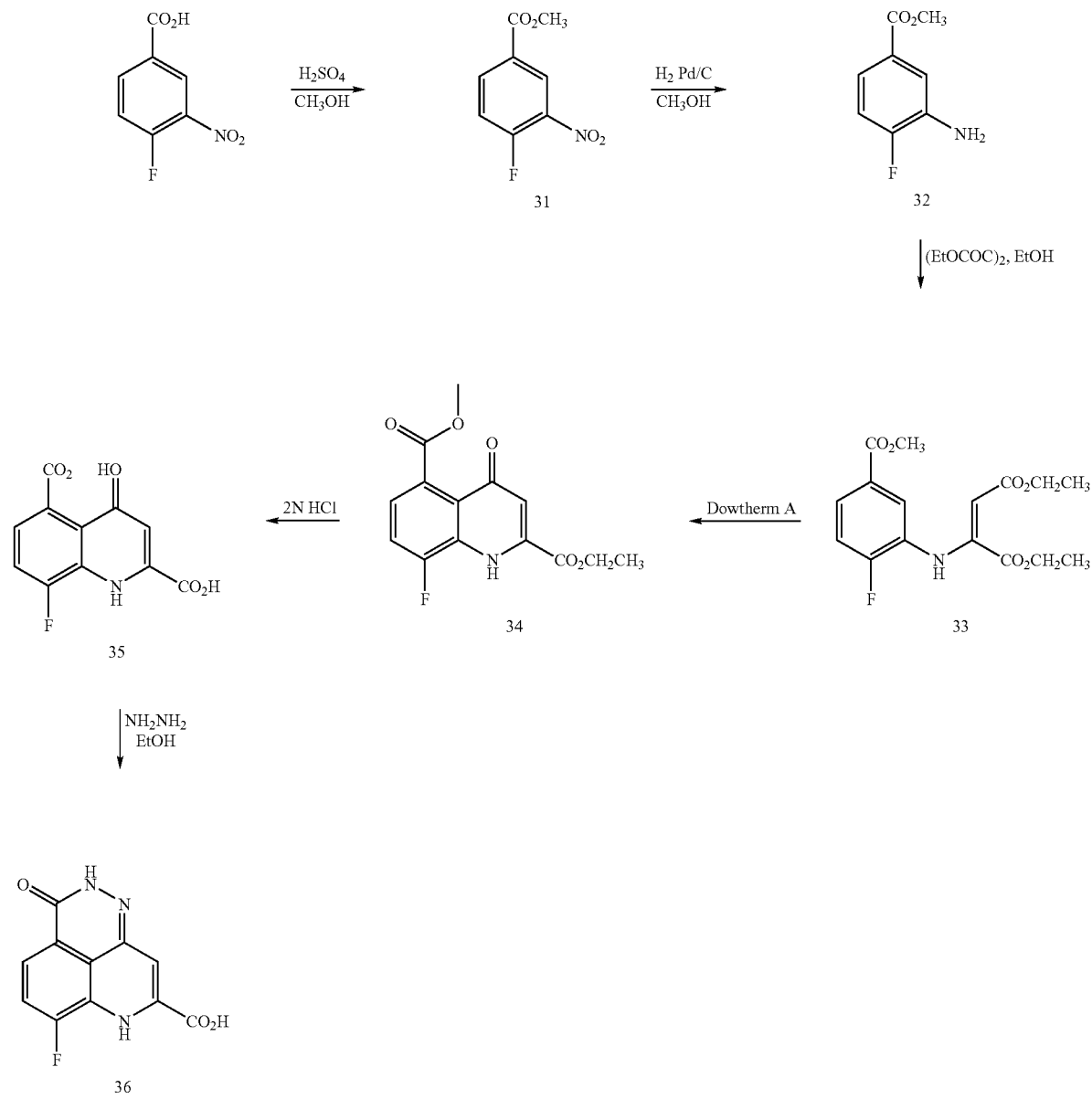

Scheme 8
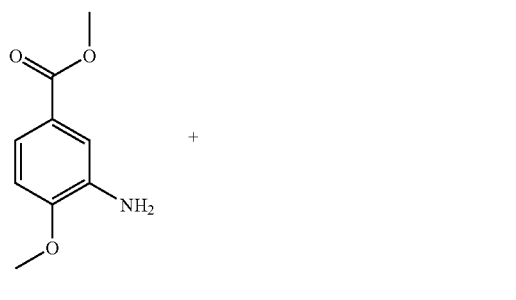
Scheme 9
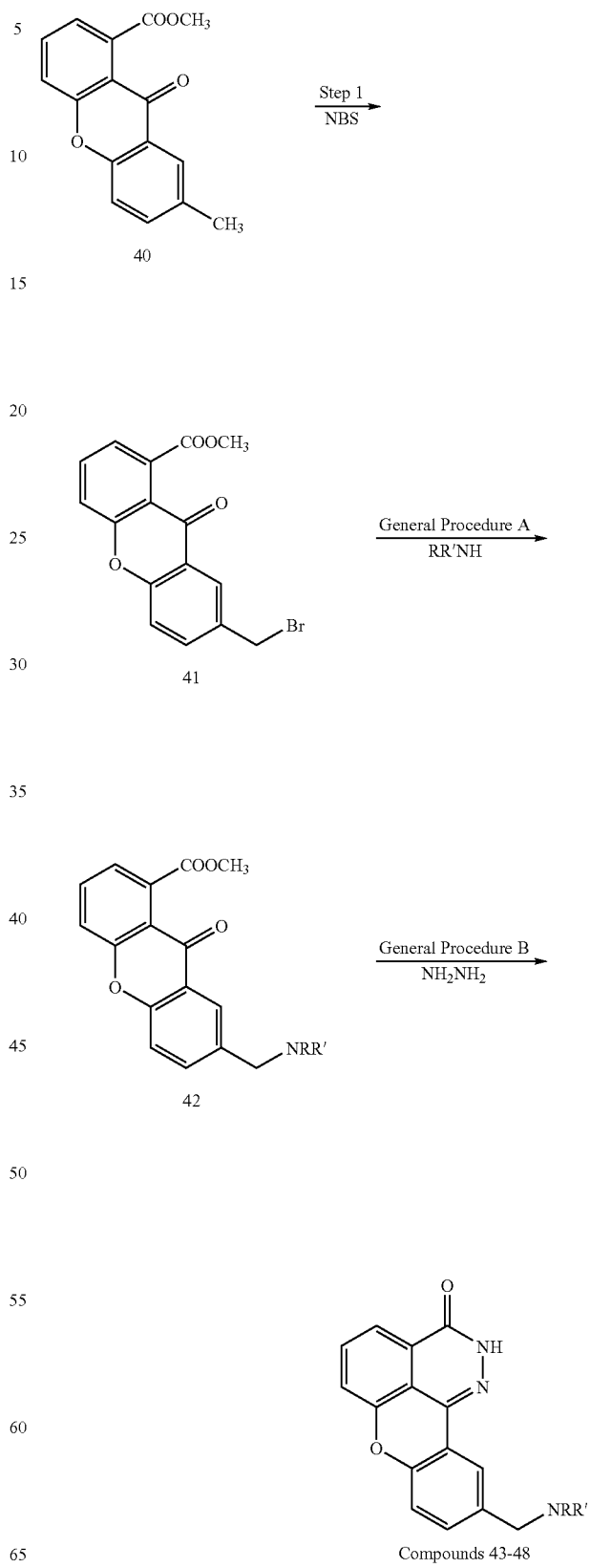

Scheme 10
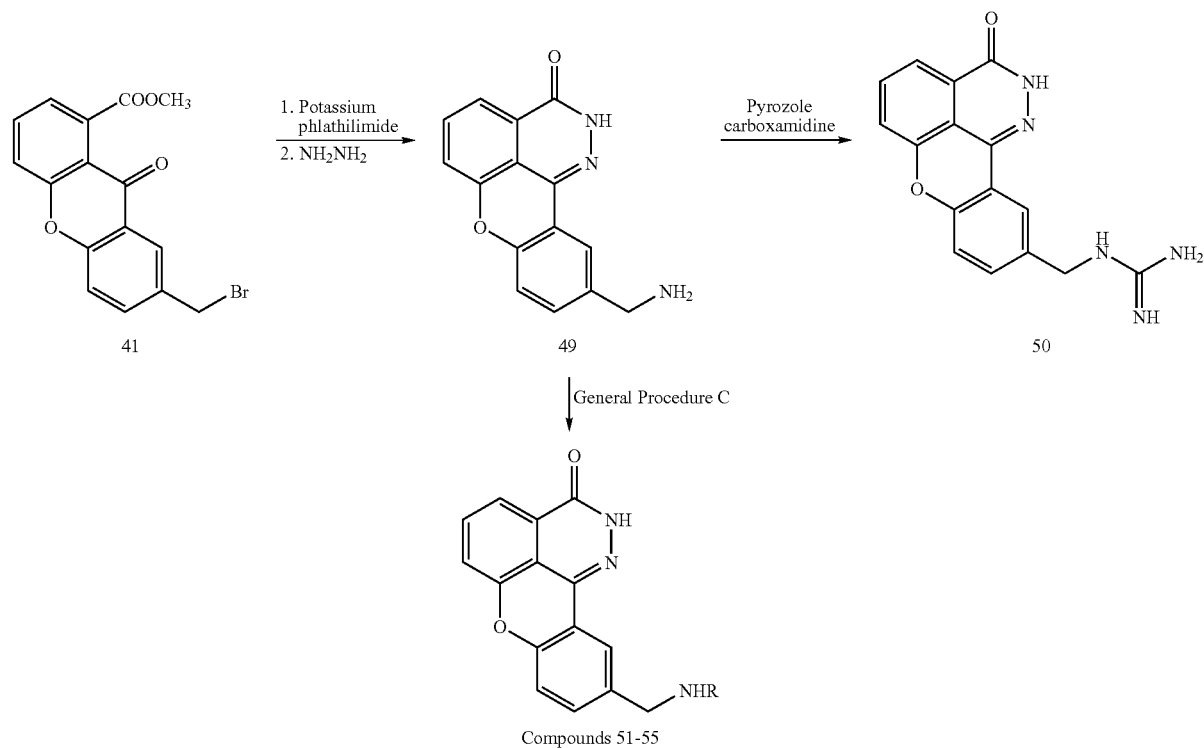
Scheme 11
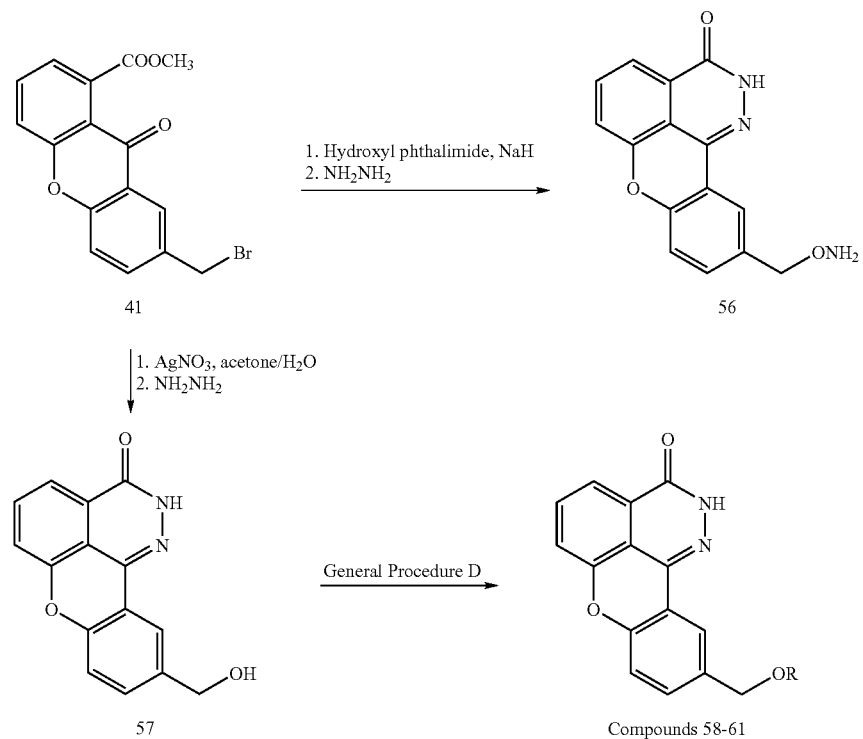

Other manners, variations or sequences of preparing the compounds of the present invention will be readily apparent to those skilled in the art.

The compounds of the present invention may be useful in the free base form, in the form of base salts where possible, and in the form of addition salts, as well as in the free acid form. All these forms are within the scope of this invention. In practice, use of the salt form amounts to use of the base form. Pharmaceutically acceptable salts within the scope of this invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfonate, ethanesulfonate, benzenesulfonate, p-toluenesulfonate, and the like respectively, or those derived from bases such as suitable organic and inorganic bases. Examples of pharmaceutically acceptable base addition salts with compounds of the present invention include organic bases which are nontoxic and strong enough to form such salts. These organic bases and the use thereof are readily understood by those skilled in the art. Merely for the purpose of illustration, such organic bases may include mono-, di-, and trialkylamines, such as methylamine, diethylamine and triethylamine; mono-, di-, or trihydroxyalkylamines such as mono-, di-, and triethanolamine; amino acids such as arginine, and lysine; guanidine; N-methylglucosamine; N-methylgiucamine; L-glutamine; N-methylpiperazine; morpholine; ethylenedianane; N-benzylphenethylamine; tris(hydroxymethyl)antinoethane; and the like.

The acid addition salts of the basic compounds may be prepared by dissolving the free base of the compound of the present invention in aqueous or aqueous alcohol solution or other suitable solvents containing the appropriate acid or base and isolating the salt by evaporating the solution, or by reacting the free base of the compound of the present invention with an acid as well as reacting the compound of the present invention having an acid group thereon with a base such that the reactions are in an organic solvent, in which case the salt separates directly or can be obtained by concentration of the solution.

The compounds of this invention contain one or more asymmetric carbon atoms. Therefore, the invention includes the individual stereoisomers and mixtures thereof as well as the racemic compounds. The individual isomers may be prepared or isolated by methods known in the art.

The compounds of the invention exhibit pharmacological activity and are, therefore, useful as pharmaceuticals. Additionally, the compounds exhibit central nervous and cardiac vesicular system activity.

PARP Assays $IC_{50}$

A convenient method to determine $IC_{50}$ of a PARP inhibitor compound is a PARP assay using purified recombinant human PARP from Trevigan (Gaithersburg, Md.), as follows: The PARP enzyme assay is set up on ice in a volume of 100 microliters consisting of 100 mM Tris-HCl (pH 8.0), 1 mM $MgCl_2$, 28 mM KCl, 28 mM NaCl, 0.1 mg/ml of DNase I activated herring sperm DNA (Sigma, Mo.), 3.0 micromolar [3H]nicotinamide adenine dinucleotide (470 mci/mmole), 7 micrograms/ml PARP enzyme, and various concentrations of the compounds to be tested. The reaction is initiated by incubating the mixture at 25° C. After 15 minutes of incubation, the reaction is terminated by adding 500 microliters of ice cold 20% (w/v) trichloroacetic acid. The precipitate formed is transferred onto a glass fiber filter (Packard Unifilter-GF/B) and washed three times with ethanol. After the filter is dried, the radioactivity is determined by scintillation counting. The compounds of this invention were found to have potent enzymatic activity in the range of a few nM to 20 μM in $IC_{50}$ in this inhibition assay.

$EC_{50}$

We used a $H_2O_2$ induced cell death assay to determine the cytoprotective effect of PARP inhibitors. P388D1 cells (CCL-46, ATCC), derived from a murine macrophage-like tumor, were maintained in Dulbeco's Modified Eagle Medium (DMEM) with 10% horse serum and 2 mM L-glutamine. The cytotoxicity assay was set up in a 96-well plate. In each well, 190 ul cells were seeded at $2 \times 10^6$/ml density. To determine the $EC_{50}$, the concentration of a compound required to achieve 50% reduction of cell death, a dose response experiment was conducted. PARP inhibitors were added to the media to a final concentration of 0.01, 0.03, 0.1, 0.3, 1, 3, 10, 30 uM. After 15 min incubation with a PARP inhibitor, 5 ul of freshly prepared $H_2O_2$ were added to the cells to a final concentration of 2 mM. Cells were returned to 37° C. incubator for 4 h. At the end of incubation, 25 ul of supernatant were sampled from the cell media to determine the level of lactate dehydrogenase (LDH) released from dead cells. The LDH activity was determined by monitoring the rate of decrease of NADH absorbency at 340 nm. The group without drug treatment was used to calculate total cell death due to $H_2O_2$ treatment. Each data point was an average of quadruplicate. The $EC_{50}$ was determined from a dose response curve.

Using the PARP assays described above, approximate $IC_{50}$ and $EC_{50}$ values were obtained for the following compounds:

TABLE I

| Structure | IC50 (μM) | EC50 (μM) |
|---|---|---|
| (quinoline with 5-C(O)NH-N, 3-C(O)-NHN, 8-OMe) | 20 | |
| (quinoline with 5-C(O)NH-NH, 2-C(O)-NHN, 8-OMe) | 20 | |
| (quinoline with 5-C(O)NH-N, 3-C(O)-NHN, 8-Cl) | 0.749 | |

TABLE I-continued

| Structure | IC50 (μM) | EC50 (μM) |
|---|---|---|
| (structure) | 0.039 | 0.35 |
| (structure) | 0.014 | 0.1 |
| (structure) | 2.79 | |
| (structure) | 0.026 | 0.51 |
| (structure) | 0.16 | 1.7 |
| (structure) | 0.091 | 0.64 |
| (structure) | 0.021 | 0.24 |

TABLE I-continued

| Structure | IC50 (μM) | EC50 (μM) |
|---|---|---|
| (structure) | 0.12 | |
| (structure) | 0.026 | 0.36 |
| (structure) | 0.087 | 0.01 |
| (structure) | 0.019 | 0.13 |
| (structure) | 0.019 | 0.12 |
| (structure) | 0.018 | |

TABLE I-continued
| Structure | IC50 (μM) | EC50 (μM) |
|---|---|---|
| 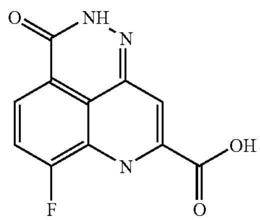 | 20 | |
| 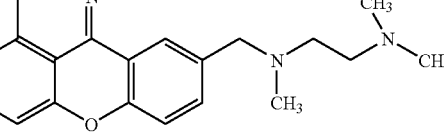 | 0.018 | |
TABLE II
| Structure | IC50 (μM) | EC50 (μM) |
|---|---|---|
| 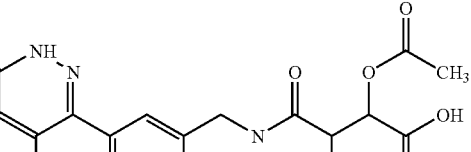<br>10-{[(2-Dimethylamino-ethyl)-methyl-amino]-methyl}-2H-7-oxa-1,2-diaza-benzo[de]anthracen-3-one | 0.1 | 0.17 |
| 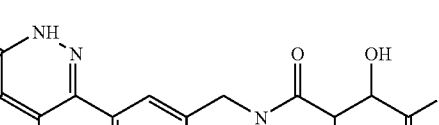 | 0.035 | 2.08 |
| 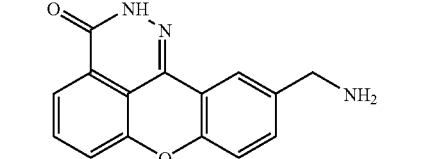 | 0.021 | 5.27 |
| 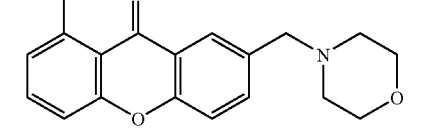 | 0.019 | 2.08 |
| 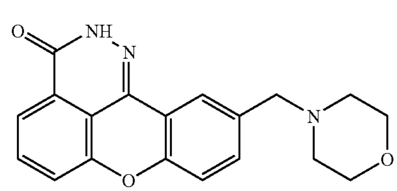 | 0.067 | 0.3 |

TABLE II-continued
| Structure | IC50 (μM) | EC50 (μM) |
|---|---|---|
| 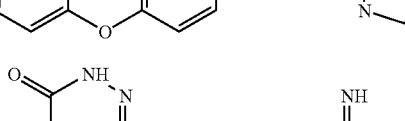 | 0.03 | 0.08 |
| 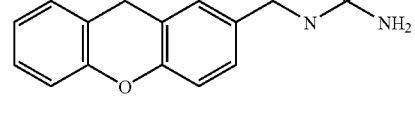 | 0.035 | 1 |
| 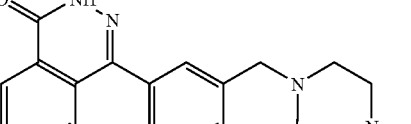 | 0.074 | 0.13 |
| 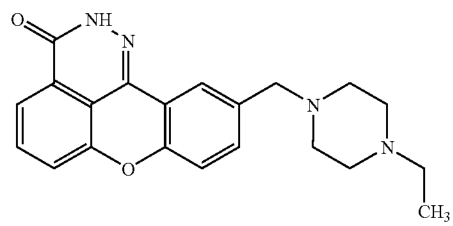 | 0.06 | 0.12 |
| 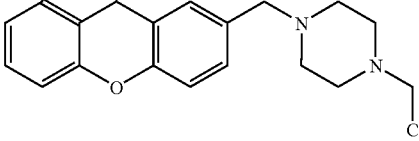 | 0.101 | 0.08 |
| 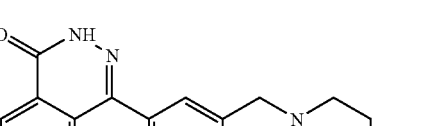 | 0.128 | 0.075 |
| 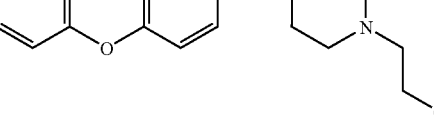 | 0.165 | 0.47 |

TABLE II-continued

| Structure | IC50 (μM) | EC50 (μM) |
|---|---|---|
| (structure) | 0.092 | 0.41 |
| (structure) | 0.038 | |
| (structure) | 0.413 | |
| (structure) | 0.125 | |
| (structure) | 0.086 | 0.52 |
| (structure) | 0.177 | |

TABLE II-continued

| Structure | IC50 (μM) | EC50 (μM) |
|---|---|---|
| 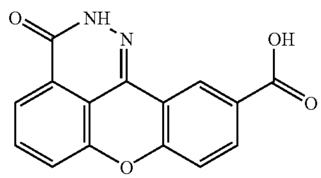 | 0.167 | |
| 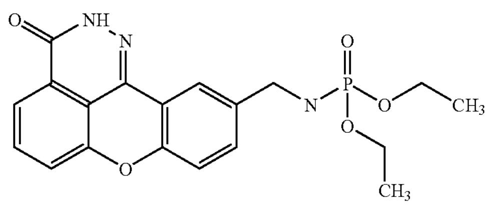 | 0.275 | |
| 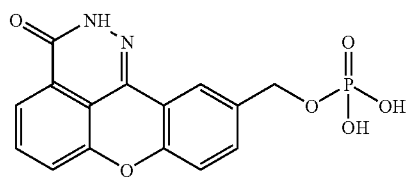 | 0.034 | 0.75 |
| 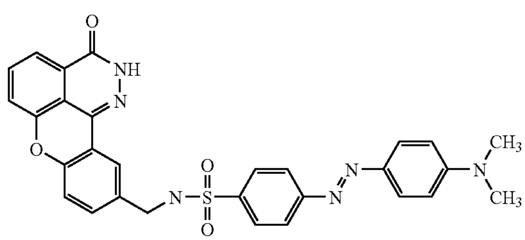 | 1.3 | |
| 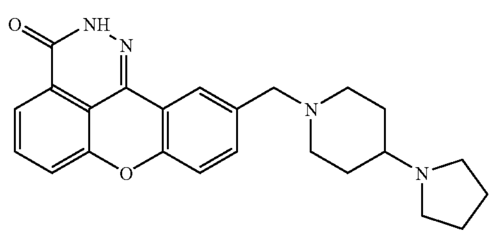 | 0.244 | |
| 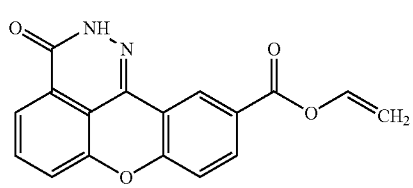 | 0.089 | |
| 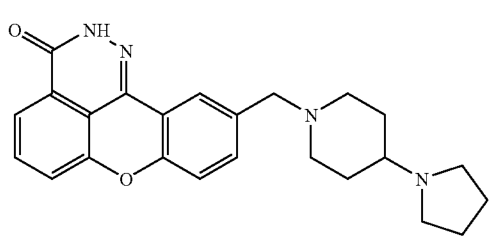 | 0.036 | 0.3 |

TABLE II-continued

| Structure | IC50 (μM) | EC50 (μM) |
|---|---|---|
| 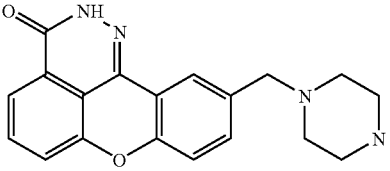 | 0.048 | 0.27 |

EXAMPLE 1

Preparation of Quinazoline Derivatives (5a, 5b, 5c, and 6) (Scheme 1)

Dimethyl 3-aminophthalate (1) To a solution of dimethyl 3-nitrophthalate (12 g, 50 mmol) in EtOAc (200 mL) was added 10% Pd/C (3 g). The resulting mixture was hydrogenated under $H_2$ (50 psi) on a Parr hydrogenation apparatus at room temperature overnight. The catalyst was filtered off on a pad of celite and the filtrate was concentrated in vacuum to afford a yellow oil (1, 10.5 g, 100%). $^1$H NMR (CDCl$_3$, 400 MHz) δ 7.16 (t, J=7.4, 8.2 Hz, 1H), 6.82 (dd, J=1.0, 7.4 Hz, 1H), 6.70 (dd, J=1.1, 8.4 Hz, 1H), 5.14 (br s, 2H), 3.78 (s, 3H), 3.76 (s, 3H).

2-Ethyl 5-methyl 4-oxo-3,4-dihydroquinazoline-2,5-dicarboxylate (2) A mixture of 1 (2.1 g, 10 mmol) in acetic acid (10 mL), ethyl cyanoformate (1.0 g, 10 mmol), and 1 N HCl in acetic acid (10.5 mL) was heated to 120° C. and stirred for 2.5 h. The reaction mixture was concentrated and the crude residue was purified by flash chromatography (0.5% MeOH in CH$_2$Cl$_2$ to 1% MeOH in CH$_2$Cl$_2$) to afford a white solid (2, 2.35 g, 85%). $^1$H NMR (DMSO-d$_6$, 400 MHz) δ 7.91 (d, J=4.2 Hz, 2H), 7.59 (t, J=4.2 Hz, 1H), 4.38 (q, J=7.1, 7.3, 14 Hz, 2H), 3.83 (s, 3H), 1.35 (t, J=7.3, 7.1 Hz, 3H).

5-Methyl 2-hydroxymethyl-4-oxo-3,4-dihydroquinazoline-5-carboxylate (3) To a solution of 2 (2.0 g, 7.25 mmol) in EtOH (100 mL) was added NaBH$_4$ (0.55 g, large excess) at 0° C. The resulting mixture was allowed to warm to room temperature and stirred for 6 h. The solvent was removed and EtOAc (50 mL) and H$_2$O (20 mL) were added. The aqueous layer was extracted with EtOAc and CH$_2$Cl$_2$. The combined organic layers were dried (MgSO$_4$) and concentrated in vacuum. The crude residue was purified by flash chromatography (1% MeOH in CH$_2$Cl$_2$ to 5% MeOH in CH$_2$Cl$_2$) to afford a white solid (3, 1.0 g, 59%). $^1$H NMR (CD$_3$OD, 400 MHz) δ 7.72 (t, J=7.4, 8.2 Hz, 1H), 7.64 (d, J=8.4 Hz, 1H), 7.32 (d, J=7.1 Hz, 1H), 4.46 (s, 2H), 3.82 (s, 3H).

5-Methyl 3,4-dihydro-4-oxo-2-(dimethylamino)methyl-5-quinazoline-carboxylate (4a) To a suspension of 3 (130 mg, 0.55 mmol) in CH$_2$Cl$_2$ (5 mL) at room temperature was added methanesulfonyl chloride (47 uL, 0.61 mmol) under N$_2$. The reaction mixture was stirred overnight followed by addition of dimethylamine hydrochloride (68 mg, 0.83 mmol) and Et$_3$N (168 mg, 1.67 mmol) at room temperature. The resulting mixture was stirred overnight. The reaction mixture was concentrated in vacuum and purified by flash chromatography (1% MeOH in CH$_2$Cl$_2$ to 2.5% MeOH in CH$_2$Cl$_2$) to afford a white solid (4a, 70 mg, 48%). $^1$H NMR (CDCl$_3$, 400 MHz) δ 7.63-7.75 (m, 2H), 7.36 (dd, J=1.9, 6.5 Hz, 1H), 3.94 (s, 3H), 3.46 (s, 2H), 2.31 (s, 3H).

5-Methyl 3,4-dihydro-4-oxo-2-(1-piperidinylmethyl)-5-quinazolinecarboxy-late (4b) To a solution of 3 (125 mg, 0.53 mmol) in CH$_2$Cl$_2$ (8 mL) was added Et$_3$N (81 mg, 0.80 mmol) and p-toluenesulfonyl chloride (826 mg, 0.59 mmol) at 0° C. The reaction mixture was allowed to warm to room temperature and stirred for 2 h. The solvents were removed in vacuum. To the resulting oil was added EtOH (5 mL) and piperidine (54 mg, 0.64 mmol) at room temperature. The reaction mixture was heated at 50° C. for 1.5 h and then cooled to room temperature. The solvent was removed in vacuum. EtOAc (40 mL) and H$_2$O (25 mL) were added and the aqueous layer was washed with EtOAc (2×40 mL). The combined organic layers were washed with brine, dried (Na$_2$SO$_4$), filtered and concentrated in vacuum. The crude residue was purified by flash chromatography (10% MeOH in CH$_2$Cl$_2$) to afford a light yellow oil (4b, 50 mg, 31%). $^1$H NMR (CDCl$_3$, 400 MHz) δ 7.74-7.65 (m, 2H), 7.43 (dd, J=1.8, 6.8 Hz, 1H), 5.28 (s, 2H), 3.95 (s, 3H), 1.58-1.41 (m, 10H); MS (ES+): 302.03.

5-Methyl 3,4-dihydro-4-oxo-2-(1-pyrrolidinylmethyl)-5-quinazolinecarboxy-late (4c) To a solution of 3 (125 mg, 0.53 mmol) in CH$_2$Cl$_2$ (8 mL) was added Et$_3$N (81 mg, 0.80 mmol) and p-toluenesulfonyl chloride (826 mg, 0.59 mmol) at 0° C. The reaction mixture was allowed to warm to room temperature and stirred for 2 h. The solvents were removed in vacuum. To the resulting oil was added EtOH (5 mL) and pyrrolidine (55 mg, 0.77 mmol) at room temperature. The reaction mixture was heated at 50° C. for 1.5 h and then cooled to room temperature. The solvent was removed in vacuum. EtOAc (40 mL) and H$_2$O (25 mL) were added and the aqueous layer was washed with EtOAc (2×40 mL). The combined organic layers were washed with brine, dried (Na$_2$SO$_4$), filtered and concentrated in vacuum. The crude residue was purified by flash chromatography (10% MeOH in CH$_2$Cl$_2$) to afford a light yellow oil (4c, 40 mg, 26%) which was used directly in next step.

2,9-Dihydro-8-[(dimethylamino)methyl]-3H-pyridazino [3,4,5-de]quinazoline-3-one (5a) To a solution of 4a (70 mg, 0.27 mmol) in EtOH (4 mL) was added NH$_2$NH$_2$ (2 mL) at room temperature. The resulting mixture was heated to 100° C. and stirred overnight. The reaction mixture was concentrated in vacuum and purified by flash chromatography (2% MeOH in CH$_2$Cl$_2$ with 0.5% NH$_4$OH to 4% MeOH in CH$_2$Cl$_2$ with 0.5% NH$_4$OH) to afford a yellow solid (5a, 30 mg, 45%). Mp>240° C. (dec.); $^1$H NMR (CDCl$_3$, 400 MHz) δ 11.9 (br s, 1H), 7.78 (dd, J=0.76, 7.6 Hz, 1H), 7.67 (t, J=7.8 Hz, 1H), 7.48 (d, J=7.4 Hz, 1H), 3.42 (s, 2H), 2.43 (s, 6H); MS (ES−): 242.14; Anal. Calcd for C$_{12}$H$_{13}$N$_5$O.(0.25H$_2$O): C, 58.17; H, 5.49; N, 28.27. Found: C, 57.91; H, 5.46; N, 28.55.

2,9-Dihydro-8-[(1-piperidinylmethyl]-3H-pyridazino[3,4,5-de]quinazoline-3-one (5b) To a solution of 4b (50 mg, 0.17 mmol) in EtOH (3 mL) was added hydrazine (2.5 mL). The reaction mixture was stirred at 120° C. for 18 h and then cooled to room temperature. EtOAc (20 mL) and H$_2$O (20 mL) was added. The aqueous layer was washed with EtOAc. The combined organic layers were washed with brine (10 mL), dried (Na$_2$SO$_4$). The crude residue was purified by flash chromatography (10% MeOH in CH$_2$Cl$_2$) to afford a white solid (5b, 23.6 mg, 49%). Mp: 250-252° C.; $^1$H NMR (CDCl$_3$, 400 MHz) δ 10.01 (s, 1H), 7.80 (d, J=7.87 Hz, 1H), 7.50 (t, J=7.73, 1H), 7.45 (s, 1H), 3.45 (s, 2H), 2.40-2.60 (m, 4H), 1.50-1.45 (m, 6H); MS (ES+): 284; Anal. Calcd for C$_{15}$H$_{17}$N$_5$O$_1$.(0.5H$_2$O): C, 61.63; H, 6.21; N, 23.96. Found: C, 61.53; H, 6.21; N, 23.81.

2,9-Dihydro-8-[(1-pyrrolidinylmethyl]-3H-pyridazino[3,4,5-de]quinazoline-3-one (5c) To a solution of 4c (40 mg, 0.14 mmol) in EtOH (5 mL) was added hydrazine (2.5 mL). The reaction mixture was stirred at 120° C. for 18 h and then cooled to room temperature. EtOAc (20 mL) and H$_2$O (20 mL) was added. The aqueous layer was washed with EtOAc. The combined organic layers were washed with brine (10 mL), dried (Na$_2$SO$_4$). The crude residue was purified by flash chromatography (10% MeOH in CH$_2$Cl$_2$) to afford a white solid (5c, 15 mg, 40%). Mp: 230-232° C.; $^1$H NMR (CDCl$_3$, 400 MHz) δ 10.70 (s, 1H), 8.25 (d, J=7.63 Hz, 1H), 8.10 (t, J=7.82 Hz, 1H), 7.75-7.80 (m, 1H), 3.80 (s, 2H), 3.0 (s, 4H), 2.30 (s, 4H); MS (ES+): 270.07; Anal. Calcd for C$_{14}$H$_{15}$N$_5$O$_1$.(0.23H$_2$O): C, 59.17; H, 5.39; N, 24.25. Found: C, 59.16; H, 5.51; N, 24.39.

3-Oxo-2,9-dihydro-3H-pyridazino[3,4,5-de]quinazoline-8-carboxylic hydrazide (6) A mixture of 2 (200 mg, 0.72 mmol) in NH$_2$NH$_2$ (3 mL) was refluxed overnight. The reaction mixture was cooled to room temperature and the excess NH$_2$NH$_2$ was removed in vacuum. The crude residue was washed with MeOH and CH$_2$Cl$_2$ to afford a yellow solid (6, 100 mg, 56%). Mp>300° C.; $^1$H NMR (DMSO-d$_6$, 400 MHz) δ 11.93 (s, 1H), 9.94 (br s, 1H), 7.76 (t, J=7.8 Hz, 1H), 7.64 (dd, J=0.94, 7.8 Hz, 1H), 7.59 (dd, J=0.94, 7.8 Hz, 1H), 4.68 (br s, 2H); MS (ES+): 245.34; Anal. Calcd for C$_{10}$H$_8$N$_6$O$_2$.(0.8H$_2$O): C, 46.44; H, 3.74; N, 32.5. Found: C, 45.99; H, 3.89; N, 32.89.

EXAMPLE 2

Preparation of 8-Amino-2,9-dihydro-3H-pyridazino[3,4,5-de]quinazoline-3-one (9) (Scheme 2)

Chloroformamidine hydrochloride (7) To a solution of cyanamide (1 g, 23.78 mmol) in Et$_2$O (20 mL) was bubbling through HCl gas until no more precipitate formed. The precipitate was filtered and dried in vacuum over KOH to afford a white solid (7, 2.5 g, 93%) that was used directly in the next step. MS (ES+): 116.12.

5-Methyl 2-amino-4-oxo-3,4-dihydroquinazoline-5-carboxylate (8) To a solution of 1 (2.75 g, 13 mmol) in Dowtherm A (25 mL) was added 7 (1.5 g, 13 mmol) and Me$_2$SO$_2$ (7.96 g, 84.5 mmol) at room temperature. The reaction mixture was heated to 165° C. and stirred for 2 h. The reaction mixture was cooled to room temperature and purified by flash chromatography (5% MeOH in CH$_2$Cl$_2$ to 10% MeOH in CH$_2$Cl$_2$) to afford a white solid (8, 2.5 g, 88%). $^1$H NMR (DMSO-d$_6$, 400 MHz) δ 11.05 (br s, 1H), 7.56 (dd, J=7.5, 8.2 Hz, 1H), 7.25 (dd, J=0.95, 8.2 Hz, 1H), 6.98 (d, J=7.2 Hz, 1H), 6.50 (br s, 2H), 3.76 (s, 3H).

8-Amino-2,9-dihydro-3H-pyridazino[3,4,5-de]quinazoline-3-one (9) A mixture of 8 (200 mg, 0.91 mmol) in EtOH/NH$_2$NH$_2$ (1:1, 10 mL) was heated to 100° C. and stirred overnight. The reaction mixture was allowed to cool to room temperature. The resulting precipitate was filtered and washed with EtOH to afford a yellow solid (9, 176 mg, 87%). Mp>300° C.; $^1$H NMR (DMSO-d$_6$, 400 MHz) δ 11.40 (br s, 1H), 7.61 (t, J=7.8, 8.0 Hz, 1H), 7.44 (dd, J=0.95, 8.0 Hz, 1H), 7.15 (dd, J=0.95, 7.8 Hz, 1H), 6.33 (s, 2H); MS (ES+): 202.18; Anal. Calcd for C$_9$H$_7$N$_5$O.(1N$_2$H$_4$): C, 46.35; H, 4.75; N, 42.04. Found: C, 46.2; H, 4.83; N, 41.76.

EXAMPLE 3

Preparation of 2,9-Dihydro-3H-pyridazino[3,4,5-de]quinazoline-3-one (13) (Scheme 3)

5-Methyl 4-oxo-3,4-dihydroquinazoline-5-carboxylate (12) To a solution of 1 (2.0 g, 9.57 mmol) in 2-methoxyethanol (30 mL) was added formamidine acetate (2.5 g, 24.0 mmol) at room temperature. The reaction mixture was refluxed at 135° C. for 2 h. The reaction mixture was cooled to room temperature. The solvent was removed and water was added. The resulting precipitate was filtered, washed with H$_2$O, and dried in vacuum. The resulting off-white solid (12, 1 g, 50%) was used directly next step. $^1$H NMR (CD$_3$OD, 400 MHz) δ 8.01 (s, 1H), 7.72-7.80 (m, 1H), 7.68 (dd, J=1.3, 1.1, 8.4, 8.2 Hz, 1H), 7.37 (dd, J=1.1, 1.3, 7.1, 7.2 Hz, 1H), 3.83 (s, 3H).

2,9-Dihydro-3H-pyridazino[3,4,5-de]quinazoline-3-one (13) A mixture of 12 (1.0 g, 5.0 mmol) in EtOH/NH$_2$NH$_2$ (1:1, 20 mL) was refluxed at 140° C. for 4 hrs. The reaction mixture was allowed to cool to room temperature. The solvent was removed partially and the resulting precipitate was filtered and washed with EtOH to afford a yellow solid (13, 400 mg, 43%). Mp>300° C.; $^1$H NMR (DMSO-d$_6$, 400 MHz) δ 11.74 (br s, 1H), 7.77 (s, 1H), 7.74 (t, J=7.8, 8.0 Hz, 1H), 7.62 (dd, J=0.96, 1.1, 7.8, 8.0 Hz, 1H), 7.33 (dd, J=0.96, 7.8 Hz, 1H); MS (ES+): 187; Anal. Calcd for C$_9$H$_6$N$_4$O: C, 58.06; H, 3.25; N, 30.09. Found: C, 57.77; H, 3.32; N, 30.29.

EXAMPLE 4

Preparation of 9-[(Hydrozinooxy)carbonyl]-2,7-dihydro-6-methoxy 3H-pyrido-[4,3,2-de]phthalazin-3-one (16) (Scheme 4)

Diethyl[[[2-methoxy-5-(methoxycarbonyl)phenyl]amino]methylene]propanedioate (14) A mixture of methyl 3-amino-4-methoxybenzoate (2.0 g, 11 mmol) and diethyl ethoxymethylenemalonate (5 mL) was stirred at room temperature for 5 h. Water was added and the precipitate was filtered, washed with H$_2$O and Et$_2$O, dried in vacuum to afford a yellow solid (14, 3.9 g, 100%). $^1$H NMR (DMSO-d$_6$, 400 MHz) δ 11.98 (d, J=14 Hz, 1H), 8.51 (d, J=14 Hz, 1H), 7.89 (s, 1H), 7.75 (dd, J=1.7, 8.6 Hz, 1H), 7.25 (d, J=8.6 Hz, 1H), 4.20 (q, J=7.1, 14 Hz, 2H), 4.14 (q, J=7.1, 14 Hz, 2H), 3.98 (s, 3H), 3.84 (s, 3H), 1.20-1.29 (m, 6H).

3-Ethyl 5-methyl 1,4-dihydro-8-methoxy-4-oxo-3,5-quinolinedioate (15) A suspension of 14 (1.0 g, 2.85 mmol) in Dowtherm A (10 mL) was heated at 300~360° C. for 1 h. The reaction mixture was cooled to room temperature. The resulting precipitate was filtered, washed with Et$_2$O, and dried in vacuum to afford a yellow solid (15, 1.3 g, 46%). $^1$H NMR (DMSO-d$_6$, 400 MHz) δ 12.09 (br s, 1H), 8.35 (s, 1H), 7.29 (q, J=8.2, 20 Hz, 2H), 4.20 (q, J=7.2, 14, 7.1 Hz, 2H), 4.02 (s, 3H), 3.77 (s, 3H), 1.25 (t, J=7.1, 7.2 Hz, 3H).

9-[(Hydrozinooxy)carbonyl]-2,7-dihydro-6-methoxy 3H-pyrido-[4,3,2-de]phthalazin-3-one (16) A mixture of 15 (400 mg, 1.31 mmol) in EtOH/NH$_2$NH$_2$ (1:1, 10 mL) was refluxed at 140° C. for 3 hrs. The reaction mixture was allowed to cool to room temperature. The resulting precipitate was filtered and washed with Et$_2$O to afford a yellow solid (16, 80 mg, 22%). Mp>300° C.; $^1$H NMR (DMSO-d$_6$, 300 MHz) 11.83 (s, 1H), 10.24 (s, 1H), 10.07 (s, 1H), 7.97 (s, 1H), 7.73 (d, J=8.5 Hz, 1H), 7.55 (d, J=8.4 Hz, 1H), 4.57 (d, J=3.8

Hz, 2H), 4.04 (s, 3H); Anal. Calcd for $C_{12}H_{11}N_5O_3 \cdot (1H_2O)$: C, 49.48; H, 4.5; N, 24.04. Found: C, 49.44; H, 4.53; N, 24.17.

EXAMPLE 5

Preparation of 9-[(Hydrozinooxy)carbonyl]-2,7-dihydro-3H-pyrido-[4,3,2-de]phthalazin-3-one (21) (Scheme 5)

Methyl 4-chloro-3-aminobenzoate (17) To a solution of methyl 4-chloro-3-nitrobenzoate (3.0 g, 13.9 mmol) in EtOAc (50 mL) was added 10% Pd/C (0.64 g). The resulting mixture was hydrogenated under $H_2$ (50 psi) on a Parr hydrogenation apparatus at room temperature for 1 h. The catalyst was filtered off on a pad of celite and the filtrate was concentrated in vacuum to afford a dark oil (17, 2.0 g, 77%). $^1H$ NMR (DMSO-$d_6$, 300 MHz) δ 7.40 (d, J=2.1 Hz, 1H), 7.30 (d, J=8.2 Hz, 1H), 7.08 (dd, J=2.1, 8.4 Hz, 1H), 3.79 (s, 3H).

Diethyl[[[2-chloro-5-(methoxycarbonyl)phenyl]amino]methylene]propanedioate (18) A mixture of 17 (2.0 g, 10.7 mmol) and diethyl ethoxymethylene-malonate (5 mL) was stirred at room temperature overnight. Water was added and the resulting precipitate was filtered, washed with $H_2O$ and $Et_2O$, dried in vacuum to afford a yellow solid (18, 3.0 g, 79%). $^1H$ NMR (DMSO-$d_6$, 300 MHz) δ 11.20 (d, J=13 Hz, 1H), 8.54 (d, J=8.4 Hz, 1H), 8.05 (d, J=1.3 Hz, 1H), 7.73 (d, J=8.2 Hz, 1H), 7.69 (dd, J=1.7, 8.4 Hz, 1H), 4.22 (q, J=7.1, 14 Hz, 2H), 4.16 (q, J=7.1, 14 Hz, 2H), 3.88 (s, 3H), 1.25 (t, J=7.1 Hz, 3H), 1.25 (t, J=7.1 Hz, 3H).

9-[(Hydrozinooxy)carbonyl]-2,7-dihydro-6-chloro-3H-pyrido-[4,3,2-de]phthalazin-3-one (20) A suspension of 14 (1.0 g, 2.81 mmol) in Dowtherm A (10 mL) was heated at 300–330° C. for 45 min. The reaction mixture was cooled to room temperature. Most of the solvent was removed in vacuum. The solution was used directly next step.

To the above solution was added EtOH/$NH_2NH_2$ (1:1, 10 mL) at room temperature and the reaction mixture was refluxed at 140° C. overnight. After the reaction, the reaction mixture was allowed to cool to room temperature. The resulting precipitate was filtered and washed with $Et_2O$ to afford a yellow solid (20, 220 mg, 28%). Mp>300° C.; $^1H$ NMR (CDCl$_3$, 300 MHz) δ 10.05 (s, 1H), 8.12 (s, 1H), 7.86 (d, J=8.4 Hz, 1H), 7.58 (d, J=8.2 Hz, 1H), 4.55 (s, 2H); Anal. Calcd for $C_{11}H_8ClN_5O_2$: C, 46.09; H, 3.16; N, 24.43; Cl, 12.37. Found: C, 45.79; H, 3.35; N, 24.88; Cl, 12.25.

9-[(Hydrozinooxy)carbonyl]-2,7-dihydro-3H-pyrido-[4,3,2-de]phthalazin-3-one (21) To a suspension of 20 (110 mg, 0.40 mmol) in DMF (50 mL) was added 10% Pd/C (100 mg). The resulting mixture was hydrogenated under $H_2$ (40 psi) on a Parr hydrogenation apparatus at room temperature overnight. The catalyst was filtered off on a pad of celite and washed with $Et_2O$. The filtrate was concentrated in vacuum to afford a yellow solid (21, 20 mg, 21%). Mp>300° C.; $^1H$ NMR (DMSO-$d_6$, 300 MHz) δ 12.17 (s, 1H), 11.77 (d, J=5.7 Hz, 1H), 10.54 (s, 1H), 8.17 (d, J=6.3 Hz, 1H), 7.82 (t, J=7.8 Hz, 1H), 7.73 (d, J=7.6 Hz, 1H), 7.55 (d, J=8.2 Hz, 1H); Anal. Calcd for $C_{11}H_9N_5O_2 \cdot (1.7H_2O)$: C, 48.25; H, 4.56; N, 25.57. Found: C, 48.44; H, 4.06; N, 25.12.

EXAMPLE 6

Preparation of Phthalazine Derivatives (27, 28 and 30) (Scheme 6)

Methyl 4-chloro-3-amino-benzoate (22). To a solution of 4-chloro-3-amino-benzoic acid (10.0 g, 58.3 mmol) in methanol (50 mL) was added acetyl chloride (13.0 mL) dropwise at room temperature. After the addition, the reaction mixture was heated at 70° C. for 3 h and then cooled to room temperature. The solvent was removed under reduced pressure and water (100 mL) was added. The resulting solution was neutralized with NaHCO$_3$ followed by extraction with EtOAc (3×100 mL). The combined organic layers were dried (MgSO$_4$) and concentrated in vacuum to afford a yellow oil (22, 10.5 g, 97%). $^1H$ NMR (DMSO-$d_6$, 300 MHz) δ 7.41 (??d, J=2.1 Hz, 1H), 7.31 (d, J=8.4 Hz, 1H), 7.09 (dd, J=2.1, 8.4 Hz, 1H), 5.66 (br s, 2H), 3.80 (s, 3H).

2-[2-Chloro-5-(methoxycarbonyl)phenylamino]-2-butenedioic acid diethyl ester (23). To a solution of 22 (5.00 g, 26.9 mmol) in ethanol (50 mL) was added but-2-ynedioic acid diethyl ester (5.02 g, 29.5 mmol) at room temperature. The reaction mixture was heated at 90° C. for 18 h and then cooled to room temperature. The solvent was removed under reduced pressure. The crude residue was washed with a solution of 1:1 Hexanes/diethyl ether (100 mL) to afford a white solid (23, 9.08 g, 95.1%). $^1H$ NMR (DMSO-$d_6$, 300 MHz) δ ?9.80 (s, 1H), 7.65-7.66 (m, 2H), 7.38 (s, 1H), 5.54 (s, 1H), 4.13-4.22 (m, 4H), 3.83 (s, 3H), 1.22 (t, J=7.1 Hz, 3H), 1.11 (t, J=7.1 Hz, 3H).

8-Chloro-4-oxo-1,4-dihydro-2,5-quinolinedicarboxylic acid 2-ethyl 5-methyl ester (24). A suspension of 23 (9.00 g, 25.4 mmol) in biphenyl ether (100 mL) was heated to 250° C. and stirred for 3 h. Then the reaction mixture was cooled to room temperature and purified by flash chromatography (hexanes to EtOAc) to afford a colorless oil (24, 3.88 g, 49.4%). $^1H$ NMR (CDCl$_3$, 300 MHz) δ 9.39 (br s, 1H), 7.75 (d, J=8.0 Hz, 1H), 7.24 (d, J=8.0 Hz, 1H), 6.96 (s, 1H), 4.54 (q, J=7.0 Hz, 2H), 4.00 (s, 3H), 1.46 (t, J=7.0 Hz, 3H).

8-Chloro-4-oxo-1,4-dihydro-2,5-quinolinedicarboxylic acid (25). To a solution of 24 (10.0 g, 32.3 mmol) in ethanol (100 mL) was added 10% aqueous KOH solution (100 mL) at room temperature. The reaction mixture was heated at 100° C. for 24 h and then cooled to room temperature. The reaction mixture was concentrated in vacuum. The resulting aqueous solution was acidified with 2N HCl to pH=6.5, where a solid precipitated and was collected through a filtration. The solid was washed with $H_2O$ (100 mL) and $Et_2O$ (100 mL), and dried in vacuum at 60° C. to give an off-white solid (25, 8.00 g, 92.9%). $^1H$ NMR (DMSO-$d_6$, 300 MHz) δ ?7.97 (d, J=7.8 Hz, 1H), 7.39 (d, J=7.8 Hz, 1H), 6.90 (s, 1H).

4-Oxo-1,4-dihydro-2,5-quinolinedicarboxylic acid (26). To a solution of 25 (7.90 g, 29.5 mmol) in 10% aqueous KOH solution (100 mL) was added 10% Pd/C (0.500 g). The reaction mixture was hydrogenated (50 psi) on a Parr hydrogenation apparatus at room temperature for 4 h. The catalyst was filtered off on a pad of celite and the filtrate was acidified with 2N HCl to pH=6.5, where a solid precipitated and was collected through a filtration. The solid was washed with $H_2O$ (100 mL) and $Et_2O$ (100 mL), and dried in vacuum at 60° C. to give an off-white solid (26, 6.79 g, 98.6%). $^1H$ NMR (DMSO-$d_6$, 300 MHz) δ ?8.12 (d, J=8.2 Hz, 1H), 7.76 (t, J=8.2 Hz, 1H), 7.48 (d, J=8.2 Hz, 1H), 6.74 (s, 1H).

3-Oxo-2,7-dihydro-3H-pyrido[4,3,2-de]phthalazine-8-carboxylic acid (27). To a solution of 26 (23.1 g, 99.1 mmol) in ethylene glycol (300 mL) heated to 140° C. was carefully added hydrazine hydrate (4.75 g, 95.0 mmol) dropwise. The reaction mixture was heated to 150° C. and stirred for 44 h. Removal of the 90% of the ethylene glycol under vacuum gave a precipitate, which was washed with methanol (100 mL) and diethyl ether (100 mL) to give a yellow solid (27, 16.5 g, 72.7%). $^1H$ NMR (DMSO-$d_6$, 300 MHz) δ 11.85 (s, 1H), 10.43 (s, 1H), 7.61-7.63 (m, 2H), 7.43-7.46 (m, 1H), 6.49 (s, 1H).

3-Oxo-2,7-dihydro-3H-pyrido[4,3,2-de]phthalazine-8-carboxylic acid sodium salt (28) To a solution of NaOH (1 g) in water (100 mL) was added 27 (1.00 g, 4.36 mmol) and the reaction mixture was stirred for 1 h. Any insoluble material was filtered off through a fine frit glass funnel and the aqueous layer was concentrated in vacuum to afford a yellow solid (28, 0.898 g, 82.1%). $^1$H NMR (D$_2$O, 300 MHz) δ ?7.23 (t, J=7.8 Hz, 1H), 6.97 (d, J=7.8 Hz, 1H), 6.88 (d, J=7.8 Hz, 1H), 5.91 (s, 1H). Anal: Calcd for C$_{11}$H$_6$N$_3$O$_4$Na (1.0H$_2$O and 2.45NaOH): C, 35.98; H, 2.87; N, 11.44. Found: C, 35.76; H, 2.86; N, 11.82.

4-Oxo-1,4-dihydro-2,5-quinolinedicarboxylic acid 2-ethyl 5-methyl ester (29). To a suspension of 24 (4.50 g, 14.5 mmol) in EtOAc (100 mL) was added Et$_3$N (50 mL). The reaction mixture was heated to 50° C. to generate a clear solution. 10% Pd/C (0.500 g) was added carefully. The reaction mixture was hydrogenated (50 psi) on a Parr hydrogenation apparatus at room temperature for 4 h. Then the catalyst was filtered off on a pad of celite and the filtrate washed with water (100 mL). The aqueous layer was extracted with EtOAc (100 mL) and the combined organic layers were dried (MgSO$_4$), filtered, and concentrated. The crude residue was washed with Et$_2$O (100 mL) to give an off-white solid (29, 3.46 g, 99.1%). $^1$H NMR (DMSO-d$_6$, 300 MHz) δ ?8.05 (d, J=8.6 Hz, 1H), 7.75 (t, J=8.6 Hz, 1H), 7.29 (d, J=8.6 Hz, 1H), 6.63 (s, 1H), 4.44 (q, J=7.3 Hz, 2H), 3.80 (s, 3H), 1.37 (t, J=7.3 Hz, 3H).

3-Oxo-2,7-dihydro-3H-pyrido[4,3,2-de]phthalazine-8-carboxylic acid hydrazide (30). To a solution of 29 (1.38 g, 5.02 mmol) in ethylene glycol (25 mL) was added hydrazine hydrate (1.00 g, 20.0 mmol). The reaction mixture was heated to 180° C. and stirred for 18 h. After cooled to room temperature, the resulting yellow precipitate was filtered, washed with Et$_2$O (100 mL), dried in vacuum at 90° C. for 6 h to give a yellow solid (30, 1.10 g, 90.2%). $^1$H NMR (DMSO-d$_6$, 300 MHz) δ 11.89 (s, 1H), 10.51 (s, 1H), 10.09 (s, 1H), 7.62-7.68 (m, 2H), 7.46-7.49 (m, 1H), 6.57 (s, 1H), 4.60 (br s, 2H); Anal. Calcd for C$_{11}$H$_9$N$_5$O$_2$: C, 54.32; H, 3.73; N, 28.79. Found: C, 54.42; H, 3.72; N, 28.86.

EXAMPLE 7

Preparation of 6-Fluoro-3-oxo-2,7-dihydro-3H-pyrido[4,3,2-de]phthalazine-8-carboxylic acid (36) (Scheme 7)

Methyl 4-fluoro-3-nitrobenzoate (31). To a solution of 4-fluoro-3-nitrobenzoic acid (15.0 g, 81.1 mmol) in MeOH (500 mL) was added H$_2$SO$_4$ (1 mL) and the reaction mixture was heated at 70° C. for 72 h and then cooled to room temperature. The reaction solution was d neutralized to pH=7.0 with NaHCO$_3$, then concentrated in vacuum. H$_2$O (300 mL) was added and washed with EtOAc (3×300 mL). The combined organic layers were dried (MgSO$_4$) and concentrated in vacuum to give a yellow oil (31, 16.0 g, 99.0%). $^1$H NMR (CDCl$_3$, 300 MHz) δ 8.76 (dd, J=2.3, 7.3 Hz, 1H) 8.30-8.34 (m, 1H), 7.39 (t, J=10.1 Hz, 1H), 3.98 (s, 3H).

Methyl 4-fluoro-3-aminobenzoate (32) To a solution of 31 (16.0 g, 80.3 mmol) in MeOH (250 mL) was added 10% Pd/C (0.500 g). The reaction mixture was hydrogenated (50 psi) on a Parr hydrogenation apparatus at room temperature for 4 h. The catalyst was filtered off on a pad of celite and the filtrate was concentrated in vacuum to afford a colorless oil (32, 12.2 g, 90.0%). $^1$H NMR (CDCl$_3$, 300 MHz) δ ?7.48 (dd, J=2.1, 8.6 Hz, 1H), 7.39-7.43 (m, 1H), 7.02 (d, J=8.6, 10.7 Hz, 1H), 3.88 (s, 3H), 3.84 (br s, 2H).

2-[2-Fluoro-5-(methoxycaronyl)phenylamino]-2-butenedioic acid diethyl ester (33) To a solution of 32 (5.00 g, 29.6 mmol) in ethanol (200 mL) was added but-2-ynedioic acid diethyl ester (6.29 g, 37.0 mmol) and the reaction mixture was stirred at room temperature for 24 h. The solvent was then removed under reduced pressure and the residue was purified by flash chromatography (Hexanes to 25% EtOAc in Hexanes) to give a yellow oil (33, 7.63 g, 76.5%). $^1$H NMR (CDCl$_3$, 300 MHz) δ 9.64 (br s, 1H), 7.72-7.78 (m, 1H), 7.62 (dd, J=7.8, 1.9 Hz, 1H), 7.12 (t, J=10.3 Hz, 1H), 5.61 (s, 1H), 4.19-4.27 (m, 4H), 3.89 (s, 3H), 1.31 (t, J=7.0, 3H), 1.20 (t, J=7.0, 3H).

8-Fluoro-4-oxo-1,4-dihydro-2,5-quinolinedicarboxylic acid 2-ethyl 5-methyl ester (34). A suspension of 33 (25.0 g, 73.7 mmol) in Dowtherm A (200 mL) was heated to 300° C. over the course of 30 minutes and then stirred at 300° C. for 1 h. The reaction solution was cooled to room temperature and purified by flash chromatography (Hexanes to EtOAc) to afford a white solid (34, 12.1 g, 56.1%). $^1$H NMR (CDCl$_3$, 300 MHz) δ 9.19 (br s, 1H), 7.42 (t, J=8.2, 1H), 7.21-7.25 (m, 1H), 6.92 (s, 1H), 4.51 (q, J=7.1, 2H), 3.99 (s, 3H), 1.46 (t, J=7.1, 3H).

8-Fluoro-4-oxo-1,4-dihydro-2,5-quinolinedicarboxylic acid (35). To a 2 N aqueous HCl (200 mL) solution was added 34 (10.0 g, 34.1 mmol). The reaction mixture was heated at 100° C. for 18 h and then cooled to room temperature. The resulting precipitate was filtered and dried under vacuum at 60° C. for 18 h to afford an off-white solid (35, 8.11 g, 94.7%). $^1$H NMR (DMSO-d$_6$, 300 MHz) δ ?7.65 (t, J=8.2, 1H), 7.39-7.43 (m, 1H), 6.93 (s, 1H).

6-Fluoro-3-oxo-2,7-dihydro-3H-pyrido[4,3,2-de]phthalazine-8-carboxylic acid (36). To a solution of 35 (0.600 g, 2.39 mmol) in EtOH (5 mL) was added hydrazine (0.0840 g, 2.63 mmol). The resulting mixture was heated at 90° C. for 24 h and then cooled to room temperature. The resulting precipitate was filtered, washed with Et$_2$O (25 mL), and dried in vacuum at 60° C. for 6 h to give a white solid (36, 0.484 g, 74.5%). $^1$H NMR (DMSO-d$_6$, 300 MHz) δ ?8.25-8.30 (m, 1H), 7.51-7.57 (m, 1H), 7.06 (s, 1H); Anal. Calcd for C$_{11}$H$_6$N$_3$O$_3$F (2H$_2$O): C, 46.65; H, 3.56; N, 14.84. Found: C, 46.80; H, 3.59; N, 14.86.

EXAMPLE 8

Preparation of 6-Methoxy-3-oxo-2,7-dihydro-3H-pyrido[4,3,2-de]phthalazine-8-carboxylic acid hydrozide (39) (Scheme 8)

2-[2-Methoxy-5-(methoxycarbonyl)phenylamino]-2-butenedioic acid dimethyl ester (37) To a solution of Methyl 3-amino-4-methoxybenzoate (5.0 g, 27.6 mmol) in MeOH (60 mL) was added dimethyl acetylenedicarboxylate (4.31 g, 30.36 mmol) at room temperature. The reaction mixture was refluxed for 20 min and then cooled to room temperature. The solvent was removed. The crude residue was triturated in ether to give a yellow solid (37, 4.35 g, 49%). $^1$H NMR (DMSO-d$_4$, 400 MHz) δ 9.8 (s, 1H), 7.90 (dd, J=1.9 Hz, 8.6 Hz, 1H), 7.50-7.60 (m, 1H), 7.35 (d, J=8.59 Hz, 1H), 5.50 (s, 1H), 4.08 (s, 3H), 4.0 (s, 3H), 3.90 (s, 3H), 3.85 (s, 3H).

8-Methoxy-4-oxo-1,4-dihydro-2,5-quinolinedicarboxylic acid dimethyl ester (38) A suspension of 37 (4.20 g, 12.99 mmol) in Dowtherm A (30 mL) was heated at 300° C. for 35 min while monitored by TLC and then cooled to 0° C. The resulting precipitate was filtered and washed with Et$_2$O to afford a white solid (37, 2.0 g, 53%). $^1$H NMR (DMSO-d$_6$, 400 MHz) δ 10.0 (s, 1H), 7.34 (d, J=7.84 Hz, 1H), 7.30 (d, J=8.09 Hz, 1H), 6.60 (s, 1H), 4.05 (s, 3H), 3.96 (s, 3H), 3.77 (s, 3H).

6-Methoxy-3-oxo-2,7-dihydro-3H-pyrido[4,3,2-de]phthalazine-8-carboxylic acid hydrozide (39) To a suspension of 38 (0.45 g, 1.54 mmol) in EtOH (20 mL) was added hydrazine (1 mL) at room temperature. The reaction mixture was heated at 68° C. for 1.5 h and then cooled to room temperature. The resulting precipitate was filtered and washed with $Et_2O$ to afford a white solid (39, 0.31 g, 74%). $^1$H NMR (DMSO-$d_6$, 300 MHz) δ 10.5 (br s, 1H), 9.0 (br s, 1H), 7.15-7.25 (m, 2H), 7.1 (br s, 1H), 6.8 (br s, 1H), 4.90 (br s, 2H), 4.03 (s, 3H). Mp: 305-307° C.; Anal. Calcd for $C_{12}H_{11}N_5O_3.(0.75H_2O)$: C, 50.26; H, 4.39; N, 24.42. Found: C, 50.33; H, 4.46; N, 22.04.

EXAMPLE 9

Preparation of diazabenzo[de]anthracen-3-one Derivatives 43-48 (Scheme 9)

7-bromomethyl-9-oxoxanthene-1-carboxylic acid methyl ester (41). Brominating agents include N-bromosuccinimide, bromine, complexed bromine such as pyridinium bromide, and the like can be used to convert 7-methyl-9-oxoxanthene-1-carboxylic acid methyl ester 40 to 7-bromomethyl-9-oxoxanthene-1-carboxylic acid methyl ester 41. Solvents include chlorinated hydrocarbons, dipolar aprotic solvents, and various ethers. Temperature can range from 0-100 C. For example, a suspension of 7-methyl-9-oxoxanthene-1-carboxylic acid methyl ester (0.1 mol), N-bromosuccinimide (0.12 Mol) and benzoylperoxide (10 mg) in dry carbon tetrachloride (300 mL) is stirred at 60 C for 6 hours. The mixture is filtered, and the solid is washed successively with small amounts of chloroform, water and ether, and then dried to leave a desired product as white solid. For example, to a solution of compound 40 (1.97 g, 7.4 mmol) in carbon tetrachloride (400 mL) was added N-bromosuccinimide (1.44 g, 8.1 mmol) and a catalytic amount of benzoyl peroxide (45 mg, 3%). The reaction mixture was heated to reflux for 6 h and cooled to room temperature. The white precipitate was filtered out. The solvents were removed and the residue was recrystallized from EtOAc and hexanes. The crude product (2.05 g) was obtained and further recrystallization gave a pure white solid product 41 (1.15 g, 45%). $^1$H NMR (400 MHz, $CDCl_3$) of 2: 8.27 (d, J=2.5 Hz, 1H), 7.80-7.72 (m, 2H), 7.57 (dd, J=8.5 and 1.1 Hz, 1H), 7.48 (d, J=8.5 Hz, 1H), 7.33 (dd, J=7.0 and 1.1 Hz, 1H), 4.57 (s, 2H), 4.00 (s, 3H).

Displacement of the bromo group of compound 41 with nucleophiles such as amine using General procedure A provides the compound 42. The ketoester 42 can be cyclized with hydrazine using general procedure B to give desired final products. Compounds 43-48.

General Procedure A

To a solution of the bromo compound (41, 10 mmol) in dry DMF (100 mL) is added potassium carbonate (100 mmol) and secondary amine (10 mmol). The reaction mixture is heated to 70 C for 6 hours and cooled to room temperature. Water (100 mL) is added to the reaction mixture, followed by ethyl acetate (200 mL). The organic layer is collected, washed with water, brine and dried over sodium sulfate. The solvents are removed in vacuo. The residue is purified by column chromatography on silica gel using ethyl acetate/hexanes as eluent to give the product 42 in 50-90% of yield. For example, a procedure to make the intermediate toward to synthesize compound 43: To a solution of compound 41 (1.53 g, 4.4 mmol) in $CH_3CN$ (50 mL) was added $K_2CO_3$ (1.2 g, 8.7 mmol) and 1-methypiperazine (0.51 mL, 4.6 mmol). The reaction mixture was heated to reflux overnight and cooled to room temperature. The solid was filtered and the solvents were evaporated. The residue was workup by ethyl acetate and water by normal procedure. Column chromatography or acid/base extraction (the residue were added 150 mL of 1N HCl and 150 mL of EtOAc. The aq layer was separated and washed by 100 mL of EtOAC. Then the aq. layer was added 6N NaOH until pH>9. The solution was extracted by 100 mL of EtOAc twice. Organic layers were combined, washed by water and brine, dried over $MgSO_4$. Solvents were evaporated to give an oil 42a (0.95 g, 59%). $^1$H NMR (400 MHz, $CDCl_3$) of 42a: 8.18 (d, J=2.5 Hz, 1H), 7.75-7.71 (m, 2H), 7.56 (dd, J=8.5 and 1.1 Hz, 1H), 7.45 (d, J=8.5 Hz, 1H), 7.32 (dd, J=7.0 and 1.1 Hz, 1H), 4.04 (s, 3H), 3.58 (s, 2H), 2.45 (br, 8H), 2.27 (s, 3H).

General Procedure B

A benzopyrano[4,3,2-de]phthalazine ring can be formed by condensation of the ketone eaester with hydrazine. To a solution of the ketonester 42 (5 mmol) in absolute ethanol (10 mL) is added anhydrous hydrazine in ethanol (1 mL) drop wise at room temperature. The Solution is refluxed for overnight and cooled to room temperature. Ice-cold water (100 mL) is added and white solid is separated. The solid is collected by vacuum filtration and washed with water and small amount of methanol to give a white solid product in 40-85% of yield.

10-(4-Methyl-piperazin-1-ylmethyl)-2H-7-oxa-1,2-diaza-benzo[de]anthracen-3-one (43). To a solution of compound 42a (0.91 g, 2.5 mmol) in EtOH (15 mL) when refluxing was added hydrazine monohydrate (2 mL, 41 mmol). The reaction mixture was stirred for 5 h and cooled. Solvents were removed and water was added. Precipitate was filtered out, washed with 15% EtOH and collected to afford a white solid (0.85 g, 98%) 43. MS (ES+): 349; $^1$H NMR (400 MHz, DMSO-$d_6$): 12.61 (s, 1H), 7.99 (d, J=2.0 Hz, 1H), 7.92-7.85 (m, 2H), 7.68 (dd, J=7.5 and 2.0 Hz, 1H), 7.45 (dd, J=8.5 and 2.0 Hz, 1H), 7.35 (d, J=8.5 Hz, 1H), 3.52 (s, 2H), 2.40 (bs, 8H), 2.18 (s, 3H). Anal. Calcd. for $C_{20}H_{20}N_4O_2$: C, 68.95; H, 5.79; N, 16.08. Found: C, 69.04; H, 5.75; N, 16.2.

10-(4-Ethyl-piperazin-1-ylmethyl)-2H-7-oxa-1,2-diazabenzo[de]anthracen-3-one (44). Prepared from the compound 41 and 1-ethylpiperazine according to General Procedure A and B. Purification of compound by crystallization in ethanol gave a white solid product 44. MS (ES+): 363; $^1$H-NMR (DMSO-$d_6$, 400 MHz): 12.62 (s, 1H), 8.01 (s, 1H), 7.93-7.86 (m, 2H), 7.70 (dd, J=7.0 and 2.0 Hz, 1H), 7.47 (dd, J=8.5 and 2.0 Hz, 1H), 7.37 (d, J=8.5 Hz, 1H), 3.55 (s, 2H), 2.52-2.30 (b, 10H), 1.04 (m, 3H). Anal. Calcd. for $C_{21}H_{22}N_4O_2.(0.3H_2O)$: C, 68.57; H, 6.19; N, 15.23. Found: C, 68.21; H, 6.19; N, 15.38

10-[4-(2-Hydroxy-ethyl)-piperazin-1-ylmethyl]-2H-7-oxa-1,2-diaza-benzo[de]anthracen-3-one (45). Prepared from the compound 41 and N-(2-hydroxyethyl)piperazine according to General Procedure A and B. Purification of compound by crystallization in ethanol gave a white solid product 45. MS (ES+): 379; $^1$H-NMR (DMSO-$d_6$, 400 MHz): 12.62 (s, 1H), 8.00 (s, 1H), 7.92-7.85 (m, 2H), 7.69 (d, J=7.0 Hz, 1H), 7.42 (d, J=8.5 Hz, 1H), 7.31 (d, J=8.6 Hz, 1H), 3.53-3.48 (m, 4H), 2.50-2.35 (m, 10H). Anal. Calcd. for $C_{21}H_{22}N_4O_3$: C, 66.65; H, 5.86; N, 14.81. Found: C, 66.39; H, 5.80; N, 14.94.

10-{4-[2-(2-Hydroxy-ethoxy)-ethyl]-piperazin-1-ylmethyl}-2H-7-oxa-1,2-diazabenzo[de]anthracen-3-one (46). Prepared from the compound 41 and 1-hydroxyethylethoxypiperazine according to General Procedure A and B. Purification of compound by crystallization in ethanol gave a white solid product 7. MS (ES+): 423. $^1$H-NMR (DMSO-d$_6$, 400 MHz): 12.62 (s, 1H), 8.01 (s, 1H), 7.93-7.95 (m, 2H), 7.69 (dd, J=7.0 and 2.0 Hz, 1H), 7.47 (dd, J=8.5 and 2.0 Hz, 1H), 7.37 (d, J=8.5 Hz, 1H), 3.57-3.50 (m, 4H), 3.47 (m, 2H), 3.39 (m, 2H), 2.49-37 (m, 10H). Anal. Calcd. for $C_{23}H_{26}N_4O_4$·(0.15H$_2$O): C, 64.97; H, 6.23; N, 13.18. Found: C, 64.95; H, 6.21; N, 13.24.

10-{[Bis-(2-hydroxy-ethyl)-amino]-methyl}-2H-7-oxa-1,2-diaza-benzo[de]anthracen-3-one (47)

Prepared from the compound 41 and diethanolamine according to General Procedure A and B. Purification of compound by crystallization in ethanol gave a white solid product 47. MS (ES+): 354; Mp 222-225 C; $^1$H-NMR (DMSO-d$_6$, 400 MHz): 12.59 (s, 1H), 8.00 (s, 1H), 7.91-7.84 (m, 2H), 7.67 (dd, J=7.0 and 2.0 Hz, 1H), 7.52 (dd, J=8.5 and 2.0 Hz, 1H), 7.34 (d, J=8.5 Hz, 1H), 3.70 (s, 2H), 3.47 (t, J=6.4 Hz, 4H), 2.56 (t, J=6.4 Hz, 4H). Anal. Calcd. for $C_{19}H_{19}N_3O_4$: C, 64.58; H, 5.42; N, 11.89. Found: C, 64.32; H, 5.44; N, 11.90.

10-(4-Pyrrolidin-1-yl-piperidin-1-ylmethyl)-2H-7-oxa-1,2-diaza-benzo[de]anthracen-3-one (48)

Prepared from the compound 41 and 4-(1-pyrrolidinyl)piperidine according to General Procedure A and B. Purification of compound by crystallization in ethanol gave a white solid product 48. MS (ES+): 403; Mp 258-264 C; $^1$H-NMR (CDCl$_3$, 400 MHz): 9.93 (s, 1H), 8.06 (m, 2H), 7.81 (t, J=8.0 Hz, 1H), 7.55 (dd, J=8.0, 1.0 Hz, 1H), 7.50 (dd, J=8.0, 2.5 Hz, 1H), 7.26 (d, J=8.0 Hz, 1H), 3.55 (s, 2H), 2.90 (m, 2H), 2.61 (m, 4H), 2.06 (m, 2H), 1.87-1.62 (m, 9H). Anal. Calcd. for $C_{24}H_{26}N_4O_2$·(0.5H$_2$O): C, 70.05; H, 6.61; N, 13.62. Found: C, 70.25; H, 6.42; N, 13.59.

EXAMPLE 10

Preparation of diazabenzo[de]anthracen-3-one Derivatives 49-55 (Scheme 10)

10-Aminomethyl-2H-7-oxa-1,2-diaza-benzo[de]anthracen-3-one (49). To a solution of 7-bromomethyl-9-oxoxoanthese-1-carboxylic acid methyl ester 41 (0.70 g, 2.0 mmol) in anhydrous DMF (10 mL) was added Potassium phthalimide (0.44 g, 2.4 mmol). The reaction mixture was stirred under reflux for 3 hours, then cooled and the solvent was removed in vacuo. To the residue was added 100 mL of ethyl acetate and washed with water and brine, then dried with MgSO$_4$. The solvent was removed in vacuo to afford a white solid (0.53 g, 63%). The white solid (0.53 g) was dissolved in hydrazine (5 mL) and ethanol (10 mL) solution. The reaction mixture was stirred under reflux for 3 hours. Solution was concentrated in vacuo. To the concentrated solution was added water. A white precipitate was form and filtered out. The white solid was dried to afford compound 49 (0.30 g, 87%). MS (FAB (M+1)): 266; $^1$H-NMR (DMSO-d$_6$, 400 MHz): 12.60 (sb, 1H), 8.04 (d, J=2.0 Hz, 1H), 7.92-7.80 (m, 2H), 7.68 (dd, J=7.5 and 2.0 Hz, 1H), 7.50 (dd, J=8.5 and 2.0 Hz, 1H), 7.34 (d, J=8.5 Hz, 1H), 3.76 (s, 2H); Anal. Calcd. for $C_{15}H_{11}N_3O_2$: C, 67.92; H, 4.18; N, 15.84. Found: C, 67.67; H, 4.20; N, 15.64.

N-(3-Oxo-2,3-dihydro-7-oxa-1,2-diaza-benzo[de]anthracen-10-ylmethyl)-guanidine (50)

To the solution of 49 (0.10 g, 0.38 mmol) in DMF (5 mL) was added diisopropyl ethylamine (0.83 mmol) and 1H-pyrazole carboxamidine hydrochloride (0.12 g, 0.81 mmol). The reaction mixture was stirred at room temperature overnight. Diethyl ether was added to form a white precipitate. The precipitate was collected and recrystallized in EtOAc to afford a white solid 50 (0.1 μg, 83%, HCl salt). MS (ES−): 306; $^1$H-NMR (DMSO-d$_6$, 400 MHz): 12.62 (s, 1H), 8.04 (d, J=2.0 Hz, 1H), 7.92-7.84 (m, 2H), 7.71 (dd, J=7.5 and 2.0 Hz, 1H), 7.50 (dd, J=8.5 and 2.0 Hz, 1H), 7.45 (d, J=8.5 Hz, 1H), 4.47 (s, 2H); Anal. Calcd. for $C_{16}H_{13}N_5O_2$·1ClH: C, 55.58; H, 4.27; N, 19.76; Cl, 10.38. Found: C, 55.94; H, 4.17; N, 19.32; Cl, 10.12.

General Procedure C

To a solution of compound 49 in organic solvents (such as DMF, Dioxane) was added anhydride or acid chloride. The reaction mixture was stirred at various temperature. The solvents was removed in vacuo and the products was purified by recrystallization.

2,3-Diacetoxy-N-(3-oxo-2,3-dihydro-7-oxa-1,2-diaza-benzo[de]anthracen-10-ylmethyl)-succinamic acid (51). To the solution of compound 49 (0.20 g, 0.76 mmol) in Dioxane (20 mL) was added diacetyl tartaric anhydride (0.17 g, 0.80 mmol). The reaction mixture was stirred at room temperature overnight. The solvent was removed in vacuo. The residue was recrystallized in CH$_2$Cl$_2$. A white solid 51 was afforded in 95% yield. MS: (ES+): 482; $^1$H-NMR (DMSO-d$_6$, 400 MHz): 12.66 (s, 1H), 8.86 (d, J=6.2 Hz, 1H), 7.99 (s, 1H), 7.92-7.86 (m, 2H), 7.70 (dd, J=7.5 and 2.0 Hz, 1H), 7.40-7.36 (m, 2H), 5.56 (d, J=2.5 Hz, 1H), 5.51 (d, J=2.5 Hz, 1H), 4.45 (dd, J=15.0 and 6.3 Hz, 1H), 4.29 (dd, J=15.0 and 6.3 Hz, 1H), 2.14 (s, 3H), 1.98 (s, 3H); Anal. Calcd. for $C_{23}H_{19}N_3O_9$·(1.2H$_2$O): C, 54.92; H, 4.29; N, 8.35. Found: C, 54.89; H, 3.82; N, 8.39.

2,3-Dihydroxy-N-(3-oxo-2,3-dihydro-7-oxa-1,2-diaza-benzo[de]anthracen-10-ylmethyl)-succinamic acid (52). Compound 51 was dissolved in a solution of NaOH (2.5 equivalent) in H$_2$O/Dioxane. The reaction mixture was stirred overnight at 40° C., then was acidified to pH=3. Aqueous layer was extracted with ethyl acetate. Organic layer was dried with MgSO$_4$. Solvent was removed in vacuo to afford a white solid 52 in 25% yield. MS: (ES+): 398; Mp: 181-185° C.; $^1$H-NMR (DMSO-d$_6$, 400 MHz): 12.54 (s, 1H), 8.32 (t, J=6.2 Hz, 1H), 7.93 (d, J=2.0 Hz, 1H), 7.90-7.80 (m, 2H), 7.62 (dd, J=7.5 and 2.0 Hz, 1H), 7.40 (dd, J=8.5 and 2.0 Hz, 1H), 7.25 (d, J=8.5 Hz, 1H), 4.30-4.19 (m, 4H); Anal. Calcd for $C_{19}H_{15}N_3O_7$·(3H$_2$O): C, 50.56; H, 4.69; N, 9.31. Found: C, 50.59; H, 4.07; N, 9.28.

Pyrrolidine-2-carboxylic acid (3-oxo-2,3-dihydro-7-oxa-1,2-diaza-benzo[de]anthracen-10-ylmethyl)-amide (53). To a solution of compound 49 (0.5 mmol) in DMF was added triethylamine (0.6 mmol) and Fmoc-L-Proline chloride (0.6 mmol) slowly. The reaction mixture was stirred at room temperature for 3 hours. Water was poured into the reaction mixture. A white precipitate was formed and collected through filtration. The white solid was recrystallized to afford a white solid in 65% yield. The white solid was dissolved in 20% piperidine in DMF. The solution was stirred at room temperature for 2 hours. Water was added to the solution. Aqueous layer was extracted with ethyl acetate. Organic layer was collected, washed with brine, and dried. Solvent was removed to afford a white solid 53 in 54% yield. MS (ES+): 363; $^1$H-NMR (DMSO-d$_6$, 400 MHz): 12.64 (s, 1H), 8.59 (t, J=5.8 Hz, 1H), 7.98 (d, J=2.0 Hz, 1H), 7.90-7.82 (m, 2H), 7.72 (dd, J=7.5 and 2.0 Hz, 1H), 7.43 (dd, J=8.5 and 2.0 Hz, 1H), 7.36 (d, J=8.5 Hz, 1H), 4.35 (d, J=3.8 Hz, 2H), 3.62 (m, 1H), 2.98 (t, J=5.2 Hz, 1H), 2.87 (m, 1H), 1.99 (m, 1H), 1.73 (m, 1H), 1.64 (m, 2H); Anal. Calcd. for $C_{20}H_{18}N_4O_3$·(1.2$H_2O$): C, 62.56; H, 5.35; N, 14.59. Found: C, 62.75; H, 5.34; N, 14.52.

(3-Oxo-2,3-dihydro-7-oxa-1,2-diaza-benzo[de]anthracen-10-ylmethyl)-phosphoramidic acid diethyl ester (54). To a solution of compound 49 (0.5 mmol) in anhydrous DMF (20 mL) was added diethyl chlorophosphate (1.5 mmol). After 3 hours solution was concentrated in vacuo, and 50 mL of water was added. The aqueous layer was extracted with 30 mL of EtOAc twice. Organic layers were combined and washed with 30 mL of brine. Organic layer was dried with MgSO$_4$. Solvent was removed to afford a white solid, which was recrystallized in 10% of EtOAc in hexanes to afford a white solid 54 in 50% yield. MS (ES−): 400; Mp: 222.3-224.5° C.; $^1$H-NMR (CDCl$_3$, 400 MHz): 10.21 (s, 1H), 8.10 (d, J=2.5 Hz, 1H), 8.03 (d, J=7.5 Hz, 1H), 7.79 (t, J=8.0 Hz, 1H), 7.52 (d, J=8.0 Hz, 1H), 7.47 (dd, J=8.5 and 2.0 Hz, 1H), 7.22 (d, J=8.5 Hz, 1H), 4.12 (m, 6H), 1.32 (t, J=6.5 Hz, 6H); Anal. Calcd. for $C_{19}H_{20}N_3O_5P$·(0.3$H_2O$): C, 56.10; H, 5.10; N, 10.33. Found: C, 56.00; H, 5.03; N, 10.13.

4-(4-Dimethylamino-phenylazo)-N-(3-oxo-2,3-dihydro-7-oxa-1,2-diaza-benzo[de]anthracen-10-ylmethyl)-benzenesulfonamide (55). To a solution of compound 49 (0.5 mmol) in anhydrous DMF (20 mL) was added 4-dimethylaminoazobenzene-4'-sulfonyl chloride (0.5 mmol). The mixture was stirred for 3 hours at room temperature. The reaction mixture was concentrated in vacuo, and 50 mL of 50% EtOAc in hexanes was added. The precipitate was formed and collected through filtration. The crude product was recrystallized in 50% ethanol to afford a orange solid 55 in 59% yield. MS (ES+): 553; Mp: >300° C.; $^1$H-NMR (DMSO-d$_6$, 400 MHz): 12.63 (s, 1H), 7.90 (d, J=2.0 Hz, 1H), 7.86-7.74 (m, 6H), 7.67 (d, J=9.0 Hz, 2H), 7.62 (dd, J=6.6 and 2.5 Hz, 1H), 7.44 (dd, J=8.5 and 2.0 Hz, 1H), 7.30 (d, J=8.5 Hz, 1H), 6.81 (d, J=9.0 Hz, 2H), 4.15 (s, 2H), 3.09 (s, 6H); Anal. Calcd. for $C_{29}H_{24}N_6O_4S$·(1.3$H_2O$): C, 60.47; H, 4.65; N, 14.59; S, 5.57. Found: C, 60.72; H, 4.93; N, 15.39; S, 4.93.

EXAMPLE 11

Preparation of diazabenzo[de]anthracen-3-one Derivatives 56-61 (Scheme 11)

10-Aminooxymethyl-2H-7-oxa-1,2-diaza-benzo[de]anthracen-3-one (56). To a solution of hydroxy phthalimide (3.6 mmol) in anhydrous DMF was added sodium anhydride 60% in mineral oil (3.6 mmol). The solution was stirred for 20 minutes at room temperature. To this solution was added compound 41 (3.0 mmol). The reaction mixture was stirred at room temperature for two hours and the solvent was removed in vacuo. To the residue was added 100 mL of ethyl acetate. The organic layer was washed with water and brine, then dried over MgSO$_4$. Ethyl acetate was removed in vacuo. A white solid was afforded in 70% yield. The white solid was added to a mixture of hydrazine and ethyl alcohol. The mixture was stirred for 2 hours under reflux. The solution was concentrated down in vacuo. To the concentrated solution was added water. A white precipitate was formed, filtered out, and washed with extra water. The white solid was collected and dried to give a white solid product 56 in 85% yield. MS (ES+): 282; Mp: 294-296° C.; $^1$H-NMR (DMSO-d$_6$, 400 MHz): 12.64 (s, 1H), 8.04 (d, J=2.0 Hz, 1H), 7.92-7.86 (m, 2H), 7.73 (dd, J=7.5 and 2.0 Hz, 1H), 7.50 (dd, J=8.5 and 2.0 Hz, 1H), 7.41 (d, J=8.5 Hz, 1H), 4.64 (s, 2H); MS: (ES+): 282; Anal. Calcd. for $C_{15}H_{11}N_3O_3$: C, 64.05; H, 3.94; N, 14.94. Found: C, 64.24; H, 4.00; N, 14.97.

10-Hydroxymethyl-2H-7-oxa-1,2-diaza-benzo[de]anthracen-3-one (57). To a solution of compound 41 (4.2 mmol) in 20 mL of water and 20 mL of acetone was added silver nitrate (8.4 mmol). The reaction mixture was stirred at 50° C. for 2 hours. Black precipitate was filtered out. The filtrate was concentrated in vacuo. To the residue was added 100 mL of ethyl acetate. The organic layer was washed with water and brine, then dried with MgSO$_4$. Solvents was removed in vacuo to afford a white solid in 86% yield. The white solid was added to a mixture of hydrazine and ethyl alcohol. The mixture was stirred for 2 hours under reflux. The solution was concentrated in vacuo. To the concentrated solution was added water. A white precipitate was formed, filtered out, and washed with extra water. The white solid was collected and dried to give a white solid product 57 in 95% yield. MS (ES+): 267, $^1$H-NMR (DMSO-d6, 400 MHz): 12.56 (s, 1H), 7.99 (d, J=2.0 Hz, 1H), 7.91-7.81 (m, 2H), 7.63 (dd, J=7.5 and 2.0 Hz, 1H), 7.43 (dd, J=8.5 and 2.0 Hz, 1H), 7.30 (d, J=8.5 Hz, 1H), 4.50 (d, J=6.0 Hz, 2H); Anal. Calcd. for $C_{15}H_{10}N_2O_3$·(0.08hydrazine): C, 67.02; H, 3.87; N, 11.25. Found: C, 67.29; H, 3.82; N, 11.51.

General Procedure D

To a solution of compound 57 in organic solvents (such as DMF, Dioxane) was added anhydride or acid chloride. The reaction mixture was stirred at various temperature. The solvents was removed in vacuo and the products was purified by recrystallization.

[2-(3-Oxo-2,3-dihydro-7-oxa-1,2-diaza-benzo[de]anthracen-10-ylmethoxy)-ethyl]-phosphonic acid dibenzyl ester (58). To a solution of dibenzylphosphite (2.6 mmol) in 10 mL of THF was added ethyl acrylate (3.0 mmol), $K_2CO_3$ (16 mmol), and 0.3 mL of (Bn4NH)$_2$SO$_4$ 50% w/w. The reaction mixture was stirred at 45° C. overnight. Water was added. The aqueous layer was extracted with ethyl acetate. Organic layer was collected and dried with MgSO$_4$. Solvent was removed to afford a clear oil 3-bis(benzyloxy)phosphorylpropanoic acid in 90% yield. $^1$H-NMR (CDCl$_3$, 400 MHz): 7.33 (m, 10H), 4.90-5.10 (m, 4H), 3.61 (s, 3H), 2.50-2.60 (m, 2H), 2.00-2.15 (m, 2H).

To a solution of compound 57 (0.5 mmol) in anhydrous DMF was added 3-bis(benzyloxy)phosphorylpropanoic acid (0.75 mmol) and EDC (0.75 mmol) and DMAP (catalytic amount). The reaction mixture was stirred at room temperature overnight. Solvent was removed in vacuo. To the residue, 100 mL ethyl acetate was added. The organic layer was washed with water, and dried with MgSO$_4$. Solvent was removed to afford a colorless oil, which was recrystallized in EtOAc/Hexanes to afford a white solid 58 in 40% yield. MS (ES−): 581; Mp: 173-175° C. $^1$H-NMR (CDCl$_3$, 400 MHz): 10.01 (s, 1H), 8.11 (d, J=2.0 Hz, 1H), 8.07 (d, J=7.5 Hz, 1H), 7.82 (t, J=8.5 Hz, 1H), 7.54 (d, J=8.0 Hz, 1H), 7.40 (dd, J=8.5 and 2.0 Hz, 1H), 7.35-7.22 (m, 11H), 5.09 (s, 2H), 4.98 (m, 4H), 2.62 (m, 2H), 2.12 (m, 2H); Anal: Calcd for $C_{32}H_{27}N_2O_7P$: C, 65.98; H, 4.67; N, 4.81. Found: C, 65.69; H, 4.82; N, 5.09.

Dimethylamino-acetic acid 3-oxo-2,3-dihydro-7-oxa-1,2-diaza-benzo[de]anthracen-10-ylmethyl ester (59). To a solution of compound 57 (0.5 mmol) in anhydrous DMF was added dimethyl glycine (0.75 mmol) and EDC (0.75 mmol) and DMAP (catalytic amount). The reaction mixture was stirred at room temperature overnight. Solvent was removed in vacuo. To the residue, 100 mL of ethyl acetate was added. The organic layer was washed with water, and brine, then dried with MgSO$_4$. The Solvents were removed to afford a colorless oil, which was re-crystallized in EtOAc/Hexanes to afford an off-white solid 59 in 30% yield. MS (ES+): 352; MP: 227-230° C.; $^1$H-NMR (CDCl$_3$, 400 MHz): 10.15 (s, 1H), 8.14 (d, J=2.0 Hz, 1H), 8.06 (dd, J=8.0 and 1.0 Hz, 1H), 7.80 (t, J=8.0 Hz, 1H), 7.53 (dd, J=8.0 and 1.0 Hz, 1H), 7.47 (dd, J=8.5 and 2.0 Hz, 1H), 7.22 (d, J=8.5 Hz, 1H), 5.21 (s, 2H), 3.26 (s, 2H), 2.37 (s, 6H); Anal. Calcd. for C$_{19}$H$_{17}$N$_3$O$_4$: C, 64.95; H, 4.86; N, 11.96. Found: C, 64.95; H, 4.78; N, 12.14.

Phosphoric acid dibenzyl ester 3-oxo-2,3-dihydro-7-oxa-1,2-diaza-benzo[de]anthracen-10-ylmethyl ester (60). To a solution of compound 57 (0.25 mmol) in anhydrous DMF was added dibenzyl phosphate (0.80 mmol) and triphenylphosphine (0.80 mmol). The reaction mixture was stirred while diisopropyl azodicarboxylate was added slowly. The reaction mixture was stirred at room temperature for 3 hours. Solvent was removed in vacuo. To the residue, 100 mL of ethyl acetate was added. The organic layer was washed with water and brine, then dried with MgSO$_4$. The Solvents were removed to afford a yellow oil. The oil was re-crystallized in EtOAc/Hexanes to afford an off-white solid 60 in 40% yield. MS (ES+): 527; Mp: 223-225° C.; $^1$H-NMR (CDCl$_3$, 400 MHz): 9.91 (s, 1H), 8.13 (d, J=2.0 Hz, 1H), 8.11 (dd, J=8.0 and 1.0 Hz, 1H), 7.85 (t, J=8.0 Hz, 1H), 7.59 (dd, J=8.0 and 1.0 Hz, 1H), 7.45 (dd, J=8.5 and 1.0 Hz, 1H), 7.36-7.26 (m, 11H), 5.08 (m, 6H). Anal. Calcd. for C$_{29}$H$_{23}$N$_2$O$_6$P.(0.15 hydrazine): C, 65.56; H, 4.48; N, 6.06. Found: C, 65.55; H, 4.33; N, 6.09.

Phosphoric acid mono-(3-oxo-2,3-dihydro-7-oxa-1,2-diaza-benzo[de]anthracen-10-ylmethyl)ester (61). To a solution of compound 57 (0.25 mmol) in anhydrous DMF was added 1H-tetrazole (2.5 mmol) and di-tert-butyl N,N-diethylphosphoramidite (1.25 mmol). The reaction mixture was stirred at room temperature for 2 hours. To the solution was added t-butyl hydroperoxide. The reaction mixture was stirred for another one hour. The reaction mixture was cooled to 0° C. and 15 ml of 15% NaHSO$_3$ solution in water was added to the reaction mixture. The mixture was stirred for another 15 minutes. The mixture was neutralized to pH=8.5 and extracted with ethyl acetate. Organic layer was collected, washed with brine and dried over MgSO$_4$. The Solvents were removed in vacuo to afford an off-white solid, which was re-crystallized in EtOAc/hexanes to give the intermediate in 78% yield.

The off-white solid was dissolved in 10 mL of CH$_2$Cl$_2$ and 4 mL of TFA was added to the solution. The reaction mixture was stirred at room temperature for 3 hours. Solvent was removed in vacuo. Residue was re-crystallized in ethyl acetate to afford a yellow solid 61 in 60% yield. MS (ES+): 347; Mp: 246-252° C. $^1$H-NMR (DMSO-d$_6$, 400 MHz): 12.64 (s, 1H), 8.09 (s, 1H), 7.93-7.85 (m, 2H), 7.67 (dd, J=7.0 and 2.0 Hz, 1H), 7.53 (dd, J=8.5 and 2.0 Hz, 1H), 7.41 (d, J=8.0 Hz, 1H), 4.95 (d, J=7.5 Hz, 2H); Anal. Calcd. for C$_{15}$H$_{11}$N$_2$O$_6$P: C, 52.04; H, 3.2; N, 8.09. Found: C, 51.76; H, 3.38; N, 8.21.

EXAMPLE 12

Focal Cerebral Ischemia Effect of 10-(4-Methyl-piperazin-1-ylmethyl)-2H-7-oxa-1,2-diaza-benzo[de]anthracen-3-one (43)

Rats are allowed free access to water and rat chow (Wayne, Chicago, Ill.) until surgery. Housing and anesthesia concur with guidelines established by the institutional Animal Studies Committee, and are in accordance with the PHS Guide for the Care and Use of Laboratory Animals, USDA Regulations, and the AVMA Panel on Euthanasia guidelines.

The animals are anesthetized with isofluorane (induction, 3%; maintenance, 1.25% in a O$_2$) through a face mask. During the brief surgeries, animals were kept warm on a heating blanket. An iv catheter is inserted into the left femoral vein for administration of drugs. The right middle cerebral artery (MCA) is then exposed by making a vertical skin incision midway between the right eye and ear and the overlying skull is removed with a dental drill. For transient occlusion, a Codman microclip is applied to the artery at the level of inferior cerebral vein. For permanent occlusion of the MCA, the artery is coagulated at the level of the inferior cerebral vein with a bipolar cautery unit (Valleylab NS2000, Boulder, Colo.), and cut to prevent spontaneous reperfusion. Both common carotid arteries (CCAs) that had been previously isolated and freed of soft tissues and nerves are then ligated using non-traumatic aneurysm clips. After the wounds are closed with surgical clips, the animals are allowed to recover from anesthesia and returned to their cage in a room warmed to 27° C.

For the Pre-Post dosing strategy drugs are first administered as an iv bolus 30 min before MCAO and then 30 min before reperfusion, i.e., one hour post-MCAO. Ninety minutes after the MCAO, the animals are briefly reanesthetized with isofluorane, and the carotid clips are removed. The animal is returned to the warm room overnight.

At 24 hrs after either transient or permanent MCAO, animals are killed with CO$_2$ and the heads removed by guillotine. Brains are removed, cooled in ice-cold saline, and sliced into 2 mm coronal sections using a rat brain matrice (Harvard Bioscience, South Natick, Mass.). The brain slices are incubated in phosphate-buffered saline (pH 7.4) containing 2% TTC at 37° C. for 10 min. and then stored in 10% neutral-buffered formalin. Cross-sectional area of the TTC-unstained region for each brain slice is determined using an image analyzer (MetaMorph, Universal Imaging Corp., West Chester, Pa.). The total volume of infarction in the right hemisphere is calculated by summation of the direct (TTC-negative). The infarcted volumes in vehicle and drug-treated groups (n=8) are tested for significant statistical difference using an unpaired Student-t test (FIG. 1).

EXAMPLE 13

Myocardial Protection of 10-(4-Methyl-piperazin-1-ylmethyl)-2H-7-oxa-1,2-diaza-benzo[de]anthracen-3-one (43)

In the present study, we investigated the effects of 43 in the regional heart ischemia reperfusion model. In regional heart ischemia model, sodium thiopental-anaesthetized male SD rats were subjected to occlusion of LAD coronary artery for 30 min followed by 2 hr of reperfusion. The infarct size was quantified by TTC staining method and expressed as percent of area at risk. Administration of 43 iv. bolus pre-ischemia plus another iv. bolus post-ischemia exerts significant cardiac protection in a dose range from 10 to 40 mg/kg.

The reperfusion injury caused by free radicals is not limited to cerebral ischemia. It also contributes significantly to damage of other organs including the heart and skeletal muscle. It has been demonstrated that PARP inhibitors reduce the infarct size caused by ischemia and reperfusion of heart and skeletal muscle of the rabbit. Evidence suggests that the reperfusion injury for cerebral and myocardial ischemia may have a common mechanism in that both injuries are due to PARP activation as a result of DNA damage by free radicals. Transient inhibition of PARP activity is a novel approach for the therapy of ischemia-reperfusion injury of the heart.

The left anterior descending coronary artery of Sprague-Dawley rats was occluded for 30 minutes. This was followed by 90-120 minutes of blood reflow. PARP inhibitor compounds were given intraperitoneally (ip), 60 minutes pre-, or intravenously (iv), 15 or 5 minutes pre- and 25 minutes post-onset of ischemia. Infarct size was determined by TTC staining and the risk area was determined via blue dye injection.

PARP inhibitors exhibited significant reduction in infarct size in this model, that is it reduced the infarct volume by between 36%, p=0.001.

EXAMPLE 14

10-(4-Methyl-piperazin-1-ylmethyl)-2H-7-oxa-1,2-diaza-benzo[de]anthracen-3-one (43) enhances in vitro sensitivity of melanoma, lymphoma and glioblastoma multiforme cell lines to TMZ Cell Lines The murine melanoma cell line B16 of C57BL/6J ($H-2^b/H-2^b$) origin and the lymphoma cell line L5178Y of DBA/2 ($H-2^d/H-2^d$) origin (ATCC, Manassas, Va.) were cultured in RPMI-1640 containing 10% fetal calf serum (Invitrogen, Milan, Italy), 2 mM L-glutamine, 100 units/ml penicillin and 100 µg/ml streptomycin (Flow Laboratories, Mc Lean, Va.), at 37° C. in a 5% $CO_2$ humidified atmosphere. The human glioblastoma multiforme cell line SJGBM2 was cultured in DMEM (Invitrogen) supplemented with 10% fetal calf serum, 2 mM L-glutamine and antibiotics. SJGBM2 cell line was a kind gift from Dr. Peter J. Houghton (St. Jude Children's Research Hospital, Memphis, Tenn., USA).

Drugs

TMZ was provided by Schering-Plough Research Institute (Kenilworth, N.J., USA. Drug stock solutions were prepared by dissolving TMZ in dimethyl sulfoxide and 43 in 70 mM PBS without potassium.

In Vitro Studies

Cells were treated with 43 (0.1-20 µM) or with TMZ (1-250 µM). For the experiments aimed at assessing the enhancing effect of 43 on TMZ-induced tumor growth inhibition, the methylating agent was added to cell cultures 15 min after 43 was used at concentrations non-toxic, and capable of abrogating PARP activity. The final concentration of dimethyl sulfoxide was always less than 0.1% (v/v) and did not contribute to toxicity (data not shown).

Cells were cultured for three days and apoptosis or cell cycle analysis were evaluated daily by flow-cytometry analysis of DNA content as previously described (Tentori 1997). Briefly, cells were washed with PBS and fixed in 70% ethanol at −20° C. for 18 h. The centrifuged pellets were resuspended in 1 ml of hypotonic solution containing propidium iodide (50 µg/ml), 0.1% sodium citrate, 0.1% Triton-X, and RNase (10 µg/ml) and incubated in the dark, at 37° C. for 15 min. Data collection was gated utilizing forward light scatter and side light scatter to exclude cell debris and aggregates. The propidium iodide fluorescence was measured on a linear scale using a FACSscan flow cytometer (Becton and Dickinson, San Jose, Calif., USA). All data were recorded and analyzed using Cell Quest software. For cell cycle analysis the Mod-fit software was used (Becton and Dickinson).

Long-term survival was analyzed by colony-formation assay. Exponentially growing melanoma and glioblastoma cells were seeded into 6-well plates at a density of $2 \times 10^2$/well and left to attach for 18 h; cells were then treated with the compounds under study and cultured to allow colony formation. After 10 days, colonies (defined as a cluster of >50 cells) were fixed and stained with rhodamine B basic violet 10 (ICN Biomedicals Inc., Aurora, Ohio, USA). Untreated or treated lymphoma cells were seeded at 1 cell/well in 96-well plates (flat-bottomed) and cultured. After 10 days, colonies were counted to determine cloning efficiency, using an optical microscope (Tentori 2001b).

Cell line chemosensitivity to TMZ, 43 or to the drug combination was evaluated in terms of $IC_{50}$, i.e. the concentration of the drug expressed in µM, capable of inhibiting colony-forming ability by 50%. The $IC_{50}$ was calculated on the regression line in which the number of colonies was plotted vs the drug concentration.

In Vivo Studies

The intracranial transplantation procedure was performed as previously described (Tentori 2002b). Cells ($10^4$ in 0.03 ml of RPMI-1640) were injected intra-cranially (ic) through the center-middle area of the frontal bone to a 2 mm depth, using a 0.1 ml glass microsyringe and a 27-gauge disposable needle.

Murine melanoma B16 or lymphoma L5178Y cells ($10^4$) were injected ic into male B6D2F1 (C57BL/6×DBA/2) mice. Human glioblastoma multiforme SJGBM2 cells ($10^6$) were injected ic into male athymic BALB/c mice (nu/nu genotype). Before tumor challenge, animals were anesthetized with ketamine (100 mg/kg) and xylazine (5 mg/kg) in 0.9% NaCl solution (10 ml/kg/ip).

Histological evaluation of tumor growth in the brain was performed 1-5 days after tumor challenge, in order to select the timing of treatment. Brains were fixed in 10% phosphate-buffered formaldehyde, cut along the axial plane and embedded in paraffin. Histological sections (5 µm thick) were stained with hematoxylin-eosin and analyzed by light microscopy.

Drug toxicity was evaluated by treating intact mice (5/group) with the compounds under study, used as single agents or in combination. Control groups were treated with vehicles only. Body weight was measured three times weekly and survivals were recorded for 3 weeks after the last treatment. Toxicity was assessed on the basis of apparent drug-related deaths and net body weight loss [i.e., (initial weight−lowest weight/initial weight)×100%]. Death was considered drug-related when occurring within 7 days after the last treatment.

43 was dissolved in 70 mM PBS without potassium, and injected intravenously (iv) at different doses (40-200 mg/kg) to establish the maximal tolerated dose.

TMZ was dissolved in dimethyl-sulfoxide (40 mg/ml), diluted in saline (5 mg/ml) and administered ip at doses commonly used for in vivo preclinical studies (Friedman 1995; Middleton 2000; Kokkinakis 2001). Experiments were performed using different doses and schedules of TMZ+43 to determine the maximal tolerated dose of the drug combination. 43 was administered 15 min before TMZ administration. Control mice were always injected with drug vehicles.

In tumor-bearing mice treatment was started on day 2 after challenge, when tumor infiltration in the surrounding brain tissue was histologically evident. Since the antitumor activity of TMZ and PARP inhibitors can be improved by fractionated modality of treatment (Tentori 2002b), the maximal tolerated dose of the drug combination was divided into daily administrations of 100 mg/kg TMZ+40 mg/kg 43 for 3 days.

Mice were monitored for mortality for 90 days. Median survival times (MST) were determined and the percentage of increase in lifespan (ILS) was calculated as: {[MST (days) of treated mice/MST (days) of control mice]−1}×100. Efficacy of treatments was evaluated by comparing survival curves between treated and control groups.

To assess the ability of different treatments to reduce tumor growth, histological examination of the brains was performed using additional animals that were not considered for the analysis of survival. Mice were sacrificed at different time points after tumor challenge, selected within the MST range of untreated tumor-bearing animals.

The efficacy of TMZ±43 treatment was also evaluated on melanoma growing subcutaneously (sc). For this purpose B16 cells ($2.5 \times 10^5$) were inoculated sc in the flank of the animal. Tumors were measured with calipers and volume calculated according to the formula: $[(width)^2 \times length]/2$. Treatment was started 6 days after challenge, when the volume of tumor nodules reached 100-150 mm$^3$. Melanoma growth was monitored, by measuring tumor nodules every 3 days for 3 weeks.

To evaluate the influence of the drugs under study on generation of artificial metastases, B16 cells ($2.5 \times 10^5$ in 0.02 ml) were injected into the tail vein of B6D2F1 mice. Animals were treated with the drugs under study using the 3-days schedule (see above). Two weeks after tumor challenge, animals were sacrificed, lungs removed and fixed in Bouin's solution to distinguish tumor nodules from lung tissue. The number of metastases was determined using a dissecting microscope.

All procedures involving mice and care were performed in compliance with national and international guidelines (European Economy Community Council Directive 86/109, OLJ318, Dec. 1, 1987 and NIH Guide for care and use of laboratory animals, 1985.)

Statistical Analysis

Survival curves were generated by Kaplan-Meier product-limit estimate and statistical differences between the various groups were evaluated by log-rank analysis (software Primer of Biostatistics, McGraw-Hill, New York, N.Y.). For statistical analysis of tumor growth or metastasis number, the significance of the differences between experimental groups was evaluated by t test. Ps are two-sided (software Microsoft excel).

Initially B16, SJGBM2 and L5178Y cells were exposed to 1-25 μM 43, as single agent. Cell growth was analysed by colony formation assay and the results indicated that 43 exhibited some intrinsic growth inhibition and that B16 melanoma was more susceptible to the antiproliferative effect induced by 43 with respect to SJGBM2 and L5178Y cell lines.

For each cell line 43 concentrations devoid of toxic effects (0.3-1.2 μM) were tested for their ability to enhance growth inhibition induced by TMZ. In all tumor cell lines, the PARP inhibitor increased growth inhibition induced by TMZ. In the case of B16 cell line, the maximal enhancement of TMZ-induced growth inhibition was achieved at 0.6 μM concentration (10-fold). In B16 cells, 43 at the concentration of 1.2 μM induced 18±3% growth inhibition with respect to control and was not considered for combination studies with TMZ. For SJGBM2 and L5178Y cell lines, the maximal increase of TMZ growth inhibitory effect was observed at 1.2 μM 43 (~4-fold for SJGBM2 and ~10-fold for L5178Y, respectively). In SJGBM2 and L5178Y cell lines 2.5 μM 43 showed intrinsic growth inhibitory effect, therefore this concentration was not tested in association with TMZ.

In B16 and SJGBM2 cells TMZ+43 mainly provoked cytostasis without induction of apoptosis, while in L5178Y lymphoma cells the drug combination induced also apoptosis (data not shown).

EXAMPLE 15

Systemic administration of 10-(4-Methyl-piperazin-1-ylmethyl)-2H-7-oxa-1,2-diaza-benzo[de]anthracen-3-one (43)+TMZ enhances survival of mice bearing melanoma, lymphoma or glioblastoma multiforme at the CNS site The antitumor activity of the drug combination, at the highest tolerable dose (TMZ 100 mg/kg/day ip+43 40 mg/kg/day iv, for 3 days), was initially tested in B16 melanoma growing subcutaneously in B6D2F1 mice and compared to the effects induced by TMZ or 43 used as single agents. The results show that 43 significantly enhanced ($P<0.0001$) the antitumor effects of TMZ, while treatment with 43 only, did not affect tumor growth.

The same drug schedule was used to investigate whether systemic administration of 43, which is capable of crossing the blood-brain barrier, might increase efficacy of TMZ also against B16 melanoma growing at the CNS site. Drug treatment was started 2 days after tumor challenge, when neoplastic infiltration of the brain tissue was evidenced in histological sections. The results show that the increase in survival time induced by 43+TMZ combination was significantly higher ($P<0.0001$) than that provoked by TMZ as single agent. The increase in survival detected in the group treated with the drug combination was accompanied by a marked reduction of tumor growth. Histological studies revealed a pronounced and diffuse tumor infiltration in the brain of control or 43 treated mice, limited but multifocal infiltration in TMZ-treated mice, whereas only few infiltrating melanoma cells in 43+TMZ treated animals.

The PARP inhibitor 43 also increased the anti-metastatic activity of TMZ against B16 melanoma. In fact, the number of pulmonary metastases observed after treatment with 43+TMZ was significantly lower ($P=0.004$) than that detected in mice treated with TMZ used as single agent.

Systemic administration of 43+TMZ significantly increased survival of B6D2F1 mice bearing L5178Y lymphoma growing in the brain. The increase in median survival time induced by the drug combination was significantly higher than that provoked by TMZ used as single agent.

The efficacy of drug treatment was then investigated using an orthotopic model of a human glioblastoma multiforme xenograft in nude mice. The results indicate that systemic administration of 43+TMZ significantly prolonged survival of tumor bearing mice with respect to controls or to animals treated with the single agents. It should be noted that in this tumor model TMZ was completely ineffective.

Microscopic examination of control animals injected with SJGBM2 revealed multifocal brain involvement. Treatment with 43+TMZ resulted in a decreased number of sites of neoplastic infiltration. In the control group, all animals presented tumor infiltration in at least two brain regions distant from the site of injection, whereas in the group treated with the drug combination only 2/7 mice showed this pattern (total brain regions infiltrated by tumor cells: control, 24; 43+TMZ: 13; $P=0.0007$). Moreover, brains of control mice showed large tumor masses both at the site of injection and in the parenchyma surrounding the ventricles; in contrast, animals treated with 43+TMZ showed minimal tumor infiltration.

EXAMPLE 16

Measuring Altered Gene Expression in mRNA Senescent Cells

Gene expression alteration may be measured with human fibroblast BJ cells which, at Population Doubling (PDL) 94, are plated in regular growth medium and then changed to low serum medium to reflect physiological conditions described in Linskens, et al., Nucleic Acids Res. 23:16:3244-3251 (1995). A medium of DMEM/199 supplemented with 0.5% bovine calf serum is used. The cells are treated daily for 13 days. The control cells are treated with and without the solvent used to administer the PARP inhibitor. The untreated old and young control cells are tested for comparison. RNA is prepared from the treated and control cells according to the techniques described in PCT Publication No. 96/13610 and Northern blotting is conducted. Probes specific for senescence-related genes are analyzed, and treated and control cells compared. In analyzing the results, the lowest level of gene expression is arbitrarily set at 1 to provide a basis for comparison. Three genes particularly relevant to age-related changes in the skin are collagen, collagenase and elastin. West, Arch. Derm. 130:87-95 (1994). Elastin expression of the cells treated with the PARP inhibitor is expected to be significantly increased in comparison with the control cells. Elastin expression should be significantly higher in young cells compared to senescent cells, and thus treatment with the PARP inhibitor should cause elastin expression levels in senescent cells to change to levels similar to those found in much younger cells. Similarly, a beneficial effect should be seen in collagenase and collagen expression with treatment with the PARP inhibitors.

EXAMPLE 17

Measuring Altered Gene Expression of Protein in Senescent Cells

Gene expression alteration may be measured with approximately 105 BJ cells, at PDL 95-100 which are plated and grown in 15 cm dishes. The growth medium is DMEM/199 supplemented with 10% bovice calf serum. The cells are treated daily for 24 hours with the PARP inhibitors of (100 µg/1 mL of medium) WO 99/11645. The cells are washed with phosphate buffered solution (PBS), then permeablized with 4% paraformaldehyde for 5 minutes, then washed with PBS, and treated with 100% cold methanol for 10 minutes. The methanol is removed and the cells are washed with PBS, and then treated with 10% serum to block nonspecific antibody binding. About 1 mL of the appropriate commercially available antibody solutions (1:500 dilution. Vector) is added to the cells and the mixture incubated for 1 hour. The cells are rinsed and washed three times with PBS. A secondary antibody, goat anti-mouse IgG (1 mL) with a biotin tag is added along with 1 mL of a solution containing streptavidin conjugated to alkaline phosphatase and 1 mL of NBT reagent (Vector). The cells are washed and changes in gene expression are noted calorimetrically. Four senescence-specific genes—collagen I, collagen III, collagenase, and interferon gamma—in senescent cells treated with the PARP inhibitor are monitored and the results should show a decrease in interferon gamma expression with no observable change in the expression levels of the other three gens, demonstrating that the PARP inhibitors can alter senescence-specific gene expression.

EXAMPLE 18

Extending or Increasing Proliferative Capacity and Lifespan of Cells

To demonstrate the effectiveness of the present method for extending the proliferative capacity and lifespan of cells, human fibroblast cells lines (either W138 at Population Doubling (PDL) 23 or BJ cells at PDL 71) are thawed and plated on T75 flasks and allowed to grow in normal medium (DMEM/M199 plus 10% bovine calf serum) for about a week, at which time the cells are confluent, and the cultures are therefor ready to be subdivided. At the time of subdivision, the media is aspirated, and the cells rinsed with phosphate buffer saline (PBS) and then trypsinized. The cells are counted with a Coulter counter and plated at a density of $10^5$ cells per cm$^2$ in 6-well tissue culture plates in DMEM/199 medium supplemented with 10% bovine calf serum and varying amounts (0.10 µM, and 1 mM: from a 100× stock solution in DMEM/M199 medium) of a PARP inhibitor. This process is repeated every 7 days until the cells appear to stop dividing. The untreated (control) cells reach senescence and stop dividing after about 40 days in culture. Treatment of cells with 10 µM 3-AB appears to have little or no effect in contrast to treatment with 100 µM 3-AB which appears lengthen the lifespan of the cells and treatment with 1 mM 3-AB which dramatically increases the lifespan and proliferative capacity of the cells. The cells treated with 1 mM 3-AB will still divide after 60 days in culture.

EXAMPLE 19

Neuroprotective Effects of PARP Inhibitors on Chronic Constriction Injury (CCI) in Rats Adult male Sprague-Dawley rats, 300-350 g, are anesthetized with intraperitoneal 50 mg/kg sodium pentobarbital. Nerve ligation is performed by exposing one side of the rat's sciatic nerves and dissecting a 5-7 mm-long nerve segment and closing with four loose ligatures at a 1.0-1.5-mm, followed by implanting of an intrathecal catheter and inserting of a gentamicin sulfate-flushed polyethylene (PE-10) tube into the subarachnoid space through an incision at the cisterna magna. The caudal end of the catheter is gently threaded to the lumbar enlargement and the rostral end is secured with dental cement to a screw embedded in the skull and the skin wound is closed with wound clips.

Thermal hyperalgesia to radiant heat is assessed by using a paw-withdrawal test. The rat is placed in a plastic cylinder on a 3-mm thick glass plate with a radiant heat source from a projection bulb placed directly under the plantar surface of the rat's hindpaw. The paw-withdrawal latency is defined as the time elapsed from the onset of radiant heat stimulation to withdrawal of the rat's hindpaw.

Mechanical hyperalgesia is assessed by placing the rat in a cage with a bottom made of perforated metal sheet with many small square holes. Duration of paw-withdrawal is recorded after pricking the mid-plantar surface of the rat's hindpaw with the tip of a safety pin inserted through the cage bottom.

Mechano-allodynia is assessed by placing a rat in a cage similar to the previous test, and applying von Frey filaments in ascending order of bending force ranging from 0.07 to 76 g to the mid-plantar surface of the rat's hindpaw. A von Frey filament is applied perpendicular to the skin and depressed slowly until it bends. A threshold force of response is defined as the first filament in the series to evoke at least one clear paw-withdrawal out of five applications.

Dark neurons are observed bilaterally within the spinal cord dorsal horn, particularly in laminae I-II, of rats 8 days after unilateral sciatic nerve ligation as compared with sham operated rats. Various doses of PARP inhibitors are tested in this model and shown to reduce both incidence of dark neurons and neuropathic pain behavior in CCI rats.

The invention being thus described, it will be obvious that the same may be varied in many ways. Such variations are not to be regarded as a departure from the spirit and scope of the invention, and all such modifications are intended to be included within the scope of the following claims. All references cited herein are incorporated in their entirety by reference herein.

What is claimed is:

1. A compound of the formula:

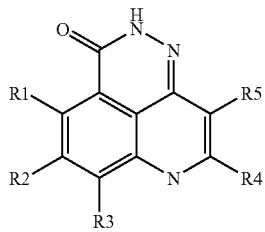

I or a pharmaceutically acceptable salt;
wherein:
R1 is H, halogen, alkoxy, or lower alkyl;
R2 is H, halogen, alkoxy, or lower alkyl;
R3 is independently H, amino, hydroxy, —NH—NH$_2$, halogen-substituted amino, —O-alkyl, —O-aryl, or an alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, —COR8, where R8 is H, —OH, an alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, or —OR6 or —NR6R7 where R6 and R7 are each independently hydrogen, alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl;

R4 is independently H, amino, hydroxy, —NH—NH$_2$, —CO—NH—NH$_2$, halogen-substituted amino, —O-alkyl, —O-aryl, alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, —COR8, where R8 is H, —OH, alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, or —OR6 or —NR6R7 or CH₂R6 or CH₂NR6R7 where R6 and R7 are each independently hydrogen or an alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl; and R5 is independently H, amino, hydroxy, —NH—NH₂, —CO—NH—NH₂, halogen-substituted amino, —O-alkyl, —O-aryl, alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl or aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, —COR8, where R8 is H, —OH, alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, or —OR6 or —NR6R7 where R6 and R7 are each independently hydrogen or an alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl.

2. The compound of claim 1:
wherein
R1 is H, F, Cl, methoxy, or methyl;
R2 is H, F, Cl, methoxy, or methyl;
R3 is independently H, amino, hydroxy, —NH—NH₂, halogen-substituted amino, —O-alkyl, —O-aryl, or an alkyl, alkenyl, —COR8, where R8 is H, —OH an alkyl, or alkenyl, or —OR6 or —NR6R7 where R6 and R7 are each independently hydrogen or an alkyl, or alkenyl;
R4 is independently H, amino, hydroxy, —NH—NH₂, —CO—NH—NH₂, halogen-substituted amino, —O-alkyl, —O-aryl, alkyl, alkenyl, —COR8, where R8 is H, —OH an alkyl, or alkenyl, or —OR6 or —NR6R7 or —CH₂R6 or —CH₂NR6R7 where R6 and R7 are each independently hydrogen or an alkyl, alkenyl, alkynyl, unsubstituted cycloalkyl, cycloalkyl substituted by or fused to a 5- or 6-membered aryl or heteroaryl, unsubstituted heterocycloalkyl, heterocycloalkyl substituted by or fused to a 5- or 6-membered aryl or heteroaryl, unsubstituted aryl, aryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl, unsubstituted heteroaryl, or heteroaryl substituted in one to five positions(s) by halo, haloalkyl, hydroxyl, nitro, trifluoromethyl, $C_1$-$C_6$ straight or branched chain alkyl, $C_2$-$C_6$ straight or branched chain alkenyl, $C_1$-$C_6$ alkoxy, $C_2$-$C_6$ alkenyloxy, phenoxy, benzyloxy, amino, thiocarbonyl, ester, thioester, cyano, imino, alkylamino, aminoalkyl, sulfhydryl, thioalkyl, or sulfonyl; and
R5 is independently H, amino, hydroxy, —NH—NH₂, —CO—NH—NH₂, halogen-substituted amino, —O-alkyl, —O-aryl, alkyl, alkenyl, —COR8, where R8 is H, —OH, alkyl, or alkenyl, or —OR6 or —NR6R7 where R6 and R7 are each independently hydrogen, alkyl, or alkenyl; or a pharmaceutically acceptable salt.

3. The compound of claim 2, wherein the compound is selected from the group consisting of:

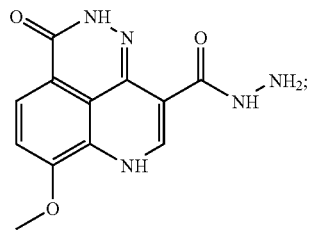

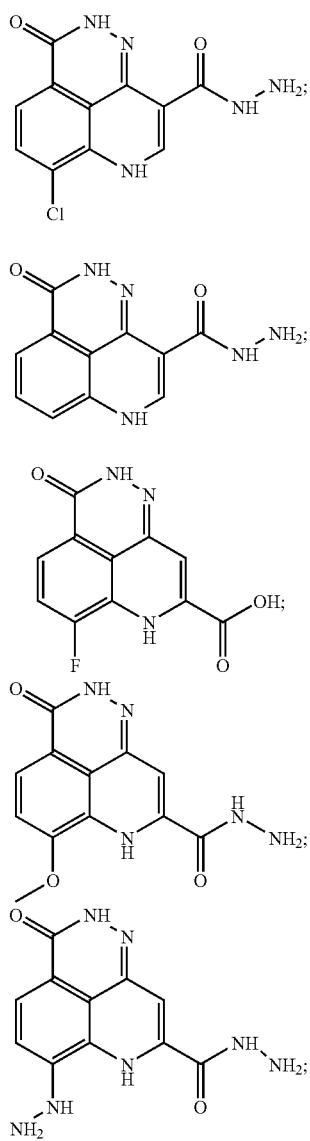

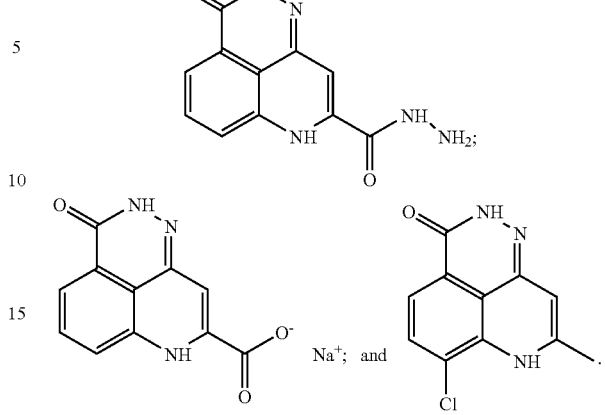

or a pharmaceutically acceptable salt.

4. A method of treating diseases or conditions selected from the group consisting of neural tissue damage resulting from ischemia and reperfusion injury, depression, inflammatory bowel disorders, arthritis, gout, chronic pain, acute pain, neuropathic pain, renal failure, retinal ischemia, and septic shock, comprising administering to said animal an effective amount of a compound of claim 1.

5. The method of claim 4, wherein said ischemia or reperfusion injury is cerebral injury after cardiac arrest and cardiopulmonary resuscitation.

6. The method of claim 4, wherein the septic shock is endotoxic shock.

7. The method of claim 4, wherein the inflammatory bowel disorder is colitis.

8. The method of claim 4, wherein the inflammatory bowel disorder is Crohn's disease.

9. A method of treating melanoma, lymphoma, and glioblastoma multiforme in a mammal comprising administering to said mammal an effective amount of temozolimide and a compound according to claim 1.

10. A pharmaceutical composition comprising:
a therapeutically effective amount of a compound according to claim 1; and
a pharmaceutically acceptable carrier.

* * * * *